(12) United States Patent
Monteleone

(10) Patent No.: US 10,473,669 B2
(45) Date of Patent: Nov. 12, 2019

(54) METHODS FOR TREATING INFLAMMATORY BOWEL DISEASE

(71) Applicant: Nogra Pharma Limited, Dublin (IE)

(72) Inventor: Giovanni Monteleone, Grottaferrata (IT)

(73) Assignee: Nogra Pharma Limited, Dublin (IE)

( * ) Notice: Subject to any disclaimer, the term of this patent is extended or adjusted under 35 U.S.C. 154(b) by 0 days.

(21) Appl. No.: 15/310,060

(22) PCT Filed: May 8, 2015

(86) PCT No.: PCT/EP2015/060269
§ 371 (c)(1),
(2) Date: Nov. 9, 2016

(87) PCT Pub. No.: WO2015/169966
PCT Pub. Date: Nov. 12, 2015

(65) Prior Publication Data
US 2018/0180630 A1      Jun. 28, 2018

Related U.S. Application Data

(60) Provisional application No. 62/065,606, filed on Oct. 17, 2014, provisional application No. 62/065,609, filed on Oct. 17, 2014, provisional application No. 61/991,326, filed on May 9, 2014.

(51) Int. Cl.
| | | |
|---|---|---|
| *G01N 33/68* | (2006.01) | |
| *C12N 15/113* | (2010.01) | |
| *A61P 1/00* | (2006.01) | |
| *A61K 31/7125* | (2006.01) | |
| *A61K 45/06* | (2006.01) | |

(52) U.S. Cl.
CPC ..... *G01N 33/6893* (2013.01); *A61K 31/7125* (2013.01); *A61K 45/06* (2013.01); *A61P 1/00* (2018.01); *C12N 15/113* (2013.01); *G01N 33/6863* (2013.01); *C12N 2310/11* (2013.01); *C12N 2310/315* (2013.01); *G01N 2333/4737* (2013.01); *G01N 2800/065* (2013.01); *G01N 2800/52* (2013.01)

(58) Field of Classification Search
None
See application file for complete search history.

(56) References Cited

U.S. PATENT DOCUMENTS

| | | |
|---|---|---|
| 7,700,572 B2 | 4/2010 | Steinbrecher et al. |
| 7,700,757 B2 | 4/2010 | Monteleone |
| 7,807,818 B2 | 10/2010 | Monteleone |
| 8,106,182 B2 | 1/2012 | Monteleone |
| 8,648,186 B2 | 2/2014 | Monteleone |
| 8,907,078 B2 | 12/2014 | Monteleone |
| 8,912,154 B2 | 12/2014 | Baroni et al. |
| 9,006,418 B2 | 4/2015 | Monteleone |
| 9,096,854 B1 | 8/2015 | Monteleone |
| 9,279,126 B2 | 3/2016 | Monteleone |
| 9,314,434 B2 | 4/2016 | Baroni et al. |
| 9,382,541 B2 | 7/2016 | Monteleone |
| 9,499,819 B2 | 11/2016 | Baroni et al. |
| 9,518,264 B2 | 12/2016 | Monteleone |
| 9,605,264 B2 | 3/2017 | Monteleone |
| 9,791,442 B2 | 10/2017 | Monteleone et al. |
| 9,951,334 B2 | 4/2018 | Monteleone |
| 9,982,264 B2 | 5/2018 | Baroni et al. |
| 10,006,029 B2 | 6/2018 | Monteleone et al. |
| 10,036,022 B2 | 7/2018 | Monteleone |
| 10,081,809 B2 | 9/2018 | Monteleone et al. |
| 10,086,072 B2 * | 10/2018 | Singh ............... C12Q 1/6883 |
| 10,272,047 B2 | 4/2019 | Baroni et al. |
| 10,337,004 B2 | 7/2019 | Monteleone |
| 2005/0118655 A1 | 6/2005 | Weinstock et al. |
| 2005/0119203 A1 | 6/2005 | Steinbrecher et al. |
| 2006/0257932 A1 * | 11/2006 | Ilan ...................... G01N 33/564 |
| | | 435/7.1 |

(Continued)

FOREIGN PATENT DOCUMENTS

| | | |
|---|---|---|
| WO | WO-2003/037368 A2 | 5/2003 |
| WO | WO-2004/087920 A1 | 10/2004 |

(Continued)

OTHER PUBLICATIONS

Monteleone, et al. (2015) "Mongersen, An Oral SMAD7 Antisense Oligonucleotide, and Crohn's Disease," *New England Journal of Medicine*, 372(12):1104-1113.
International Search Report for PCT/EP2015/060269, dated Dec. 16, 2015 (6 pages).
Magro, et al. (2014) "C-Reactive Protein in Crohn's Disease: How Informative is it?", *Expert Review of Gastroenterology & Hepatology*, 8(4):393-408.
Marafini et al. (2013) "TGF-Beta Signaling Manipulation as Potential Therapy for IBD," *Current Drug Targets*, 14(12):1400-1404.
Jürgens et al. (2011) "Levels of C-Reactive Protein are Associated with Response to Infliximab Therapy in Patients with Crohn's Disease," *Clinical Gastroenterology and Hepatology*, 9(5):421-427.
Written Opinion of the International Searching Authority for PCT/EP2015/060269, dated Dec. 16, 2015 (9 pages).
U.S. Appl. No. 10/551,643, filed Jul. 24, 2006, and issued on Apr. 20, 2010 as U.S. Pat. No. 7,700,757.

(Continued)

*Primary Examiner* — Sean McGarry
(74) *Attorney, Agent, or Firm* — Goodwin Procter LLP

(57) ABSTRACT

Methods of treating a subject with IBD with an anti-SMAD7 therapy, such as a SMAD7 antisense oligonucleotide, to reduce CRP levels are disclosed. Methods of treating and managing IBD in a subject using an anti-SMAD7 therapy, such as a SMAD7 antisense oligonucleotide, based on CRP levels are also disclosed. Also disclosed are methods of determining whether a subject with IBD is responsive or likely to be responsive to treatment an anti-SMAD7 therapy. Reduction of CRP levels may correlated with IBD remission or decreases in CDAI score. The present invention also relates to treatment of IBD using an anti-SMAD7 therapy (e.g., an antisense oligonucleotide) in combination with an additional agent. The invention also features related pharmaceutical compositions and kits.

26 Claims, 9 Drawing Sheets

Specification includes a Sequence Listing.

(56) References Cited

U.S. PATENT DOCUMENTS

| | | | |
|---|---|---|---|
| 2007/0042985 A1 | 2/2007 | Monteleone | |
| 2007/0167385 A1 | 7/2007 | Monteleone | |
| 2009/0156539 A1 | 6/2009 | Monteleone | |
| 2010/0317719 A1 | 12/2010 | Monteleone | |
| 2011/0207795 A1 | 8/2011 | Steinbrecher et al. | |
| 2012/0015033 A1 | 1/2012 | Baroni et al. | |
| 2012/0136043 A1 | 5/2012 | Monteleone | |
| 2013/0203839 A1 | 8/2013 | Monteleone | |
| 2013/0316000 A1* | 11/2013 | Bortey | A61K 31/196 424/490 |
| 2014/0142163 A1 | 5/2014 | Monteleone | |
| 2014/0256788 A1 | 9/2014 | Monteleone | |
| 2014/0271860 A1 | 9/2014 | Monteleone et al. | |
| 2015/0125523 A1 | 5/2015 | Baroni et al. | |
| 2015/0148245 A1 | 5/2015 | Monteleone et al. | |
| 2015/0152182 A1* | 6/2015 | Taylor | C07K 16/2839 424/85.6 |
| 2015/0211011 A1 | 7/2015 | Monteleone | |
| 2015/0218561 A1 | 8/2015 | Monteleone | |
| 2015/0232854 A1 | 8/2015 | Baroni et al. | |
| 2015/0315573 A1 | 11/2015 | Monteleone et al. | |
| 2015/0337312 A1 | 11/2015 | Monteleone | |
| 2016/0161501 A1* | 6/2016 | Koon | G01N 33/6893 506/9 |
| 2016/0177306 A1 | 6/2016 | Monteleone | |
| 2016/0222383 A1 | 8/2016 | Baroni et al. | |
| 2016/0304876 A1 | 10/2016 | Monteleone | |
| 2017/0107520 A1 | 4/2017 | Baroni et al. | |
| 2017/0168070 A1* | 6/2017 | Oberoi | C12Q 1/6883 |
| 2017/0233736 A1* | 8/2017 | Monteleone | C12N 15/113 514/44 A |
| 2017/0240893 A1 | 8/2017 | Monteleone | |
| 2017/0253880 A1 | 9/2017 | Monteleone | |
| 2017/0307637 A1* | 10/2017 | Westin | G01N 33/6893 |
| 2018/0030450 A1 | 2/2018 | Monteleone | |
| 2018/0128829 A1 | 5/2018 | Monteleone et al. | |
| 2019/0100758 A1 | 4/2019 | Monteleone et al. | |
| 2019/0136237 A1 | 5/2019 | Monteleone et al. | |

FOREIGN PATENT DOCUMENTS

| | | |
|---|---|---|
| WO | WO-2010/054826 A1 | 5/2010 |
| WO | WO-2011/093817 A1 | 8/2011 |
| WO | WO-2013/037970 A1 | 3/2013 |
| WO | WO-2013/158868 A1 | 10/2013 |
| WO | WO-2014/140333 A1 | 9/2014 |
| WO | WO-2015/169966 A2 | 11/2015 |
| WO | WO-2016/059239 A1 | 4/2016 |
| WO | WO-2016/059243 A2 | 4/2016 |
| WO | WO-2017/055611 A2 | 4/2017 |
| WO | WO-2017/144689 A1 | 8/2017 |
| WO | WO-2018/122376 A1 | 7/2018 |

OTHER PUBLICATIONS

U.S. Appl. No. 11/501,756, filed Aug. 10, 2006, now abandoned.
U.S. Appl. No. 12/264,058, filed Nov. 3, 2008, and issued on Oct. 5, 2010 as U.S. Pat. No. 7,807,818.
U.S. Appl. No. 12/854,558, filed Aug. 11, 2010, and issued on Jan. 31, 2012 as U.S. Pat. No. 8,106,182.
U.S. Appl. No. 13/332,134, filed Dec. 20, 2011, now abandoned.
U.S. Appl. No. 13/836,634, filed Mar. 15, 2013, and issued on Feb. 11, 2014 as U.S. Pat. No. 8,648,186.
U.S. Appl. No. 14/144,029, filed Dec. 30, 2013, and issued on Apr. 14, 2015 as U.S. Pat. No. 9,006,418.
U.S. Appl. No. 14/266,343, filed Apr. 30, 2014, and issued on Dec. 9, 2014 as U.S. Pat. No. 8,907,078.
U.S. Appl. No. 14/613,181, filed Feb. 3, 2015, and issued on Aug. 4, 2015 as U.S. Pat. No. 9,096,854.
U.S. Appl. No. 14/685,091, filed Apr. 13, 2015, and issued on Mar. 8, 2016 as U.S. Pat. No. 9,279,126.
U.S. Appl. No. 14/815,339, filed Jul. 31, 2015, and issued on Jul. 5, 2016 as U.S. Pat. No. 9,382,541.
U.S. Appl. No. 15/063,077, filed Mar. 7, 2016, and issued on Mar. 28, 2017 as U.S. Pat. No. 9,605,264.
U.S. Appl. No. 15/201,061, filed Jul. 1, 2016, and issued on Dec. 13, 2016 as U.S. Pat. No. 9,518,264.
U.S. Appl. No. 15/355,329, filed Nov. 18, 2016, and issued on Jul. 31, 2018 as U.S. Pat. No. 10,036,022.
U.S. Appl. No. 15/457,631, filed Mar. 13, 2017, and issued on Apr. 28, 2018 as U.S. Pat. No. 9,951,334.
U.S. Appl. No. 15/928,494, filed Mar. 22, 2018, still pending.
U.S. Appl. No. 16/046,389, filed Jul. 26, 2018, still pending.
U.S. Appl. No. 13/129,205, filed Sep. 30, 2011, and issued on Dec. 16, 2014 as U.S. Pat. No. 8,912,154.
U.S. Appl. No. 14/570,293, filed Dec. 15, 2014, and issued on Apr. 19, 2016 as U.S. Pat. No. 9,314,434.
U.S. Appl. No. 15/130,737, filed Apr. 15, 2016, and issued on May 29, 2018 as U.S. Pat. No. 9,982,264.
U.S. Appl. No. 15/989,858, filed May 25, 2018, still pending.
U.S. Appl. No. 14/570,313, filed Dec. 15, 2014, and issued on Nov. 22, 2016 as U.S. Pat. No. 9,499,819.
U.S. Appl. No. 15/335,198, filed Oct. 26, 2016, still pending.
U.S. Appl. No. 16/201,201, filed Nov. 27, 2018, still pending.
U.S. Appl. No. 10/494,333, filed Apr. 30, 2004, and issued on Apr. 20, 2010 as U.S. Pat. No. 7,700,572.
U.S. Appl. No. 12/565,629, filed Sep. 23, 2009, now abandoned.
U.S. Appl. No. 13/624,461, filed Sep. 21, 2012, now abandoned.
U.S. Appl. No. 14/344,969, filed Mar. 14, 2014, and issued on Oct. 17, 2017, as U.S. Pat. No. 9,791,442.
U.S. Appl. No. 15/705,715, filed Sep. 15, 2017, still pending.
U.S. Appl. No. 14/394,999, filed Oct. 16, 2014, and issued on Sep. 25, 2018 as U.S. Pat. No. 10,081,809.
U.S. Appl. No. 16/100,906, filed Aug. 10, 2018, still pending.
U.S. Appl. No. 14/211,471, filed Mar. 14, 2014, and issued on Jun. 26, 2018 as U.S. Pat. No. 10,006,029.
U.S. Appl. No. 16/002,520, filed Jun. 7, 2018, still pending.
U.S. Appl. No. 15/519,489, filed Apr. 14, 2017, still pending.
U.S. Appl. No. 15/519,468, filed Apr. 14, 2017, still pending.
U.S. Appl. No. 15/764,567, filed Mar. 29, 2018, still pending.
U.S. Appl. No. 16/079,232, filed Aug. 23, 2018, still pending.
Monteleone, et al. (2008) "TGF-β1 and Smad7 in the Regulation of IBD," *Mucosal Immunology* 1(1):S50-S53.
Ran, et al. (2010) "Study on the Function of Infliximab in Inducing Remission in Crohn's Disease and Followed-Up," *Chin J Dig* 30(12):894-897. (Abstract in English).
Zheng (2013) "The Clinical Significance of C-Reactive Protein in Inflammatory Bowel Disease Patients," *Chinese Journal of Health Laboratory Technology* 23(2):395-396.
Zorzi, et al. (2012) "A Phase 1 Open-Label Trial Shows that SMAD7 Antisense Oligonucleotide (GED0301) Does not Increase the Risk of Small Bowel Strictures in Crohn's Disease," *Ailment Pharmacol Ther* 36:850-857.

* cited by examiner

Day 15 vs Baseline

Day 28 vs Baseline

SEQUENCE LISTING

```
<160> NUMBER OF SEQ ID NOS: 13

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine

<400> SEQUENCE: 1
gtcgcccctt ctccccgcag c                                              21

<210> SEQ ID NO 2
<211> LENGTH: 3088
<212> TYPE: DNA
<213> ORGANISM: Homo sapiens

<400> SEQUENCE: 2
cggagagccg cgcagggcgc gggccgcgcg gggtggggca gccggagcgc aggcccccga      60
tccccggcgg gcgcccccgg gccccgcgc gcgcccccggc ctccgggaga ctggcgcatg     120
ccacggagcg cccctcgggc cgccgccgct cctgcccggg ccctgctgc tgctgctgtc     180 gcctgcgcct gctgccccaa ctcggcgccc gacttcttca tggtgtgcgg aggtcatgtt     240
cgctccttag caggcaaacg acttttctcc tcgcctcctc gccccgcatg ttcaggacca     300
aacgatctgc gctcgtccgg cgtctctgga ggagccgtgc gccgggcggc gaggacgagg     360
aggagggcgc aggggaggt ggaggaggag gcgagctgcg gggagaaggg gcgacggaca     420
gccgagcgca tggggccggt ggcggcggcc cgggcagggc tggatgctgc ctgggcaagg     480
cggtgcgagg tgccaaaggt caccaccatc cccacccgcc agccgcgggc gccggcgcgg     540 ccggggggcgc cgaggcggat ctgaaggcgc tcacgcactc ggtgctcaag aaactgaagg     600
agcggcagct ggagctgctg ctccaggccg tggagtcccg cggcgggacg cgcaccgcgt     660
gcctcctgct gcccggccgc ctggactgca ggctgggccc ggggcgcgcc gccggcgcgc     720
agcctgcgca gccgccctcg tcctactcgc tccccctcct gctgtgcaaa gtgttcaggt     780
ggccggatct caggcattcc tcggaagtca agaggctgtg ttgctgtgaa tcttacggga     840
agatcaaccc cgagctggtg tgctgcaacc cccatcacct tagccgactc tgcgaactag     900
agtctccccc ccctccttac tccagatacc cgatggattt tctcaaacca actgcagact     960
gtccagatgc tgtgccttcc tccgctgaaa caggggggaac gaattatctg gcccctgggg    1020
ggctttcaga ttcccaactt cttctggagc ctggggatcg gtcacactgg tgcgtggtgg    1080
catactggga ggagaagacg agagtgggga ggctctactg tgtccaggag ccctctctgg    1140
atatcttcta tgatctacct caggggaatg gcttttgcct cggacagctc aattcggaca    1200
```

```
acaagagtca gctggtgcag aaggtgcgga gcaaaatcgg ctgcggcatc cagctgacgc    1260
gggaggtgga tggtgtgtgg gtgtacaacc gcagcagtta ccccatcttc atcaagtccg    1320
ccacactgga caacccggac tccaggacgc tgttggtaca aaggtgttc cccggtttct     1380 ccatcaaggc tttcgactac gagaaggcgt acagcctgca gcggcccaat gaccacgagt    1440
ttatgcagca gccgtggacg ggctttaccg tgcagatcag ctttgtgaag ggctggggcc    1500
agtgctacac ccgccagttc atcagcagct gcccgtgctg gctagaggtc atcttcaaca    1560
gccggtagcc gcgtgcggag gggacagagc gtgagctgag caggccacac ttcaaactac    1620
tttgctgcta atattttcct cctgagtgct tgcttttcat gcaaactctt tggtcgtttt    1680
ttttttgttt gttggttggt tttcttcttc tcgtcctcgt ttgtgttctg ttttgtttcg    1740
ctctttgaga aatagcttat gaaaagaatt gttgggggtt tttttggaag aaggggcagg    1800
tatgatcggc aggacaccct gataggaaga ggggaagcag aaatccaagc accaccaaac    1860
acagtgtatg aagggggggcg gtcatcattt cacttgtcag gagtgtgtgt gagtgtgagt    1920
gtgcggctgt gtgtgcacgc gtgtgcagga gcggcagatg gggagacaac gtgctctttg    1980
ttttgtgtct cttatggatg tccccagcag agaggtttgc agtcccaagc ggtgtctctc    2040 ctgcccttg gacacgctca gtggggcaga ggcagtacct gggcaagctg gcggctgggg     2100
tcccagcagc tgccaggagc acggctctgt ccccagcctg ggaaagcccc tgcccctcct    2160
ctccctcatc aaggacacgg gcctgtccac aggcttctga gcagcgagcc tgctagtggc    2220
cgaaccagaa ccaattattt tcatccttgt cttattccct tcctgccagc ccctgccatt    2280
gtagcgtctt tctttttggg ccatctgctc ctggatctcc ctgagatggg cttcccaagg    2340
gctgccgggg cagcccccctc acagtattgc tcacccagtg ccctctcccc tcagcctctc    2400
ccctgcctgc cctggtgaca tcaggttttt cccggactta gaaaaccagc tcagcactgc    2460
ctgctcccat cctgtgtgtt aagctctgct attaggccag caagcgggga tgtccctggg    2520
agggacatgc ttagcagtcc ccttccctcc aagaaggatt tggtccgtca taacccaagg    2580
taccatccta ggctgacacc taactcttct ttcatttctt ctacaactca tacactcgta    2640
tgatacttcg acactgttct tagctcaatg agcatgttta gactttaaca taagctattt    2700
ttctaactac aaaggtttaa atgaacaaga gaagcattct cattggaaat ttagcattgt    2760
agtgctttga gagagaaagg actcctgaaa aaaaacctga gatttattaa agaaaaaaat    2820
gtattttatg ttatatataa atatattatt acttgtaaat ataagacgt tttataagca      2880 tcattattta tgtattgtgc aatgtgtata aacaagaaaa ataagaaaa gatgcacttt     2940 gctttaatat aaatgcaaat aacaaatgcc aaattaaaaa agataaacac aagattggtg    3000 ttttttcta tgggtgttat cacctagctg aatgttttc taaaggagtt tatgttccat     3060
taaacgattt ttaaaatgta cacttgaa                                       3088
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtcgcccctt ctccccgcag c                                                21

<210> SEQ ID NO 4

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-methyl-2'-deoxycytidine
<220> FEATURE:
<221> NAME/KEY: modified_base
<222> LOCATION: (16)..(16)
<223> OTHER INFORMATION: 5-methyl-2'-deoxycytidine

<400> SEQUENCE: 4
gtcgcccctt ctccccgcag                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: Nitrogenous base selected from the group
      consisting of cytosine and 5-methylcytosine or a 2'-O-methyl
      nucleoside comprising a cytosine nucleobase
<220> FEATURE:
<221> NAME/KEY: modified_base
<222> LOCATION: (4)..(4)
<223> OTHER INFORMATION: Nitrogenous base selected from the group
      consisting of guanine and 5-methylguanine or a 2'-O-methyl
      nucleoside comprising a guanine nucleobase
<220> FEATURE:
<221> NAME/KEY: modified_base
<222> LOCATION: (16)..(16)
<223> OTHER INFORMATION: Nitrogenous base selected from the group
      consisting of cytosine and 5-methylcytosine or a 2'-O-methyl
      nucleoside comprising a cytosine nucleobase
<220> FEATURE:
<221> NAME/KEY: modified_base
<222> LOCATION: (17)..(17)
<223> OTHER INFORMATION: Nitrogenous base selected from the group
      consisting of guanine and 5-methylguanine or a 2'-O-methyl
      nucleoside comprising a guanine nucleobase
<220> FEATURE:
<223> OTHER INFORMATION: See specification as filed for detailed
      description of substitutions and preferred embodiments

<400> SEQUENCE: 5
gtcgcccctt ctccccgcag                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxyguanosine methylphosphonate
<220> FEATURE:
<221> NAME/KEY: modified_base
<222> LOCATION: (3)..(3)
<223> OTHER INFORMATION: 5-methyl 2'-deoxycytidine
<220> FEATURE:
<221> NAME/KEY: modified_base
<222> LOCATION: (16)..(16)
<223> OTHER INFORMATION: 5-methyl 2'-deoxycytidine
```

```
<220> FEATURE:
<221> NAME/KEY: modified_base
<222> LOCATION: (20)..(20)
<223> OTHER INFORMATION: 2'-deoxyguanosine methylphosphonate

<400> SEQUENCE: 6
gtcgcccctt ctccccgcag                                                   20

<210> SEQ ID NO 7
<211> LENGTH: 21
<212> TYPE: DNA
<213> ORGANISM: Homo sapiens

<400> SEQUENCE: 7
gctgcgggga gaagggcga c                                                  21

<210> SEQ ID NO 8
<211> LENGTH: 2321
<212> TYPE: DNA
<213> ORGANISM: Homo sapiens

<400> SEQUENCE: 8
aggcaggagg aggtagctct aaggcaagag atctaggact tctagcccct gaactttcag       60
ccgaatacat ctttttccaaa ggagtgaatt caggcccttg tatcactggc agcaggacgt     120
gaccatggaa aagctgttgt gtttcttggt cttgaccagc ctctctcatg cttttggcca     180
gacaggtaag ggccacccca ggctatggga gagatttgat ctgaggtatg ggggtggggt     240
ctaagactgc atgaacagtc tcaaaaaaaa aaaaaaaga ctgtatgaac agaacagtgg     300
agcatccttc atggtgtgtg tgtgtgtgtg tgtgtgtgtg tgtgtgtgtg tggtgtgtaa     360
ctggagaagg ggtcagtctg tttctcaatc ttaaattcta tacgtaagtg aggggataga     420
tctgtgtgat ctgagaaacc tctcacattt gcttgttttt ctggctcaca gacatgtcga     480
ggaaggcttt tgtgtttccc aaagagtcgg atacttccta tgtatccctc aaagcaccgt     540
taacgaagcc tctcaaagcc ttcactgtgt gcctccactt ctacacggaa ctgtcctcga     600
cccgtgggta cagtattttc tcgtatgcca ccaagagaca agacaatgag attctcatat     660
tttggtctaa ggatatagga tacagttttta cagtgggtgg gtctgaaata ttattcgagg     720
ttcctgaagt cacagtagct ccagtacaca tttgtacaag ctgggagtcc gcctcaggga     780
tcgtggagtt ctgggtagat gggaagccca gggtgaggaa gagtctgaag aagggataca     840
ctgtgggggc agaagcaagc atcatcttgg ggcaggagca ggattccttc ggtgggaact     900
ttgaaggaag ccagtccctg gtgggagaca ttggaaatgt gaacatgtgg gactttgtgc     960
tgtcaccaga tgagattaac accatctatc ttggcgggcc cttcagtcct aatgtcctga    1020
actggcgggc actgaagtat gaagtgcaag gcgaagtgtt caccaaaccc agctgtggc    1080 cctgaggccc agctgtgggt cctgaaggta cctcccggtt ttttacaccg catgggcccc    1140
acgtctctgt ctctggtacc tcccgctttt ttacactgca tggttcccac gtctctgtct    1200
ctgggccttt gttcccctat atgcattgca ggcctgctcc accctcctca gcgcctgaga    1260
atggaggtaa agtgtctggt ctgggagctc gttaactatg ctgggaaacg gtccaaaaga    1320
atcagaattt gaggtgtttt gttttcattt ttatttcaag ttggacagat cttggagata    1380
atttcttacc tcacatagat gagaaaacta acacccagaa aggagaaatg atgttataaa    1440
aaactcataa ggcaagagct gagaaggaag cgctgatctt ctatttaatt ccccaccccat    1500 gacccccaga aagcaggagg gcattgccca cattcacagg gctcttcagt ctcagaatca    1560
```

```
ggacactggc caggtgtctg gtttgggtcc agagtgctca tcatcatgtc atagaactgc   1620
tgggcccagg tctcctgaaa tgggaagccc agcaatacca cgcagtccct ccactttctc   1680
aaagcacact ggaaaggcca ttagaattgc cccagcagag cagatctgct ttttttccag   1740
agcaaaatga agcactaggt ataaatatgt tgttactgcc aagaacttaa atgactggtt   1800
tttgtttgct tgcagtgctt tcttaatttt atggctcttc tgggaaactc ctccccttt    1860 ccacacgaac cttgtggggc tgtgaattct ttcttcatcc ccgcattccc aatatacccca  1920 ggccacaaga gtggacgtga accacagggt gtcctgtcag aggagcccat ctcccatctc   1980
cccagctccc tatctggagg atagttggat agttacgtgt tcctagcagg accaactaca   2040
gtcttcccaa ggattgagtt atggactttg ggagtgagac atcttcttgc tgctggattt   2100
ccaagctgag aggacgtgaa cctgggacca ccagtagcca tcttgtttgc cacatggaga   2160
gagactgtga ggacagaagc caaactggaa gtggaggagc caagggattg acaaacaaca   2220
gagccttgac cacgtggagt ctctgaatca gccttgtctg gaaccagatc tacacctgga   2280
ctgcccaggt ctataagcca ataaagcccc tgtttacttg a                       2321
```

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agcatagtta acgagctccc                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcactctgga cccaaaccag                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcccatttca ggagacctgg                                                20

<210> SEQ ID NO 12
<211> LENGTH: 2438
<212> TYPE: DNA
<213> ORGANISM: Homo sapiens

<400> SEQUENCE: 12
aataaataac tcacattgat ttctctggtc tgaaataatt ttgcttcccc tcttcccgaa    60
gctctgacac ctgccccaac aagcaatgtt ggaaaattat ttacatagtg gcgcaaactc    120
ccttactgct ttggatataa atccaggcag gaggaggtag ctctaaggca agagatctag    180
```

```
gacttctagc ccctgaactt tcagccgaat acatcttttc caaaggagtg aattcaggcc      240
cttgtatcac tggcagcagg acgtgaccat ggagaagctg ttgtgtttct tggtcttgac      300
cagcctctct catgcttttg ccagacagg taagggccac cccaggctat gggagagttt       360
tgatctgagg tatggggggtg gggtctaaga ctgcatgaac agtctcaaaa aaaaaaaaaa     420
aagactgtat gaacagaaca gtggagcatc cttcatggtg tgtgtgtgtg tgtgtgtgtg      480 tgtgtgggt gtgtaactgg agaaggggtc agtctgtttc tcaatcttaa attctatacg       540
taagtgaggg gatagatctg tgtgatctga gaaacctctc acatttgctt gttttctgg       600 ctcacagaca tgtcgaggaa ggcttttgtg tttcccaaag agtcggatac ttcctatgta      660
tccctcaaag caccgttaac gaagcctctc aaagccttca ctgtgtgcct ccacttctac      720
acggaactgt cctcgacccg tgggtacagt attttctcgt atgccaccaa gagacaagac      780
aatgagattc tcatattttg gtctaaggat ataggataca gttttacagt gggtgggtct      840
gaaatattat tcgaggttcc tgaagtcaca gtagctccag tacacatttg tacaagctgg      900
gagtccgcct cagggatcgt ggagttctgg gtagatggga agcccagggt gaggaagagt      960
ctgaagaagg gatacactgt gggggcagaa gcaagcatca tcttggggca ggagcaggat     1020
tccttcggtg ggaactttga aggaagccag tccctagtgg gagacattgg aaatgtgaac     1080
atgtgggact ttgtgctgtc accagatgag attaacacca tctatcttgg cgggccttc      1140 agtcctaatg tcctgaactg gcgggcactg aagtatgaag tgcaaggcga agtgttcacc      1200 aaacccagc tgtggccctg aggcccagct gtgggtcctg aaggtacctc ccggtttttt      1260
acaccgcatg ggcccacgt ctctgtctct ggtacctccc gcttttttac actgcatggt      1320
tcccacgtct ctgtctctgg gcctttgttc ccctatatgc attgaggcct gctccaccct     1380
cctcagcgcc tgagaatgga ggtaaagtgt ctggtctggg agctcgttaa ctatgctggg     1440
aaatggtcca aagaatcag aatttgaggt gttttgtttt catttttatt tcaagttgga      1500
cagatcttgg agataaattc ttacctcaca tagatgagaa aactaacacc cagaaaggag     1560
aaatgatgtt ataaaaaact cataaggcaa gagctgagaa ggaagcgctg atcttctatt     1620
taattcccca cccatgaccc ccagaaaagca ggagcattgc ccacattcac agggctcttc    1680
agtatcagaa tcaggacact ggccaggtgt ctggtttggg tccagagtgc tcatcatcat     1740
gtcatagaac tgctgggccc aggtctcctg aaatgggaag cccagcaata ccacgcagtc     1800
cctccacttt ctcaaagcac actggaaagg ccattagaat tgccccagca gagcagatct     1860 gcttttttc cagagcaaaa tgaagcacta ggtataaata tgttgttact gccaagaact       1920
taaatgactg gttttgttt gcttgcagtg ctttcttaat tttatggctc ttctgggaaa       1980
ctcctcccct tttccacacg aaccttgtgg ggctgtgaat tctttcttca tccccgcatt     2040
cccaatatac ccaggccaca agagtggacg tgaaccacag ggtgtcctgt cagaggagcc     2100
catctcccat ctccccagct ccctatctgg aggatagttg gataggtacg tgttcctagc     2160
aggaccaact acagtcttcc caaggattga gttatggact ttgggagtga gacatcttct     2220
tgctgctgga tttccaagct gagaggacgt gaacctggga ccaccagtag ccatcttgtt     2280
tgccacatgg agagagactg tgaggacaga agccaaactg gaagtggagg agccaaggga     2340
ttgacaaaca acagagcctt gaccacgtgg agtctctgaa tcagccttgt ctggaaccag     2400
atctacacct ggactgccca ggtctataag ccaataaa                             2438

<210> SEQ ID NO 13
<211> LENGTH: 224
```

```
-continued

<212> TYPE: PRT
<213> ORGANISM: Homo sapiens

<400> SEQUENCE: 13

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
            115                 120                 125

Val Asp Gly Lys Pro Arg Val Arg Lys Ser Leu Lys Lys Gly Tyr Thr
    130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
    210                 215                 220
```

METHODS FOR TREATING INFLAMMATORY BOWEL DISEASE

CROSS-REFERENCE TO RELATED APPLICATIONS

This application is a national stage filing under 35 U.S.C. § 371 of International Patent Application No. PCT/EP2015/060269, filed May 8, 2015, which claims priority to U.S. Patent Application No. 61/991,326, filed May 9, 2014; U.S. Patent Application No. 62/065,609, filed Oct. 17, 2014; and U.S. Patent Application No. 62/065,606, filed Oct. 17, 2014, the entire disclosure of each of which is incorporated by reference herein for all purposes.

BACKGROUND

Inflammatory bowel disease (IBD) is a chronic inflammatory disorder of the gastrointestinal tract suffered by approximately one million patients in the United States. The two most common forms of IBD are Crohn's disease (CD) and ulcerative colitis (UC). Although CD can affect the entire gastrointestinal tract, it primarily affects the ileum (the distal or lower portion of the small intestine) and the large intestine. UC primarily affects the colon and the rectum. Current treatment for both CD and UC include aminosalicylates (e.g., 5-aminosalicylic acid, sulfasalazine and mesalamine), antibiotics (e.g., ciprofloxacin and metronidazole), corticosteroids (e.g., budesonide or prednisone), immunosuppressants (e.g., azathioprine or methotrexate) and tumor necrosis factor (TNF) antagonists (e.g., infliximab (Remicade®)). Patient response to these therapies varies with disease severity and it can vary over cycles of active inflammation and remission. Moreover, many of the current therapies for IBD are associated with undesirable side effects.

Although the etiologies of CD and UC are unknown, both are considered inflammatory diseases of the intestinal mucosa. Recent studies have demonstrated that TGF-β1 acts as a potent immunoregulator able to control mucosal intestinal inflammation. TGF-β1 binds a heterodimeric transmembrane serine/threonine kinase receptor containing two subunits, TGF-β1 R1 and TGF-β1 R2. Upon ligand binding, the TGF-β1 R1 receptor is phosphorylated by the constitutively active TGF-β1 R2 receptor and signal is propagated to the nucleus by proteins belonging to the SMAD family. Activated TGF-β1 R1 directly phosphorylates SMAD2 and SMAD3 proteins, which then interact with SMAD4. The complex of SMAD2/SMAD3/SMAD4 translocates to the nucleus and modulates the transcription of certain genes.

Additional studies have demonstrated that another SMAD protein, SMAD7, also plays a role in inflammation. SMAD7, an intracellular protein, has been shown to interfere with binding of SMAD2/SMAD3 to the TGF-β1 R1, preventing phosphorylation and activation of these proteins. Further, increased expression of SMAD7 protein is associated with an inhibition of TGF-β1 mediated-signaling. Mucosal samples from IBD patients are characterized by high levels of SMAD7 and reduced levels of phosphorylated-SMAD3 indicating that TGF-131-mediated signaling is compromised in these patients.

Recent studies have focused on SMAD7 as a target for treating patients suffering from IBD. Such therapies include anti-SMAD7 antisense therapies. As such, there is a need for methods based on predictive biomarkers that can be used to identify patients that are likely (or unlikely) to respond to treatment with anti-SMAD7 therapies and methods of evaluating treatment success.

SUMMARY

The invention is based, in part, on the discovery that levels of CRP in a patient with IBD correlate with IBD disease state and can be used as a means for monitoring disease state and managing responsiveness to IBD treatment with an anti-SMAD7 therapy. The invention is also based, in part, on the discovery that modulation of circulating CRP concentration in a subject with IBD correlates with sensitivity to treatment with an anti-SMAD7 therapy. Therefore, the invention is also based on the discovery that one can use monitoring and analysis of CRP levels in a patient with IBD to determine appropriate levels of SMAD7 antisense oligonucleotide administration and to regulate and adjust SMAD7 antisense oligonucleotide treatment. Additionally, the invention is based, in part, on the discoveries that administration of an anti-SMAD7 therapy is effective in treating a subject having a high circulating CRP concentration, and that administration of an anti-SMAD7 therapy is effective in reducing CRP levels in a subject with IBD.

It will be appreciated that it is advantageous to be able to predict in advance, shortly after commencing treatment, shortly before stopping treatment, or shortly after stopping treatment, whether an IBD patient is responsive or likely to be responsive to treatment with an anti-SMAD7 therapy, in particular, a SMAD7 antisense oligonucleotide. Modulation of CRP concentration as described herein is predictive of the efficacy of the treatment of a subject having IBD with an anti-SMAD7 therapy. Furthermore, CRP concentration can be used to determine whether a subject is likely to respond to an anti-SMAD7 therapy. Advantageously, the methods of the invention will ultimately assist physicians in choosing effective therapies and lead to improvements in a patient's disease status, better medical care and reduction in overall patient costs.

Furthermore, modulation of CRP levels in a patient with IBD, as described herein, is useful for evaluating the efficacy of and responsiveness to treatment with an anti-SMAD7 therapy in a subject having IBD. Furthermore, it will be appreciated that it is advantageous to be able to evaluate and modulate administration of an anti-SMAD7 therapy in a patient with IBD based on levels, or changes in levels, of a biomarker, e.g., CRP, that correlate with disease state. Thus, the invention provides methods for analyzing levels of CRP in a patient being treated with or who has been administered an anti-SMAD7 therapy, e.g., a SMAD7 antisense oligonucleotide, and adjusting dosage levels based on changes in CRP levels or CRP levels determined by an analyzing step, following a dose of the anti-SMAD7 therapy. Advantageously, the methods of the invention will ultimately assist physicians in monitoring and adjusting treatment with therapies that target SMAD7 activity. Furthermore, methods of the invention will lead to improvements in IBD treatment efficacy for patients.

In a first aspect, the invention provides a method of treating IBD in a subject having an increased circulating CRP concentration, for example, a circulating CRP concentration greater than about 3.0 mg/liter, about 3.5 mg/liter, about 4.0 mg/liter, or higher. In a preferred embodiment, the invention provides a method of treating IBD in a subject having a circulating CRP concentration greater than about 3.0 mg/liter. In some embodiments, the invention provides a method of treating IBD in a subject having a circulating CRP concentration greater than about 3.0 mg/liter, where the method comprises a step (a) of administering at least one anti-SMAD7 therapy to the subject.

In another aspect, the invention provides a method of reducing CRP levels in a subject with IBD, where the method comprises a step (a) of administering at least one anti-SMAD7 therapy to the subject. In some embodiments, CRP levels prior to treatment are greater than about 3.0 mg/liter, about 3.5 mg/liter, about 4.0 mg/liter, or higher. In some embodiments, CRP levels after treatment are less than about 0.1 mg/liter, about 0.5 mg/liter, about 1.0 mg/liter, about 1.5 mg/liter, about 2.0 mg/liter, about 2.5 mg/liter, or about 3.0 mg/liter. In a preferred embodiment, CRP levels prior to treatment are greater than 3.0 mg/liter and CRP levels after treatment are less than 3.0 mg/liter.

In another aspect, the invention provides a method for treating or managing IBD in a patient having IBD, where the method comprises steps (a) establishing a control level of CRP for the patient; (b) administering to the patient an initial dose of a SMAD7 antisense-oligonucleotide; (c) analyzing the level of CRP in the patient; and (d) if the level of CRP is lower than the control level, then administering to the patient a subsequent dose that is the same as the initial dose or smaller than the initial dose, or, if the level of CRP is unchanged or increased compared to the control level, then administering to the patient a subsequent dose that is the same as the initial dose or greater than the initial dose or terminating the treatment.

In some embodiments of the invention, a method of treatment will include a step of measuring circulating CRP concentration in a subject prior to step (a) of administering at least one anti-SMAD7 therapy. In yet other embodiments of the invention, a method of treatment will include a further step, following step (a), of measuring the circulating CRP concentration in the subject to determine whether any change in circulating CRP concentration has occurred. Thus, in either a method of treating IBD in a subject having a circulating CRP concentration greater than 3.0 mg/liter or a method of reducing CRP levels in a subject with IBD, the method may include a step, prior to step (a) of measuring circulating CRP concentration in the subject, a step (a) of administering at least one anti-SMAD7 therapy to the patient, and, optionally, a further step of measuring circulating CRP concentration in the subject to determine whether any change in CRP concentration has occurred. It is understood that a determination of whether any change in CRP concentration has occurred can be made by comparing the measured circulating CRP concentrations obtained during each of the steps that occur prior to and following step (a).

In some embodiments, circulating CRP concentration may be measured by taking a sample, for example, a blood sample, from the subject. In some embodiments, the concentration of CRP in the sample taken from the subject after step (a) of any of the treatment methods described herein is less than 3.0 mg/liter, for example, less than about 3.0 mg/liter, less than about 2.0 mg/liter, less than about 1.0 mg/liter, less than about 0.5 mg/liter, or less than about 0.1 mg/liter.

In yet another aspect, the invention provides a method for monitoring responsiveness of a subject with IBD to treatment with at least one anti-SMAD7 therapy, where the method includes the following steps: (a) determining the concentration of CRP in at least one sample obtained from the subject; and (b) comparing the concentration of CRP in the sample with a control level of CRP.

Furthermore, in the contemplated method, a decrease in the concentration of CRP in the sample indicates that the subject is likely to respond, or is responsive to the anti-SMAD7 therapy. The sample obtained from the subject may be a blood sample. In certain embodiments, the subject is receiving at least one anti-SMAD7 therapy when the sample is obtained. The control level of CRP may be determined by measuring CRP levels prior to or just after administration of the anti-SMAD7 therapy. In certain embodiments, the method may comprise the additional step of administering at least one anti-SMAD7 therapy to the subject, prior to step (a). In such embodiments, the anti-SMAD7 therapy may be administered to the subject immediately prior to or about 1 day, about 1 week, about 2 weeks, about 1 month, about 6 months, about 1 year, or longer, prior to step (a). In addition, in some embodiments, the contemplated method may include the optional step of administering at least one anti-SMAD7 therapy to the subject following step (b). In such embodiments, the anti-SMAD7 therapy may be administered to the subject about 1 day, about 1 week, about 2 weeks, about 1 month, about 6 months, about 1 year or longer, or immediately following step (b).

The concentration of CRP in a sample taken from a subject is used to determine whether a subject is likely to respond or is responsive to the anti-SMAD7 therapy. In some embodiments of the invention, the concentration of CRP in the sample is less than about 3.0 mg/liter, about 2.0 mg/liter, about 1.0 mg/liter, or about 0.1 mg/liter, indicating that the subject is responsive or likely to respond to the anti-SMAD7 therapy. In a preferred embodiment, the concentration of CRP in the sample is less than about 3.0 mg/liter, indicating that the subject is responsive or likely to respond to the anti-SMAD7 therapy.

Similarly, the value of the control level of CRP is used to determine whether a subject is likely to respond or is responsive to the anti-SMAD7 therapy by comparing it to the concentration of CRP in the sample taken from the subject. In some embodiments of the invention, the control level of CRP is greater than or equal to about 2.5 mg/liter, about 3.0 mg/liter, about 3.5 mg/liter, about 4.0 mg/liter, about 5.0 mg/liter, or higher. In a preferred embodiment, the control level of CRP is greater than about 3.0 mg/liter. Furthermore, in some embodiments of the invention, the control level of CRP is a baseline level of CRP obtained from the patient prior to administration of at least one anti-SMAD7 therapy or obtained immediately after the administration of at least one anti-SMAD7 therapy. In some embodiments, the control level of CRP may be obtained from the patient immediately before, about 1 hour before, about 1 day before, about 1 week before, about 2 weeks before, about 3 weeks before, about 1 month before, about 1 year before, or longer, prior to administration of at least one anti-SMAD7 therapy.

The contemplated methods for monitoring responsiveness of a subject with IBD to treatment with an anti-SMAD7 therapy allow the person of skill to determine whether a subject will enter remission or is likely to enter remission—in some embodiments defined as maintaining a CDAI score of less than 150 for at least two weeks—based on the discovery of the relationship described herein between responsiveness to anti-SMAD7 therapy treatment in a subject with IBD and circulating CRP levels. Similarly, some embodiments of the contemplated methods of treatment and methods of reducing CRP levels in a subject with IBD allow the person of skill to determine whether a subject will enter remission or is likely to enter remission based on this discovery. In some embodiments of the invention, a decrease in the amount of CRP in the sample obtained from the subject indicates that the subject is likely to enter remission or has entered remission. The decrease in the amount of CRP in the sample obtained from the subject may be determined by comparing the concentration of CRP in a sample taken from the subject to either a control level of CRP and/or the circulating concentration of CRP in the subject measured after a step (a) of administering at least one anti-SMAD7 therapy to the subject. For instance, a decrease in CRP concentration in the sample below a control level of 3 mg/liter indicates that the subject is likely to enter remission or has entered remission.

The invention also establishes a correlation between changes in circulating CRP levels in a sample taken from a subject and CDAI score, such that a decrease in circulating CRP levels coincides with a CDAI score, for example, a CDAI score of less than about 150. The decrease in the amount of CRP in the sample obtained from the subject may be determined by comparing the concentration of CRP in a sample taken from the subject to either a control level of CRP and/or the circulating concentration of CRP in the subject measured after a step (a) of administering at least one anti-SMAD7 therapy to the subject. In some embodiments, a decrease in the amount of CRP in the sample coincides with a CDAI score of less than 170, less than 160, less than 150, less than 140, less than 130, less than 120, less than 110, less than 100, or lower in the subject. In a preferred embodiment, the decrease in the amount of CRP in the sample coincides with a CDAI score of less than 150 in the subject. In a preferred embodiment, the CDAI score of less than 150 coincides with a decrease in CRP levels where a baseline CRP level is greater than 3.0 mg/liter and the decreased CRP level is below 3.0 mg/liter.

The invention also establishes a correlation between changes in circulating CRP levels in a sample taken from a subject and the Patient Reported Outcome 2 (PRO-2) test, such that a decrease in circulating CRP levels coincides with a PRO-2 score, for example, a PRO-2 score of ≤8 or a ≥50% decrease of a PRO-2 score from baseline. The decrease in the amount of CRP in the sample obtained from the subject may be determined by comparing the concentration of CRP in a sample taken from the subject to either a control level of CRP and/or the circulating concentration of CRP in the subject measured after a step (a) of administering at least one anti-SMAD7 therapy or anti-CRP therapy to the subject. In some embodiments, a decrease in the amount of CRP in the sample coincides with a PRO-2 score of <14, <12, <10, <8, <6, <4, or <2 points in a subject. In a preferred embodiment, the decrease in the amount of CRP in the sample coincides with a PRO-2 score of ≤8 in a subject. In a preferred embodiment, the PRO-2 score of ≤8 coincides with a decrease in CRP levels where a baseline CRP level is greater than 3.0 mg/liter and the decreased CRP level is below 3.0 mg/liter.

The invention also establishes a correlation between changes in circulating CRP levels in a sample taken from a subject and the Simple Endoscopic Score for Crohn's Disease (SES-CD), such that a decrease in circulating CRP levels coincides with a SES-CD, for example, a SES-CD of ≤2 (e.g., SES-CD=0) or a SES-CD of ≥50% decrease from baseline. The decrease in the amount of CRP in the sample obtained from the subject may be determined by comparing the concentration of CRP in a sample taken from the subject to either a control level of CRP and/or the circulating concentration of CRP in the subject measured after a step (a) of administering at least one anti-SMAD7 therapy or anti-CRP therapy to the subject. In some embodiments, a decrease in the amount of CRP in the sample coincides with a SES-CD of ≤5, ≤4, ≤3, ≤2, ≤1, or 0 in a subject. In a preferred embodiment, the decrease in the amount of CRP in the sample coincides with a SES-CD of ≤2 or SES-CD of 0 in a subject. In a preferred embodiment, the SES-CD of ≤2 or SES-CD of 0 coincides with a decrease in CRP levels where a baseline CRP level is greater than 3.0 mg/liter and the decreased CRP level is below 3.0 mg/liter.

The claimed invention also provides temporal parameters for defining when an observed CDAI score in a subject already treated, being treated with, or being evaluated for further treatment with an anti-SMAD7 therapy is helpful for determining whether a subject is responsive to treatment with an anti-SMAD7 therapy. For example, in some embodiments, a CDAI score that coincides with a decrease in the amount of CRP in a sample, for example, a CDAI score of less than 150, is maintained for at least 1 day, 1 week, 2 weeks, or longer in the subject.

Additionally, in some embodiments of the invention a CDAI score (e.g., a CDAI score of less than 150) in a subject that coincides with a decrease in the amount of CRP in a sample from the subject can be observed in relation to the end of treatment with an anti-SMAD7 therapy. For example, in some embodiments of the invention, a CDAI score of less than 150 in a subject that coincides with a decrease in the amount of CRP in a sample from the subject is observable while being treated, immediately after stopping treatment, or about 1 day, about 1 week, about 2 weeks, about 1 month, about 10 weeks, about 1 year, or longer after stopping treatment with the anti-SMAD7 therapy. In a particular embodiment, the CDAI score of less than 150 in a subject that coincides with a decrease in the amount of CRP in a sample from the subject is observable at both about 1 day and about 2 weeks after stopping treatment with the anti-SMAD7 therapy. In some embodiments of the invention, a high baseline CRP level (i.e., a CRP level greater than 3.0 mg/liter) indicates that the subject is likely to benefit or be responsive to treatment with an anti-SMAD7 therapy such that treatment will result in a CDAI score of less than 150 in the patient.

The claimed invention also establishes a correlation between changes in circulating CRP levels in a sample taken from a subject and changes in CDAI score, such that a decrease in circulating CRP levels coincides with a decrease in CDAI score. The decrease in the amount of CRP in the sample obtained from the subject may be determined by comparing the concentration of CRP in a sample taken from the subject to either a control level of CRP and/or the circulating concentration of CRP in the subject measured after a step (a) of administering at least one anti-SMAD7 therapy to the subject. The decrease in CDAI score may be determined by comparing the CDAI score in a subject being treated or who has been treated with an anti-SMAD7 therapy, to a CDAI score in a subject who has been treated, is currently being treated, or is being evaluated for treatment with the anti-SMAD7 therapy. In some embodiments, the decrease in the amount of CRP in the sample taken from the subject coincides with a decrease in CDAI score of about 40, about 50, about 60, about 70, about 80, about 90, about 100, about 110, about 120, or about 130 in the subject. In some embodiments, the decrease in the amount of CRP in the sample taken from the subject coincides with a decrease in CDAI score of about 40 to about 130, about 50 to about 120, about 60 to about 110, about 70 to about 120, or about 60 to about 100 in the subject. In a preferred embodiment, the decrease in the amount of CRP in the sample taken from the subject coincides with a decrease in CDAI score of about 70 to about 100 in the subject.

Additionally, in some embodiments of the invention the decrease in CDAI score (e.g., a decrease in CDAI score of about 70 to about 100) in a subject that coincides with a decrease in the amount of CRP in a sample from the subject can be observed in relation to the end of treatment with an anti-SMAD7 therapy. For example, in some embodiments of the invention, the decrease in CDAI score in a subject that coincides with a decrease in the amount of CRP in a sample from the subject is observable while the subject is being treated with an anti-SMAD7 therapy, immediately after stopping treatment with an anti-SMAD7 therapy, or about 1 day, about 1 week, about 2 weeks, about 4 weeks, about 8 weeks, or longer after stopping treatment with the anti-SMAD7 therapy. In preferred embodiments, the decrease in CDAI score in a subject that coincides with a decrease in the amount of CRP in a sample from the subject is observable at least about 1 day or about 2 weeks after stopping treatment with the anti-SMAD7 therapy.

Alternative parameters for determining responsiveness of a subject with IBD to treatment with an anti-SMAD7 therapy or determining whether a subject will enter remission or is likely to enter remission include parameters such as CDAI components (e.g. abdominal pain, stool frequency), Patient Report Outcome test scores (e.g. PRO-2 test score), and mucosal healing (e.g. using Simple Endoscopic Score for Crohn's Disease (SES-CD)).

The claimed invention also provides methods of determining CRP concentration in order to determine whether treatment with an anti-SMAD7 therapy is effective in a subject or to determine whether the subject is responsive to or is likely to respond to treatment with an anti-SMAD7 therapy. The concentration of CRP may be determined by immunochemistry and/or by nucleotide analysis. Methods of determining CRP concentration by immunochemistry include, but are not limited to, Western blotting, ELISA, and immunostaining methods. In some embodiments, a method of determining CRP concentration by immunochemistry is performed using an anti-CRP antibody. Methods of determining CRP concentration by immunochemistry may also involve the use of buffers, blocking reagents, unconjugated primary antibodies, and primary and/or secondary antibodies conjugated to tags that allow for antibody detection, such as fluorescent probes or substrate-specific enzymes.

Methods of determining CRP concentration by nucleotide analysis include, but are not limited to, methods of analyzing CRP mRNA transcript levels such as Northern blotting and polymerase chain reaction methods, for example, quantitative polymerase chain reaction methods. Nucleotide analysis may be performed using an oligonucleotide probe that binds a CRP nucleotide sequence or a pair of oligonucleotide primers capable of amplifying a CRP sequence via a polymerase chain reaction, for example, by a quantitative polymerase chain reaction. Oligonucleotide probes and oligonucleotide primers may be linked to a detectable tag, such as, for example, a fluorescent tag. In determining CRP concentration by nucleotide analysis, the practitioner may evaluate CRP mRNA transcript concentration in a sample. Alternatively, in determining CRP concentration by nucleotide analysis, the practitioner may establish a correlation between CRP mRNA transcript abundance and CRP protein abundance in order to extrapolate CRP protein concentration based on a measure of CRP mRNA transcript abundance.

Methods of the claimed invention include steps that may be carried out in vitro. For instance, in various embodiments of the invention, the steps of measuring the circulating CRP concentration in the subject, determining the concentration of CRP in a sample, determining the control level of CRP, and/or determining CDAI score or taking measurements necessary to determine CDAI score may be carried out in vitro. For example, the concentration of CRP in a sample may be determined by performing immunochemistry or nucleotide analysis on the sample in vitro. Alternatively, in some embodiments of the invention, the steps of measuring the circulating CRP concentration in the subject, determining the concentration of CRP in a sample, determining the control level of CRP, and/or determining CDAI score or taking measurements necessary to determine CDAI score may be carried out in vivo.

The invention provides methods that involve administration of an anti-SMAD7 therapy to a subject. In one embodiment, the anti-SMAD7 therapy may be administered by one or several routes, including orally, topically, parenterally, e.g., by subcutaneous injection, by inhalation spray, or rectally. The term parenteral as used herein includes subcutaneous injections, intrapancreatic administration, intravenous, intramuscular, intraperitoneal, intrasternal injection or infusion techniques. In a preferred embodiment, the anti-SMAD7 therapy may be administered orally to a subject.

In some embodiments, the anti-SMAD7 therapy is an anti-SMAD7 antisense therapy. In a particular embodiment, the antisense therapy comprises an anti-SMAD7 antisense oligonucleotide represented by SEQ ID NO: 1.

In some embodiments, the anti-SMAD7 therapy may be in the form of a pharmaceutical tablet formulation for oral administration of an antisense oligonucleotide comprising an intra-granular phase, wherein the intra-granular phase includes an antisense oligonucleotide such as that represented by SEQ ID NO: 1, or a pharmaceutically acceptable salt thereof (such as a sodium salt), and a pharmaceutically acceptable filler, and which may also include an extra-granular phase that may include a pharmaceutically acceptable excipient such as a disintegrant. Contemplated oligonucleotides include those represented by SEQ ID NO: 1, wherein at least one, or in certain embodiments, all of the internucleoside linkages are O,O-linked phosphorothioates. The anti-SMAD7 therapy in the form of a pharmaceutical tablet may further comprise an enteric coating, for example, an enteric coating comprising an ethylacrylate-methacrylic acid copolymer. Such a tablet may, for example, include a filler, a disintegrant, and/or a lubricant. For example, an oral dose form, such as a tablet, may comprise about 35 mg to about 500 mg of an antisense oligonucleotide, e.g., 40 mg of an oligonucleotide represented by SEQ ID NO: 1 or a pharmaceutically acceptable salt thereof. It is contemplated that the pharmaceutical tablet formulation may be used in methods for treating CD, UC, and IBD by administering it to the patient in need thereof. Upon orally administering the pharmaceutical formulation, or a tablet or oral dosage form, to a patient, the pharmaceutical formulation, tablet, or oral dosage form may be substantially delivered to the terminal ileum and/or right colon of the patient.

It is contemplated that any of the methods described herein may be used to treat a subject with IBD or to evaluate responsiveness or likeliness of responsiveness to an anti-SMAD7 therapy in a subject with IBD. Furthermore, in certain embodiments the IBD is CD or UC. Furthermore, the subject referred to in any of the methods disclosed herein may be a human subject.

In some embodiments of the invention, the anti-SMAD7 therapy may be administered following or concurrently with other treatments, for instance, but not limited to, an immunomodulator and/or mesalamine. In some embodiments, the anti-SMAD7 therapy may be administered following or concurrently with a steroid as well as an immunomodulator and/or mesalamine. The anti-SMAD7 therapy may be administered following or concurrently with any combination of these treatments. For instance, the anti-SMAD7 therapy may be administered following or concurrently with only a steroid, only an immunomodulator, only mesalamine, a steroid and an immunomodulator, a steroid and mesalamine, or an immunomodulator and mesalamine.

The invention also provides a method of treating IBD, comprising administering to a patient an anti-SMAD7 therapy following or concurrently with an immunomodulator and/or mesalamine. In some embodiments of the invention, a steroid may be administered following or concurrently with the anti-SMAD7 therapy and an immunomodulator and/or mesalamine. In some embodiments of the method of treating IBD, comprising administering to a patient an anti-SMAD7 therapy following or concurrently with a steroid, an immunomodulator, and/or mesalamine, the anti-SMAD7 therapy is administered orally. In some embodiments of the method of treating IBD, comprising administering to a patient an anti-SMAD7 therapy following or concurrently with a steroid, an immunomodulator, and/or mesalamine, all of the therapy components (i.e., steroid, immunomodulator, and/or mesalamine) are administered orally. In other embodiments, the anti-SMAD7 therapy is administered orally, and the immunomodulator and/or mesalamine is administered via a different route. In some embodiments, for instance, the immunomodulator and/or mesalamine route of administration is topical, parenteral, by inhalation spray, or rectal.

In some embodiments of the invention that provide a method of treating IBD, administration of any of the above-contemplated combination therapies results in benefits to the patient. For instance, in various embodiments of the invention, the method results in the patient entering remission, the method results in a CDAI score of less than 150 in the subject, the method results in a decrease in CDAI score of about 70 to about 100 in the subject, and/or the method results in circulating CRP levels of less than about 3 mg/liter.

The invention also establishes a correlation between treatment of IBD involving administration of an anti-SMAD7 therapy following or concurrently with other components (e.g., an immunomodulator, mesalamine, and/or a steroid) and CDAI score, such that administration coincides with a CDAI score, for example, a CDAI score of less than about 150 in the subject. In some embodiments, the method results in a CDAI score of less than 170, less than 160, less than 150, less than 140, less than 130, less than 120, less than 110, less than 100, or lower in the subject. In a preferred embodiment, the method results in a CDAI score of less than 150 in the subject.

The claimed invention also reveals a correlation between temporal parameters in observed CDAI score and treatment with an anti-SMAD7 therapy following or concurrently with other components (e.g., an immunomodulator, mesalamine, and/or a steroid). For example, in some embodiments, the method results in a particular CDAI score, for example, a CDAI score of less than 150, which is maintained for at least 1 day, at least 1 week, at least 2 weeks, or longer in the subject.

Additionally, in some embodiments of the invention a CDAI score (e.g., a CDAI score of less than 150) in a subject can be observed in relation to the end of treatment with an anti-SMAD7 therapy following or concurrently with other components (e.g., an immunomodulator, mesalamine, and/ or a steroid). For example, in some embodiments of the invention, a CDAI score of less than 150 in a subject is observable while being treated, immediately after stopping treatment, or about 1 day, about 1 week, about 2 weeks, about 1 month, about 10 weeks, about 1 year, or longer after stopping treatment with the anti-SMAD7 therapy in combination with other components. In a particular embodiment, the CDAI score of less than 150 in a subject is observable at both about 1 day and about 2 weeks after stopping treatment with the anti-SMAD7 therapy following or concurrently with other components.

The claimed invention also establishes a correlation between treatment with an anti-SMAD7 therapy following or concurrently with other components (e.g., an immunomodulator, mesalamine, and/or a steroid) and changes in CDAI score, such that treatment coincides with a decrease in CDAI score. The decrease in CDAI score may be determined by comparing the CDAI score in a subject being treated or who has been treated with an anti-SMAD7 therapy following or concurrently with other components, to a CDAI score in a subject who has been treated, is currently being treated, or is being evaluated for treatment with the anti-SMAD7 therapy. In some embodiments, the method results in a decrease in CDAI score of about 40, about 50, about 60, about 70, about 80, about 90, about 100, about 110, about 120, or about 130 in the subject. In some embodiments, the method results in a decrease in CDAI score of about 40 to about 130, about 50 to about 120, about 60 to about 110, about 70 to about 120, or about 60 to about 100 in the subject. In a preferred embodiment, the method results in a decrease in CDAI score of about 70 to about 100 in the subject.

Additionally, in some embodiments of the invention the decrease in CDAI score (e.g., a decrease in CDAI score of about 70 to about 100) in a subject that results from treatment with an anti-SMAD7 therapy following or concurrently with other components (e.g., an immunomodulator, mesalamine, and/or a steroid) can be observed in relation to the end of that treatment. For example, in some embodiments of the invention, the decrease in CDAI score in a subject that results from the method of treatment is observable while the subject is being treated, immediately after stopping treatment, or about 1 day, about 1 week, about 2 weeks, about 4 weeks, about 8 weeks, or longer after stopping treatment. In preferred embodiments, the decrease in CDAI score in a subject that results from the method of treatment is observable at least about 1 day or about 2 weeks after stopping treatment.

The invention also provides a kit with reagents for measuring CRP levels and detailed instructions for measuring a CDAI Score. In certain embodiments of the invention, the reagents for measuring CRP levels are selected from the group consisting of an anti-CRP antibody, oligonucleotide probes that bind a CRP nucleotide sequence, and oligonucleotide primers capable of binding to and amplifying a CRP nucleotide sequence via a polymerase chain reaction. In some embodiments, the kit may include at least one of buffers, reagents and detailed instructions for measuring CRP levels. Furthermore, in some embodiments, the anti-CRP antibody of the kit may be a primary antibody against a CRP protein, and the kit may optionally also include a secondary antibody conjugated to a reporter enzyme, buffers, reagents and detailed instructions for measuring CRP levels in a sample using immunochemistry and/or a polymerase chain reaction.

In another aspect, the invention provides methods for treating or managing inflammatory bowel disease in a patient having IBD. In one embodiment, the method includes the following steps: (a) administering to the patient an initial dose of a SMAD7 antisense oligonucleotide; (b) analyzing the level of CRP in the patient; and (c) if the level of CRP is above normal levels of CRP, then administering to the patient a subsequent dose that is grate than or equal to the initial dose. Alternatively, if in step (c), the level of CRP is below normal levels of CRP as determined in step (b), then step (c) includes administering to the patient a subsequent dose that is equal to or smaller than the initial dose.

In another aspect of the invention, the invention provides methods for treating or managing IBD in a patient having IBD with respect to administration of an initial dose of a SMAD7 antisense oligonucleotide. In one embodiment, the invention provides a method for treating or managing IBD in a patient having IBD, where the method includes the following steps: (a) analyzing the level of CRP in the patient; and (b) if the level of CRP is above a threshold level of CRP, then administering to the patient an initial dose of a SMAD7 antisense oligonucleotide. Additionally, the method may further include the steps of: (c) analyzing the level of CRP in the patient after said administering step, i.e., step (b); and (d) if the level of CRP is above normal levels of CRP, then administering to the patient a subsequent dose that is greater than or equal to the initial dose. Alternatively, if in step (d), the level of CRP is below normal levels of CRP, as determined in step (c), then step (d) includes administering to the patient a subsequent dose that is equal to or smaller than the initial dose. In some embodiments, if the level of CRP is above normal levels of CRP, then the method includes the step of administering to the patient a subsequent dose that is greater than the initial dose. In some embodiments, if the level of CRP is below normal levels of CRP, then the method includes the step of administering to the patient a subsequent dose that is smaller than the initial dose. In some instances, if the subsequent dose administered in step (d) is equal to or greater than the maximum tolerated dose (MTD), then the method includes the step of terminating the treatment.

The level of CRP may be analyzed at varying time points following an administering step (b). For instance, in some embodiments, following an administering step (b), the level of CRP is analyzed at least 1 day, at least 3 days, at least 5 days, at least 1 week, at least 2 weeks, at least 3 weeks, at least 1 month, at least 2 months, at least 4 months, or at least 6 months after said administration step. In some embodiments, the level of CRP is analyzed immediately after said administration step. In yet other embodiments, the level of CRP is analyzed about 7 days, about 10 days, about 15 days, about 20 days, about 25 days, or about 28 days after said administration step.

Normal levels of CRP may be determined based on numerical reference values or with respect to levels of CRP in a healthy control group. For instance, in some embodiments, normal levels of CRP are about 0.01 mg/L, about 0.05 mg/L, about 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, about 1.0 mg/L, about 1.5 mg/L, about 2.0 mg/L, about 2.5 mg/L, or about 3.0 mg/L. In other embodiments of the invention, normal levels of CRP are defined as median levels of CRP in a healthy control group. A healthy control group may be defined based on various criteria related to genetic background, habits, and physical attributes matched to the same set of criteria in the patient. For instance, in some embodiments, the healthy control group and the patient having IBD are matched with respect to age, gender, ethnic origin, smoking habits, dietary habits, body-mass index (BMI), recreational drug use, medical drug use, drug use related to IBD, and/or exercise habits. Other factors that can be matched between the patient and control group include, but are not limited to, clinical criteria (e.g., CDAI score, Mayo score, severity of IBD-related symptoms), metabolism, IBD patient's personal disease history, genetic factors, IBD patient's family disease history, exposure to environmental factors (e.g., pollutants, toxins, allergens), and life-style (e.g., urban, suburban, or rural place of work and/or domicile).

Differences in patient CRP levels and threshold CRP levels are indicative of a patient's potential responsiveness to anti-SMAD7 therapy. For example, threshold CRP levels that are elevated relative to a normal CRP level indicate that a patient may be responsive to anti-SMAD7 therapy. Threshold levels of CRP can be established using different criteria. In some embodiments, the threshold level of CRP is determined with respect to normal CRP levels, for example median CRP levels, in a control group. Control groups may be comprised of healthy/normal subjects (e.g., a healthy control group) or groups of IBD patients. For instance, in some embodiments, a CRP threshold level is at least 2-fold, at least 3-fold, at least 5-fold, at least 8-fold, at least 10-fold, at least 20-fold, at least 30-fold, at least 50-fold, at least 80-fold, or at least 100-fold above normal levels. In other embodiments, the CRP threshold level is in the $50^{th}$ percentile, $60^{th}$ percentile, $70^{th}$ percentile, $80^{th}$ percentile or $90^{th}$ percentile of CRP levels with respect to CRP levels, for example median CRP levels, in a group of IBD patients. In some embodiments, the level of CRP is below 3 mg/L. Additionally, in some embodiments, the threshold level of CRP is more than 0.5 mg/L, more than 1.0 mg/L, more than 1.5 mg/L, more than 2.0 mg/L, more than 2.5 mg/L, more than 3.0 mg/L, more than 3.5 mg/L, more than 4.0 mg/L, more than 4.5 mg/L, more than 5.0 mg/L, more than 7.5 mg/L, or more than 10 mg/L. In some embodiments, the threshold level of CRP is about 0.5 mg/L, about 1.0 mg/L, about 1.5 mg/L, about 2.0 mg/L, about 2.5 mg/L, about 3.0 mg/L, about 3.5 mg/L, about 4.0 mg/L, about 4.5 mg/L, about 5.0 mg/L, about 7.5 mg/L, or about 10 mg/L. In some embodiments, the level of CRP is between 0.5 mg/L and 3 mg/L, between 1 mg/L and 3 mg/L, between 1.5 mg/L and 3 mg/L, between 2 mg/L and 3 mg/L, or between 2.5 mg/L and 3 mg/L.

In various embodiments of the invention, the initial dose of a SMAD7 antisense oligonucleotide administered to a patient having IBD may vary. For instance, in some embodiments, the initial dose of a SMAD7 antisense oligonucleotide administered to a patient having IBD is less than 500 mg/day, less than 400 mg/day, less than 300 mg/day, less than 200 mg/day, less than 100 mg/day, less than 90 mg/day, less than 80 mg/day, less than 70 mg/day, less than 60 mg/day, less than 50 mg/day, less than 40 mg/day, less than 30 mg/day, less than 20 mg/day, or less than 10 mg/day. Alternatively, in other embodiments, the initial dose is at least 1 mg/day, at least 5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, at least 100 mg/day, at least 200 mg/day, at least 300 mg/day, at least 400 mg/day, or at least 500 mg/day. In yet other embodiments, the initial dose is about 1 mg/day, about 5 mg/day, about 10 mg/day, about 20 mg/day, about 30 mg/day, about 40 mg/day, about 50 mg/day, about 60 mg/day, about 70 mg/day, about 80 mg/day, about 90 mg/day, about 100 mg/day, about 200 mg/day, about 300 mg/day, about 400 mg/day, or about 500 mg/day. In some embodiments, the initial dose is 5 mg/day, 10 mg/day, 20 mg/day, 30 mg/day, 40 mg/day, 50 mg/day, 60 mg/day, 70 mg/day, 80 mg/day, 90 mg/day, 100 mg/day, 110 mg/day, 120 mg/day, 130 mg/day, 140 mg/day, 150 mg/day, 160 mg/day, 170 mg/day, 180 mg/day, 190 mg/day, or 200 mg/day.

In some embodiments of the invention, after analyzing the level of CRP in the patient in a step (b) or (c), if the level of CRP is above normal levels of CRP, then the method may include the step of administering to the patient a subsequent dose that is greater than the initial dose. In some embodiments, after analyzing the level of CRP in the patient in a step (b) or (c), if the level of CRP is below normal levels of CRP, then the method may include the step of administering to the patient a subsequent dose that is smaller than the initial dose.

The invention also provides a method for determining the level of a subsequent dose of SMAD7 antisense oligonucleotide with respect to an initial dose of SMAD7 antisense oligonucleotide based on levels of CRP in a patient having IBD. For instance, in embodiments of the invention described herein, if CRP levels in a patient having IBD are above normal levels following an initial administration step (a) or (b), the subsequent dose administered in a step (c) or (d) is at least about 5 mg/day, about 10 mg/day, at least about 20 mg/day, at least about 30 mg/day, at least about 40 mg/day, at least about 50 mg/day, at least about 60 mg/day, at least about 70 mg/day, at least about 80 mg/day, at least about 90 mg/day, at least about 100 mg/day, at least about 110 mg/day, at least about 120 mg/day, at least about 130 mg/day, at least about 140 mg/day, at least about 150 mg/day, at least about 160 mg/day, at least about 170 mg/day, at least about 180 mg/day, at least about 190 mg/day, or at least about 200 mg/day greater than the initial dose.

Alternatively, in some embodiments, if CRP levels in a patient having IBD are below normal levels following an initial administration step (a) or (b), the subsequent dose administered in a step (c) or (d) is at least about 5 mg/day, at least about 10 mg/day, at least about 20 mg/day, at least about 30 mg/day, at least about 40 mg/day, at least about 50 mg/day, at least about 60 mg/day, at least about 70 mg/day, at least about 80 mg/day, at least about 90 mg/day, or at least about 100 mg/day smaller than the initial dose. Furthermore, in some embodiments, the initial dose administered in an initial administration step (a) or (b) is between about 10 mg/day and 100 mg/day, about 5 mg/day and 200 mg/day, about 10 mg/day and 50 mg/day, about 50 mg/day and 100 mg/day, and about 100 mg/day and about 200 mg/day, and the subsequent dose administered in a step (c) or (d) is between about 30 mg/day and 200 mg/day, about 5 mg/day and 30 mg/day, about 20 mg/day and 50 mg/day, about 50 mg/day and 100 mg/day, and about 100 mg/day and 200 mg/day.

The invention also provides methods for modulating treatment with a SMAD7 antisense oligonucleotide in a patient with IBD based on a comparison of relative levels of CRP in a patient before and after an initial administering step. The method includes the following steps: (a) analyzing the level of CRP in the patient; and (b) if the level of CRP is above normal levels of CRP, then administering to the patient an initial dose of a SMAD7 antisense oligonucleotide; (c) analyzing the level of CRP in the patient after said administering step; and (d) if the level of CRP is lower after said administration step than the level of CRP before said administration step, then administering to the patient a subsequent dose that is the same as the initial dose or smaller than the initial dose. Alternatively, in step (d) if the level of CRP is unchanged or increased after said administration step (i.e., step (b)) compared to the level of CRP before said administration step, then step (d) includes administering to the patient a subsequent dose that is greater than the initial dose or terminating the treatment. Alternatively, in step (d) if the patient is in clinical remission and the level of CRP is unchanged or increased after said administration step (i.e., step (b)) compared to the level of CRP before said administration step, then step (d) includes terminating the treatment.

According to methods of the invention, a change in CRP levels observed after an initial administration step (of SMAD7 antisense oligonucleotide) compared to CRP levels prior to the administration step can be compared, for example, as a change in percent of CRP levels, to determine the amount of a subsequent dose of SMAD7 antisense oligonucleotide to be administered to a patient with IBD. For example, in some embodiments, if the level of CRP is at least 5%, at least 10%, at least 20%, at least 30%, at least 40%, at least 50%, at least 70%, at least 80%, at least 90%, or at least 95% decreased after said administration step (e.g., an administration step (b)) compared to the level of CRP before said administration step, then the method includes a step (e.g., an administration step (d)) of administering to the patient a subsequent dose that is the same as the initial dose or smaller than the initial dose.

The invention also provides methods for determining the probability that a patient having IBD will experience clinical remission following treatment with a SMAD7 antisense oligonucleotide based on a comparison of CRP levels, for example, based on a comparison of percent change in CRP levels before and after treatment with a SMAD7 antisense oligonucleotide. For example, in some embodiments, the methods described herein further comprise the step of determining that the patient having IBD has a greater than 10%, greater than 20%, greater than 30%, greater than 40%, greater than 50%, greater than 60%, greater than 70%, greater than 80%, greater than 90% or greater than 100% chance of experiencing clinical remission of the IBD for a time period of at least 1 week, at least 2 weeks, at least 3 weeks, at least 4 weeks, at least 6 weeks or at least 8 weeks, if the level of CRP after an administering step (e.g., an administering step (b)) is at least 5%, at least 10%, at least 20%, at least 30%, at least 40%, at least 50%, at least 60%, at least 70%, at least 80%, at least 90%, or at least 95% decreased compared to the level of CRP before the administration step.

Clinical remission, as described herein, may be determined by comparison to a reference value, for example, a Crohn's Disease Activity Index (CDAI). In some embodiments of the invention, clinical remission in a patient having IBD is indicated by a CDAI score of less than 150 (CDAI ≤150).

In some embodiments of the invention, clinical remission or a patient CDAI score may be observed at a given time point or within a given time frame with respect to administration of the SMAD7 antisense oligonucleotide. For example, in some embodiments, clinical remission is observed about one day, about 3 days, about one week, about two weeks, about three weeks, about four weeks, about six weeks, about eight weeks, or about 10 weeks after an administration step (for example, an administration step (b)) and maintained for a period of at least 3 days, at least 1 week, at least 2 weeks, at least 3 weeks, at least 4 weeks, at least 6 weeks at least 8 weeks, or at least 10 weeks. Similarly, some embodiments of the invention include a method of determining that the patient having IBD has a chance of experiencing clinical remission of IBD, where the patient having IBD had a CDAI of between about 220 and about 400, about 150 and about 200, about 200 and about 250, about 250 and about 300, about 300 and about 350, about 350 and about 400, about 400 and about 450, or greater than about 450 one week prior to an administration step (for example, an administration step (b)).

In some embodiments, the invention provides a method of treating or managing IBD in a patient with above normal levels of CRP, where the method includes administering to the patient a dose of SMAD7 antisense oligonucleotide. Furthermore, in some embodiments, the invention provides methods for treating or managing IBD in a patient who has above normal CRP levels following administration of a dose of a SMAD7 antisense oligonucleotide, where the patient is administered a further dose of the SMAD7 antisense oligonucleotide that is greater than or equal to the prior dose. Similarly, in some embodiments, the invention provides methods for treating or managing IBD in a patient having IBD who has below normal CRP levels following administration of a dose of SMAD7 antisense oligonucleotide. In the latter case, the method will include administering to the patient a further dose of the SMAD7 antisense oligonucleotide that is less than or equal to the prior dose. In some embodiments, administration of the SMAD7 antisense oligonucleotide to the patient is repeated until the levels of a biomarker, e.g., IL8, CRP, or TNFα, reach normal levels; the patient achieves a CDAI score of less than 150; or the patient achieves clinical remission.

The invention also provides methods of treating or managing IBD in a patient having above normal levels of CRP, where the amount of a SMAD7 antisense oligonucleotide administered to the patient is increased until CRP levels in the patient decrease. In such embodiments, levels of SMAD7 antisense oligonucleotide administered to the patient may be increased until the level of CRP in the patient decreases to about a normal level of CRP or a below normal level of CRP.

In some embodiments, the invention provides a method of monitoring the treatment or management of IBD in a patient with IBD, that includes analyzing CRP levels in the patient following each SMAD7 antisense oligonucleotide administration. Utilizing these methods, the absence of a decrease in CRP levels indicates that the treatment or management is not effective. In such embodiments, CRP levels may be analyzed one time or multiple times, for instance, two times, three times, four times, about five times, about 10 times, about 15 times, about 20 times, or about 30 times, after each administration of SMAD7 antisense oligonucleotide. Furthermore, the timing of the measurement of CRP levels may vary with respect to the time of SMAD7 oligonucleotide administration such that CRP levels may be analyzed immediately after, about 1 hour after, about 3 hours after, about 6 hours after, about 12 hours after, about 1 day after, about 3 days after, about 1 week after, about 2 weeks after, and/or about 1 month after SMAD7 antisense oligonucleotide administration.

In order to determine levels of a biomarker or analyte, for example, CRP, in a patient having IBD using the methods described herein, a sample may be obtained from the patient. Therefore, in some embodiments of the invention, the level of CRP in the patient having IBD is determined in a sample obtained from the patient having IBD. Analytes other than or in addition to CRP, for example, but not limited to tumor necrosis factor alpha (TNFα) and Interleukin 8 (IL8), may also be determined in methods of the invention. Thus, in some embodiments of the invention, the method includes determining a level, or multiple levels, of one or more additional analytes in the patient having IBD. Analytes of CRP include RNA, DNA, and protein products of or derived from the CRP gene, described by NCBI Reference Sequence: NG_013007.1 Analytes of TNFα include RNA, DNA, and protein products of or derived from the TNFα gene, described by NCBI Reference Sequence: NG_007462.1. Analytes of IL8 include RNA, DNA, and protein products of or derived from the IL8 gene, described by NCBI Reference Sequence: NG_029889.1.

Samples containing analytes of interest, for example, TNFα, CRP, and/or IL8, obtained from the patient having IBD, may include blood, serum, or plasma samples. Samples may also include tissue samples such as, but not limited to, tissue, gastrointestinal, mucosal, submucosal, intestinal, esophageal, ileal, rectal, or lymphatic samples. Levels of analytes of interest in a sample from a patient having IBD may be determined using various assays. For example, in methods of the invention, the level of CRP and/or one or more additional analytes may be determined by immunochemistry, for example, by an enzyme-linked immunosorbent assay (ELISA), or by nucleotide analysis.

Methods of the invention include methods for treating and managing various forms of IBD. For example, the invention includes methods for treating and managing IBD, where the IBD is Crohn's Disease (CD) or ulcerative colitis (UC). The contemplated invention also provides methods for treating different types of patients with IBD, including, for example, but not limited to, IBD patients that are steroid-dependent patients with active CD; and steroid-resistant patients with active CD.

It will be appreciated that the SMAD7 antisense oligonucleotide administered to the patient having IBD in methods of the invention described herein, may be administered by various administration routes. In various embodiments, the SMAD7 antisense oligonucleotide may be administered by one or several routes, including orally, topically, parenterally, e.g., by subcutaneous injection, by inhalation spray, or rectally. The term parenteral as used herein includes subcutaneous injections, intrapancreatic administration, intravenous, intramuscular, intraperitoneal, intrasternal injection or infusion techniques. In a preferred embodiment, the SMAD7 antisense oligonucleotide may be administered orally to the patient having IBD.

The contemplated invention provides methods that include administration of a SMAD7 antisense oligonucleotide capable of targeting SMAD7 RNA for degradation, interfering with RNA splicing or preventing SMAD7 gene expression or protein translation. The contemplated SMAD7 antisense oligonucleotide of the invention may target various regions of the human SMAD7 mRNA for binding. For example, the SMAD7 antisense oligonucleotide may target nucleotides 108-128 of human SMAD7 mRNA (SEQ ID NO: 2). In some embodiments, the SMAD7 antisense oligonucleotide may target nucleotides 403, 233, 294, 295, 296, 298, 299 or 533 of the human SMAD7 sequence (SEQ ID NO: 2). The human SMAD7 mRNA sequence is the sequence of NCBI Reference Sequence: NM_005904.3 (SEQ ID NO: 2).

The sequence of the contemplated SMAD7 antisense oligonucleotide may be selected from multiple sequences capable of targeting SMAD7 RNA. For example, in some embodiments of the invention, the SMAD7 antisense oligonucleotide comprises the nucleotide sequence of SEQ ID NO: 3 (5'-GTCGCCCCTTCTCCCCGCAGC-3'). In some embodiments of the invention, the antisense oligonucleotide is an antisense oligonucleotide phosphorothioate, i.e., an oligonucleotide where at least some of the internucleoside linkages are phosphorothioate linkages, suitable for delivery to cells of a patient. Additionally, antisense oligonucleotides of the invention may include modified nucleotides, for example, nucleotides containing modified bases, for example, as in 5-methyl-2'-deoxycytidine. For example, in some embodiments, the antisense oligonucleotide is an antisense oligonucleotide phosphorothioate against SMAD7 comprising the following sequence: 5'-GTXGCCCCT-TCTCCCXGCAG-3' (SEQ ID NO: 4), wherein X is 5-methyl-2'-deoxycytidine and wherein the internucleoside linkages are phosphorothioate linkages. In some embodiments, the antisense oligonucleotide is an antisense oligonucleotide phosphorothioate against SMAD7 comprising the following sequence: 5'-GTXGCCCCTTCTC-CCXGCAGC-3' (SEQ ID NO: 1), wherein X is a nucleotide comprising 5-methyl-2'-deoxycytidine and wherein the internucleoside linkages are phosphorothioate linkages. In some embodiments, the SMAD7 antisense oligonucleotide may be an antisense oligonucleotide defined by Chemical Abstract Service (CAS) entries, for instance, but not limited to, CAS Registry Number (RN) 1443994-98-6 or of CAS RN 1443994-46-4. In a particular embodiment, the contemplated antisense oligonucleotide is an antisense oligonucleotide comprising SEQ ID NO: 1, wherein each of the 20 internucleoside linkages is an O,O-linked phosphorothioate linkage, referred to herein as "Mongersen."

The present invention is also based on the development of methods for treating patients having IBD using a combination of an antisense therapeutic directed against SMAD7 and one or more further therapeutics. In particular examples, the further therapeutic can be an aminosalicylate, an antibiotic, a corticosteroid, an immunomodulator, or an inflammatory cytokine antagonist. Administration of the combination therapy can result in synergistic benefits, which can lead to improved patient outcome, reduce side effects, allow for lower dosages, or allow less frequent or shorter duration of administration of one or both the therapeutics being administered. Such approaches can also reduce resistance to stand-alone therapies (e.g., steroid resistance).

Accordingly, in one aspect, the invention features a method for treating or managing IBD (e.g., Crohn's Disease (CD) or ulcerative colitis (UC)) in a patient having IBD. The method including administering to the patient a combination of agents that includes a SMAD7 antisense oligonucleotide and one or more additional therapeutic agents, where the agents together are administered in a therapeutically effective amount. In certain embodiments, the combination does not consist of (a) Mongersen and mesalamine, (b) Mongersen and budesonide, (c) Mongersen, mesalamine, and budesonide, or (d) Mongersen and a systemically administered corticosteroid. The one or more additional therapeutic agents can be selected from the group consisting of an aminosalicylate, an antibiotic, a steroid, an anti-inflammatory cytokine agent, and an immunomodulator. The aminosalicylate may be mesalamine or may be selected from the group consisting of 5-aminosalicylic acid, sulfasalazine, balsalazide, olsalazine, and mesalamine.

The antibiotic may be selected from the group consisting of a penicillin, a cephalosporin, a polymyxin, a rifampicin, a quinolone, a sulfonamide, a macrolide, a lincosamide, a tetracycline, an aminoglycoside, a cyclic lipopeptide, a glycylcycline, an oxazolidinone, and a lipiarmycin. In other embodiments, the antibiotic is ciprofloxacin or metronidazole or is selected from the group consisting of erythromycin, clindamycin, gentamicin, meclycycline, sulfacetamide, benzoyl peroxide, ciprofloxacin, rifaximin, rifabutin, clofazimine, clarithromycin, azithromycin, isoniazid, tobramycin, amoxicillin, tetracycline, tinidazole, vancomycin, daptomycin, tigecyclin, linezolid, fidaxomicin, and metronidazole.

The steroid may be a corticosteroid, for example, a corticosteroid selected from the group consisting of budesonide, dexamethasone, betamethasone, tixocortol pivalate, triamcinolone acetonide, mometasone, amcinonide, desonide, fluocinonide, halcinonide, fluocortolone, hydrocortisone, fluticasone propionate, mometasone furotate, prednisone, prednisolone, beclomethasone dipropionate, flunisolide, and methylprednisolone. In particular embodiments, the corticosteroid includes budenoside, dexamethasone, hydrocortisone, methylprednisolone, prednisolone, or prednisone. The patient may be administered an oral dose of less than 40 mg/day or 40 mg/day prednisolone or less than 9 mg/day or 9 mg/day budesonide.

The immunomodulator may be an immunosuppressant, for example, azathioprine, 6-mercaptopurine, cyclosporine A, dactinomycin, anthracycline, mitomycin C, bleomycin, mithramycin, tacrolimus, mitoxanthrone, cyclophosphamide, micophenolate mofetile, rapamycine, minocycline, or methotrexate. The inflammatory cytokine antagonist may be selected from the group consisting of a tumor necrosis factor (TNF) antagonist (e.g., infliximab, adalimumab, certolizumab pegol, golimimab, etanercept, pentoxifylline, and bupropion) and an interleukin 10 (IL10) antagonist.

The patient may be resistant to an IBD therapy or may be steroid-resistant. The SMAD7 antisense oligonucleotide and/or the one or more additional therapeutic agents may be administered orally. The amount of the SMAD7 antisense oligonucleotide administered may be lower than the therapeutically effective amount of the SMAD7 antisense oligonucleotide when administered as a stand-alone therapy. In other embodiments, the amount of the one or more additional agents administered may be lower than the therapeutically effective amount of the one or more additional agents when administered as a stand-alone therapy. The method may further include prior to administering the combination to the patient, administering to the patient for a period of time a therapeutically effective dose of the SMAD7 antisense oligonucleotide alone or of the one or more additional therapeutic agents alone (e.g., where the period of time is sufficient for the patient having IBD to experience a reduction in IBD symptoms or to experience remission).

The SMAD7 antisense oligonucleotide and the one or more additional therapeutic agents may be administered concomitantly (e.g., in combination in a unit dosage form or may be administered in separate unit dosage forms). In other embodiments, the SMAD7 antisense oligonucleotide and the one or more additional therapeutic agents are administered sequentially. In other embodiments, the patient having IBD was undergoing an IBD therapy including the administration of the one or more additional therapeutic agents prior to receiving the first administration of the SMAD7 antisense oligonucleotide. In still other embodiments, the patient having IBD was undergoing an IBD therapy including the administration of the SMAD7 antisense oligonucleotide prior to receiving the first administration of the one or more additional therapeutic agents.

The patient having IBD may be a steroid-dependent patient with active CD or a steroid-resistant patient with active CD.

In certain embodiments, if the patient having IBD experiences disease worsening after receiving the SMAD7 antisense oligonucleotide for a period of time, then a rescue therapy with biologics and/or immunosuppressive drugs (e.g., any described herein) are administered to the patient (e.g., where the period of time is about 1 week, about 2 weeks, about 3 weeks, or about 4 weeks and disease worsening includes an increased score in the Crohn's Disease Activity Index (CDAI) of ≥70 points).

In certain embodiments, if the patient having IBD experiences remission after receiving a dose of the SMAD7 antisense oligonucleotide and a dose of the one or more additional therapeutically active agent for a period of time, then the dose of the SMAD7 or the dose of the additional antisense oligonucleotide is reduced (e.g., by an amount described herein) in subsequent administrations (e.g., where the period of time is about 14 days or about 28 days and remission includes a CDAI ≤150).

The SMAD7 antisense oligonucleotide may be administered to the patient having IBD at a dose of between 10 mg/day to about 300 mg/day (e.g., about 10 mg/day, about 20 mg/day, about 30 mg/day, about 40 mg/day, about 50 mg/day, about 60 mg/day, about 70 mg/day, about 80 mg/day, about 90 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day, about 200 mg/day, about 210 mg/day, about 220 mg/day, about 230 mg/day, about 240 mg/day, about 250 mg/day, about 260 mg/day, about 270 mg/day, about 280 mg/day, about 290 mg/day, or about 300 mg/day). In particular embodiments, the dose is about 40 mg/day, about 80 mg/day, or about 160 mg/day.

The SMAD7 antisense oligonucleotide may be a plurality of SMAD7 antisense oligonucleotides. The SMAD7 antisense oligonucleotide may be administered orally to the patient. The one or more additional therapeutic agents may be administered orally, parenterally, rectally, intravenously, topically, or by inhalation spray. The SMAD7 antisense oligonucleotide may target region 108-128 of human SMAD7 (GCTGCGGGGAGAAGGGGCGAC SEQ ID NO:7). The SMAD7 antisense oligonucleotide may target nucleotides 403, 233, 294, 295, 296, 298, 299 or 533 of human SMAD7 (SEQ ID NO:2; which represents the coding sequence CDS (288-1568) of NM 005904.3, homo sapiens SMAD family member 7 (SMAD7), transcript variant 1, mRNA; the SMAD7 antisense oligonucleotides provided herein can target both a DNA having a nucleotide sequence of SEQ ID NO:2 and a corresponding RNA of SEQ ID NO:2 with Ts replaced by Us). The SMAD7 antisense oligonucleotide may include the nucleotide sequence of SEQ ID NO:3 (5'-GTCGCCCCTTCTCCCCGCAGC-3'). The SMAD7 antisense oligonucleotide may be an antisense oligonucleotide phosphorothioate against SMAD7 including the following sequence: 5'-GTXGCCCCTTCTCCCXGCAG-3' (SEQ ID NO:4) where X is 5-methyl-2'-deoxycytidine and where the internucleoside linkages are phosphorothioate linkages.

The SMAD7 antisense oligonucleotide may be an antisense oligonucleotide phosphorothioate against SMAD7 including the following sequence: 5'-GTXGCCCCTTCTCCCXGCAGC-3' (SEQ ID NO:1) where X is 5-methyl-2'-deoxycytidine and where the internucleoside linkages are phosphorothioate linkages (e.g., an antisense oligonucleotide according to Chemical Abstracts Service Registry Number (CAS RN) 1443994-98-6 or CAS RN 1443994-46-4).

In further aspects, the invention features a system or a kit for the treatment of IBD including a therapeutically effective amount of a SMAD7 antisense oligonucleotide (e.g., any of those described above or herein) and a therapeutically effective amount of one or more additional therapeutic agents (e.g., any of those described above or herein).

In another aspect, the invention features a pharmaceutical composition for the treatment of IBD including a therapeutically effective amount of a SMAD7 antisense oligonucleotide (e.g., any of those described above or herein), therapeutically effective amounts of one or more additional therapeutic agents (e.g., any of those described above or herein), and a pharmaceutically acceptable adjuvant and/or excipient. The pharmaceutical composition may be in a unit dosage form (e.g., a tablet having a methacrylic acid-ethyl acrylate copolymer coating). The pharmaceutical composition may be for oral administration. The pharmaceutical may include an SMAD7 antisense oligonucleotide targets region 108-128 of human SMAD7 (SEQ ID NO:2); an SMAD7 antisense oligonucleotide targets nucleotides 403, 233, 294, 295, 296, 298, 299 or 533 of human SMAD7 (SEQ ID NO:2); an SMAD7 antisense oligonucleotide including the nucleotide sequence of SEQ ID NO:3 (5'-GTCGCCCCT-TCTCCCCGCAGC-3'); an SMAD7 antisense oligonucleotide including the following sequence: 5'-GTXGCCCCT-TCTCCCXGCAG-3' (SEQ ID NO:4) where X is 5-methyl-2'-deoxycytidine and where the internucleoside linkages are phosphorothioate linkages; or an SMAD7 antisense oligonucleotide is an antisense oligonucleotide phosphorothioate against SMAD7 including the following sequence: 5'-GTXGCCCCTTCTCCCXGCAGC-3' (SEQ ID NO:1) where X is 5-methyl-2'-deoxycytidine and where the internucleoside linkages are phosphorothioate linkages (e.g., an antisense oligonucleotide according to Chemical Abstracts Service Registry Number (CAS RN) 1443994-98-6 or CAS RN 1443994-46-4). The one or more additional therapeutic agents may include an aminosalicylate, an antibiotic, a steroid, a tumor necrosis factor (TNF) antagonist, or an immunomodulator.

In certain embodiment of any of the above aspects, the combination of agents is not (i.e., does not consist solely of) or does not include (a) Mongersen and mesalamine, (b) Mongersen and budesonide, (c) Mongersen, mesalamine, and budesonide, and (d) Mongersen and a systemically administered corticosteroid. In other embodiments, the combination of agents does not include a systemically administered corticosteroid, budesonide, or mesalamine.

In certain embodiments of any of the above aspects, the additional therapies are not, or do not include, a steroid or steroids, an immunomodulator or immunomodulators, and/or mesalamine. In some embodiments, the anti-SMAD7 therapy (e.g., Mongersen) is not administered with only a steroid or steroids; only an immunomodulator or immunomodulators; only mesalamine; a steroid or steroids and an immunomodulator or immunomodulators; a steroid or steroids and mesalamine; or an immunomodulator or immunomodulators and mesalamine. In certain embodiments, the immunomodulator is not or does not include azathioprine, mercaptopurine, methotrexate, cyclosporine A, and tacrolimus. In other embodiments, the steroid is not or does not include corticosteroids, for example, is not or does not include prednisone, dexamethasone, hydrocortisone, methylprednisolone, prednisone, and budesonide. In some embodiments, the additional therapy is not or does not include a salicylate or sulfasalazine.

In one aspect of the invention, there is provided an SMAD7 antisense-oligonucleotide for use the treatment or management of inflammatory bowel disease (IBD) in a patient having IBD. Preferably, the method of treatment or management comprises administering to a patient an initial dose of a SMAD7 antisense-oligonucleotide; analyzing the level of CRP in said patient and if the level of CRP is above normal levels of CRP, then administering to the patient a subsequent dose of SMAD7 antisense-oligonucleotide that is greater than or equal to the initial dose of SMAD7 antisense-oligonucleotide or if the level of CRP is below normal levels of CRP, then administering to the patient a subsequent dose of SMAD7 antisense-oligonucleotide that is equal to or smaller than the initial dose of SMAD7 antisense-oligonucleotide. Alternatively, the method of treatment or management comprises analyzing the level of CRP in the patient prior to administration of SMAD7 antisense-oligonucleotide and administering SMAD7 antisense-oligonucleotide if the level of CRP is above a threshold level of CRP. Preferably, if the level of CRP is above normal levels of CRP, the method of treatment or management comprises administering to the patient a subsequence dose that is greater than or equal to the initial dose of SMAD7 antisense-oligonucleotide or if the level of CRP is below normal levels of CRP, the method comprises administering to the patient a subsequent dose of SMAD7 antisense-oligonucleotide that is equal to or smaller than the initial dose of SMAD7 antisense-oligonucleotide. The normal and threshold levels of CRP are as described. The initial dose and subsequent dose are as described. Still preferred, the method of treatment or management further comprises analyzing the level of CRP in the patient after said administering step of SMAD7 antisense-oligonucleotide; and if the level of CRP is lower after said administration step of SMAD7 antisense-oligonucleotide than the level of CRP before said administration step, then administering to the patient a subsequent dose of SMAD7 antisense-oligonucleotide that is the same as the initial dose of SMAD7 antisense-oligonucleotide or smaller than the initial dose, or, if the level of CRP is unchanged or increased after said administration step compared to the level of CRP before said administration step, then administering to the patient a subsequent dose of SMAD7 antisense-oligonucleotide that is the same as the initial dose or greater than the initial dose of SMAD7 antisense-oligonucleotide or terminating the treatment. The SMAD7 antisense-oligonucleotide is as described.

In a further aspect of the invention, there is provided an SMAD7 antisense oligonucleotide for use in the treatment or management of IBD in a patient having IBD wherein treatment or management comprises administering simultaneously or successively said SMAD7 antisense oligonucleotide with a therapeutically effective amount of one or more additional therapeutic agents wherein the agents are selected from the group consisting of an aminosalicylate, an antibiotic, a steroid, an anti-inflammatory cytokine agent, and an immunomodulator.

In a further aspect of the invention, there is provided a combination comprising SMAD7 antisense and a therapeutically effective amount of one or more additional therapeutic agents, for use in the treatment or management of IBD in a patient having IBD, wherein the combination does not consist of (a) Mongersen and mesalamine, (b) Mongersen and budesonide, (c) Mongersen, mesalmine, and budesonide, or (d) Mongersen and a systemically administered corticosteroid. Preferably, the one or more additional therapeutic agents are selected from the group consisting of an aminosalicylate, an antibiotic, a steroid, an anti-inflammatory cytokine agent, and an immunomodulator.

ILLUSTRATIVE EMBODIMENTS

1. A method of treating IBD in a subject having a circulating CRP concentration greater than 3 mg/liter, the method comprising:
   a. administering at least one anti-SMAD7 therapy to the subject.
2. The method of embodiment 1, comprising, prior to step (a), measuring the circulating CRP concentration in the subject.
3. The method of embodiment 2, comprising, following step (a), measuring the circulating CRP concentration in the subject to determine whether any change in circulating CRP concentration has occurred.
4. A method for reducing CRP levels in a subject with IBD, the method comprising:
   a. administering at least one anti-SMAD7 therapy to the subject.
5. The method of embodiment 4, comprising, prior to step (a), measuring the circulating CRP concentration in the subject.
6. The method of embodiment 5, comprising, following step (a), measuring the circulating CRP concentration in the subject thereby to determine whether any change in circulating CRP concentration has occurred.
7. The method of any one of embodiments 2-3 or 5-6, wherein the circulating CRP concentration is measured by taking a sample from the subject.
8. A method for monitoring the responsiveness of a subject with IBD to treatment with at least one anti-SMAD7 therapy, the method comprising:
   a. determining the concentration of CRP in at least one sample obtained from the subject; and
   b. comparing the concentration of CRP in the sample with a control level of CRP,
   c. wherein a decrease in the concentration of CRP in the sample indicates that the subject is likely to respond, or is responsive to the anti-SMAD7 therapy.
9. The method of embodiment 8, comprising, prior to step (a), administering at least one anti-SMAD7 therapy to the subject.
10. The method of embodiment 8 or 9, comprising, following step (b), administering at least one anti-SMAD7 therapy to the subject.
11. The method of embodiment 8, wherein the subject is receiving at least one anti-SMAD7 therapy when the sample is obtained.
12. The method of any one of embodiments 7-11, wherein the decrease in the amount of CRP in the sample indicates that the subject is likely to enter remission.
13. The method of any one of embodiments 7-11, wherein the decrease in the amount of CRP in the sample indicates that the subject has entered remission.
14. The method of any one of embodiments 7-11, wherein the decrease in the amount of CRP in the sample coincides with a CDAI score of less than about 150 in the subject.
15. The method of embodiment 14, wherein the CDAI score is maintained for at least 1 day in the subject.
16. The method of embodiment 14, wherein the CDAI score is maintained for at least 1 week in the subject.
17. The method of embodiment 14, wherein the CDAI score is maintained for at least 2 weeks in the subject.
18. The method of any one of embodiments 15-17, wherein the CDAI score is observable at about 1 day after stopping treatment with the anti-SMAD7 therapy.
19. The method of any one of embodiments 15-17, wherein the CDAI score is observable at about 2 weeks after stopping treatment with the anti-SMAD7 therapy.

20. The method of any one of embodiments 15-17, wherein the CDAI score is observable at about 10 weeks after stopping treatment with the anti-SMAD7 therapy.
21. The method of any one of embodiments 15-17, wherein the CDAI score is observable at both about 1 day and about 2 weeks after stopping treatment with the anti-SMAD7 therapy.
22. The method of any one of embodiments 7-21, wherein the decrease in the amount of CRP in the sample coincides with a decrease in CDAI score of about 70 to about 100 in the subject.
23. The method of embodiment 22, wherein the decrease in CDAI score is observable about 1 day after stopping treatment with the anti-SMAD7 therapy.
24. The method of embodiment 22, wherein the decrease in CDAI score is observable about 2 weeks after stopping treatment with the anti-SMAD7 therapy.
25. The method of any one of embodiments 7-24, wherein the sample is a blood sample.
26. The method of any one of embodiments 8-11, wherein the control level of CRP is greater than or equal to about 3 mg/liter.
27. The method of any one of embodiments 8-11, wherein the concentration of CRP in the sample is less than about 3 mg/liter.
28. The method of any one of embodiments 8-11, wherein the control level of CRP is a baseline level of CRP obtained from the patient prior to administration of at least one anti-SMAD7 therapy or obtained immediately after the administration of at least one anti-SMAD7 therapy.
29. The method of embodiment 7, wherein the concentration of CRP in the sample taken from the subject after step (a) is less than about 3.0 mg/liter.
30. The method of any one of embodiments 2-3 or 5-29, wherein the concentration of CRP is determined by immunochemistry and/or by nucleotide analysis.
31. The method of embodiment 30, wherein the immunochemistry is performed using an anti-CRP antibody.
32. The method of embodiment 30, wherein the nucleotide analysis is performed using an oligonucleotide probe that binds a CRP nucleotide sequence or a pair of oligonucleotide primers capable of amplifying a CRP sequence via a polymerase chain reaction.
33. The method of any one of embodiments 2-3 or 5-32 carried out in vitro.
34. The method of any one of embodiments 1-7 or 9-10, wherein the anti-SMAD7 therapy is administered orally.
35. The method of any one of the preceding embodiments, wherein the anti-SMAD7 therapy is an anti-SMAD7 antisense therapy.
36. The method of embodiment 35, wherein the anti-SMAD7 antisense therapy comprises an anti-SMAD7 antisense oligonucleotide represented by SEQ ID NO: 1.
37. The method of any one of the preceding embodiments, wherein the anti-SMAD7 therapy is in the form of a pharmaceutical tablet for oral administration comprising:
  a. an intra-granular phase comprising an antisense oligonucleotide represented by SEQ ID NO: 1 or a pharmaceutically acceptable salt thereof and a pharmaceutically acceptable filler;
  b. an extra-granular phase comprising a disintegrant; and
  c. an enteric coating comprising an ethylacrylate-methacrylic acid copolymer.
38. The method of any one of the preceding embodiments, wherein the IBD is CD and/or UC.
39. The method of any one of the preceding embodiments, wherein the IBD is CD.
40. The method of any one of embodiments 1-38, wherein the IBD is UC.
41. The method of any one of the preceding embodiments, wherein the subject is a human subject.
42. The method of any one of the preceding embodiments, wherein the anti-SMAD7 therapy is administered following or concurrently with immunomodulators and/or mesalamine.
43. The method of embodiment 42, further comprising administering a steroid.
44. A kit comprising reagents for measuring CRP levels and detailed instructions for measuring a CDAI Score.
45. The kit of embodiment 44 wherein the reagents for measuring CRP levels are selected from the group consisting of an anti-CRP antibody, oligonucleotide probes that bind a CRP nucleotide sequence, and oligonucleotide primers capable of binding to and amplifying a CRP nucleotide sequence via a polymerase chain reaction.
46. The kit of embodiment 44 or 45 further comprising at least one of buffers, reagents and detailed instructions for measuring CRP levels.
47. The kit of embodiment 45 wherein the anti-CRP antibody is a primary antibody against a CRP protein, and the kit optionally further comprises a secondary antibody conjugated to a reporter enzyme, buffers, reagents and detailed instructions for measuring CRP levels in a sample using immunochemistry and/or a polymerase chain reaction.
48. A method of treating IBD, comprising administering to a patient an anti-SMAD7 therapy following or concurrently with treatment with an immunomodulator and/or mesalamine.
49. The method of embodiment 48, further comprising administering a steroid.
50. The method of embodiment 48 or 49, wherein the method results in the patient entering remission.
51. The method of embodiment 48 or 49, wherein the method results in a CDAI score of less than 150 in the subject.
52. The method of embodiment 51, wherein the CDAI score is maintained for at least 1 day in the subject.
53. The method of embodiment 51, wherein the CDAI score is maintained for at least 1 week in the subject.
54. The method of embodiment 51, wherein the CDAI score is maintained for at least 2 weeks in the subject.
55. The method of any one of embodiments 52-54, wherein the CDAI score is observable at about 1 day after stopping treatment.
56. The method of any one of embodiments 52-54, wherein the CDAI score is observable at about 2 weeks after stopping treatment.
57. The method of any one of embodiments 52-54, wherein the CDAI score is observable at about 10 weeks after stopping treatment.
58. The method of any one of embodiments 52-54, wherein the CDAI score is observable at both about 1 day and about 2 weeks after stopping treatment.
59. The method of any one of embodiments 48-58, wherein the method results in a decrease in CDAI score of about 70 to about 100 in the subject.

60. The method of embodiment 59, wherein the decrease in CDAI score is observable about 1 day after stopping treatment.
61. The method of embodiment 59, wherein the decrease in CDAI score is observable about 2 weeks after stopping treatment.
62. The method of any one of embodiments 48-61, wherein the method results in circulating CRP levels of less than about 3 mg/liter.
63. The method of any one of embodiments 48-62, wherein the anti-SMAD7 therapy is administered orally.
64. The method of any one of embodiments 48-62, wherein the anti-SMAD7 therapy is administered orally and the immunomodulator and/or mesalamine is administered via a different route.
65. The method of embodiment 64, wherein the different route is topical, parenteral, by inhalation spray, or rectal.
66. The method of any one of embodiments 48-65, wherein the anti-SMAD7 therapy is an anti-SMAD7 antisense therapy.
67. The method of embodiment 66, wherein the anti-SMAD7 antisense therapy comprises an anti-SMAD7 antisense oligonucleotide represented by SEQ ID NO: 1.
68. The method of any one embodiments 48-67, wherein the anti-SMAD7 therapy is in the form of a pharmaceutical tablet for oral administration comprising:
    a. an intra-granular phase comprising an antisense oligonucleotide represented by SEQ ID NO: 1 or a pharmaceutically acceptable salt thereof and a pharmaceutically acceptable filler;
    b. an extra-granular phase comprising a disintegrant; and
    c. an enteric coating comprising an ethylacrylate-methacrylic acid copolymer.
69. The method of any one of embodiments 48-68, wherein the IBD is CD and/or UC.
70. The method of embodiment 69, wherein the IBD is CD.
71. The method of embodiment 69, wherein the IBD is UC.
72. The method of any one of embodiments 48-71, wherein the patient is a human patient.
73. A method for treating or managing inflammatory bowel disease (IBD) in a patient having IBD, wherein the method comprises
    a. administering to the patient an initial dose of a SMAD7 antisense-oligonucleotide;
    b. analyzing the level of C-reactive protein (CRP) in the patient; and
    c. if the level of CRP is above normal levels of CRP, then administering to the patient a subsequent dose that is greater than or equal to the initial dose, or, if the level of CRP is below normal levels of CRP, then administering to the patient a subsequent dose that is equal to or smaller than the initial dose.
74. A method for treating or managing inflammatory bowel disease (IBD) in a patient having IBD, wherein the method comprises
    a. analyzing the level of CRP in the patient; and
    b. if the level of CRP is above a threshold level of CRP, then administering to the patient an initial dose of a SMAD7 antisense-oligonucleotide.
75. The method of embodiment 74, wherein the threshold level of CRP is at least 2-fold, at least 3-fold, at least 5-fold, at least 8-fold, at least 10-fold, at least 20-fold, at least 30-fold, at least 50-fold, at least 80-fold, or at least 100-fold above normal levels.
76. The method of embodiment 74, wherein the threshold level of CRP is in the $50^{th}$ percentile, $60^{th}$ percentile, $70^{th}$ percentile, $80^{th}$ percentile or $90^{th}$ percentile of CRP levels in a group of IBD patients.
77. The method of any one of embodiments 74 to 76, wherein the level of CRP is below 3 mg/L.
78. The method of embodiment 74, wherein the threshold level of CRP is more than 0.5 mg/L, more than 1.0 mg/L, more than 1.5 mg/L, more than 2.0 mg/L, more than 2.5 mg/L, more than 3.0 mg/L, more than 3.5 mg/L, more than 4.0 mg/L, more than 4.5 mg/L, or more than 5.0 mg/L.
79. The method of embodiment 74 or 78, wherein the level of CRP is between 0.5 mg/L and 3 mg/L, between 1 mg/L and 3 mg/L, between 1.5 mg/L and 3 mg/L, between 2 mg/L and 3 mg/L, or between 2.5 mg/L and 3 mg/L.
80. The method of embodiment 74, wherein the method further comprises:
    a. (c) analyzing the level of CRP in the patient after said administering step; and
    b. (d) if the level of CRP is above normal levels of CRP, then administering to the patient a subsequent dose that is greater than or equal to the initial dose, or, if the level of CRP is below normal levels of CRP then administering to the patient a subsequent dose that is equal to or smaller than the initial dose.
81. The method of embodiment 74 or embodiment 80, wherein if the level of CRP is above normal levels of CRP, then administering to the patient a subsequent dose that is greater than the initial dose, or, if the level of CRP is below normal levels of CRP then administering to the patient a subsequent dose that is smaller than the initial dose.
82. The method of embodiment 80, wherein, if the subsequent dose is equal to or greater than the maximum tolerated dose (MTD), then terminating the treatment.
83. The method of embodiment 80, wherein the level of CRP is analyzed at least 1 day, at least 3 days, at least 5 days, at least 1 week, at least 2 weeks, at least 3 weeks, at least 1 month, at least 2 months, at least 4 months, or at least 6 months after said administration step.
84. The method of embodiment 80, wherein the level of CRP is analyzed immediately after said administration step.
85. The method of embodiment 80, wherein the level of CRP is analyzed about 15 days or about 28 days after said administration step.
86. The methods of embodiment 73 or embodiment 74, wherein the normal levels of CRP are median levels of CRP in a healthy control group.
87. The method of embodiment 86, wherein the healthy control group and the patient having IBD are matched with respect to age, gender, ethnic origin, smoking habits, dietary habits, body-mass index (BMI), and/or exercise habits.
88. The method of embodiment 73 or embodiment 74, wherein normal levels of CRP are about 0.1 mg/L, 0.2 mg/L, 0.3 mg/L, 0.4 mg/L, 0.5 mg/L, 0.6 mg/L, 0.7 mg/L, 0.8 mg/L, 0.9 mg/L or 1.0 mg/L.
89. The method of embodiment 73 or embodiment 74, wherein the initial dose is less than 100 mg/day, less than 90 mg/day, less than 80 mg/day, less than 70 mg/day, less than 60 mg/day, less than 50 mg/day, less than 40 mg/day or less than 30 mg/day.

90. The method of embodiment 73 or embodiment 74, wherein the initial dose is at least 10 mg/day, at least 20 mg/day, at least 30 mg/day, at least 40 mg/day, at least 50 mg/day, at least 60 mg/day, at least 70 mg/day, at least 80 mg/day, or at least 90 mg/day.

91. The method of embodiment 73 or embodiment 74, wherein the initial dose is about 10 mg/day, about 20 mg/day, about 30 mg/day, about 40 mg/day, about 50 mg/day, about 60 mg/day, about 70 mg/day, about 80 mg/day, about 90 mg/day, or about 100 mg/day.

92. The method of embodiment 73 or embodiment 74, wherein the initial dose is 10 mg/day, 40 mg/day, 80 mg/day, or 160 mg/day.

93. The method of embodiment 73 or embodiment 80, wherein, if CRP levels are above normal levels, the subsequent dose is at least about 10 mg/day, at least about 20 mg/day, at least about 30 mg/day, at least about 40 mg/day, at least about 50 mg/day, at least about 60 mg/day, at least about 70 mg/day, at least about 80 mg/day, at least about 90 mg/day, at least about 100 mg/day, at least about 110 mg/day, at least about 120 mg/day, at least about 130 mg/day, at least about 140 mg/day, at least about 150 mg/day, or at least about 160 mg/day greater than the initial dose.

94. The method of embodiment 73 or embodiment 80, wherein, if CRP levels are below normal levels, the subsequent dose is at least about 10 mg/day, at least about 20 mg/day, at least about 30 mg/day, at least about 40 mg/day, at least about 50 mg/day, at least about 60 mg/day, at least about 70 mg/day, or at least about 80 mg/day smaller than the initial dose.

95. The method of embodiment 73 or embodiment 80, wherein the initial dose is between about 10 mg/day and 100 mg/day and the subsequent dose is between about 30 mg/day and 200 mg/day.

96. The method of embodiment 74, wherein the method further comprises:
    a. (c) analyzing the level of CRP in the patient after said administering step; and
    b. (d) if the level of CRP is lower after said administration step than the level of CRP before said administration step, then administering to the patient a subsequent dose that is the same as the initial dose or smaller than the initial dose, or, if the level of CRP is unchanged or increased after said administration step compared to the level of CRP before said administration step, then administering to the patient a subsequent dose that is the same as the initial dose or greater than the initial dose or terminating the treatment.

97. The method of embodiment 96, wherein if the patient is in clinical remission and the level of CRP is unchanged or increased after said administration step compared to the level of CRP before said administration step, then terminating the treatment.

98. The method of embodiment 96, wherein, if the level of CRP is at least 10%, at least 20%, at least 30%, at least 40%, at least 50%, or at least 70% decreased after said administration step compared to the level of CRP before said administration step, then administering to the patient a subsequent dose that is the same as the initial dose or smaller than the initial dose.

99. The method of embodiment 96, further comprising determining that the patient having IBD has a greater than 20%, greater than 30%, greater than 40%, greater than 50%, greater than 60%, greater than 70%, greater than 80%, greater than 90% or greater than 100% chance of experiencing clinical remission of the IBD for a time period of at least 1 week, at least 2 weeks, at least 3 weeks, at least 4 weeks, at least 6 weeks or at least 8 weeks, if the level of CRP after said administering step is at least 10%, at least 20%, at least 30%, at least 40%, at least 50%, at least 60%, or at least 70% decreased compared to the level of CRP before said administration step.

100. The method of embodiment 99, wherein the clinical remission in the patient having IBD is indicated by a Crohn's Disease Activity Index (CDAI) <150.

101. The method of embodiment 99, wherein the clinical remission is observed about one week, about two weeks, or about three weeks after said administration step and maintained for a period of at least 1 week, at least 2 weeks, at least 3 weeks, at least 4 weeks, at least 6 weeks or at least 8 weeks.

102. The method of embodiment 99, wherein the patient having IBD had a CDAI of between about 220 and about 400 one week prior to said administration step.

103. The method of embodiment 73 or embodiment 74, wherein the level of CRP in the patient having IBD is determined in a sample obtained from the patient having IBD.

104. The method of embodiment 103, wherein the sample is a blood, serum or plasma sample.

105. The method of embodiment 73 or embodiment 74, wherein the level of CRP is determined by immunochemistry or by nucleotide analysis.

106. The method of embodiment 105, wherein the level of CRP is determined by an enzyme-linked immunosorbent assay (ELISA).

107. The method of embodiment 73 or embodiment 74, further comprising determining a level of one or more additional analytes in the patient having IBD.

108. The method of embodiment 107, wherein the one or more additional analytes comprise interleukin 8 (IL8) or tumor necrosis factor alpha (TNFα).

109. The method of embodiment 73 or embodiment 74, wherein the IBD is Crohn's Disease (CD) or ulcerative colitis (UC).

110. The method of embodiment 109, wherein the patient having IBD is a steroid-dependent patient with active CD.

111. The method of embodiment 109, wherein the patient having IBD is a steroid-resistant patient with active CD.

112. The method of embodiment 73 or embodiment 74, wherein the SMAD7 antisense-oligonucleotide is administered orally to the patient having IBD.

113. The method of embodiment 73 or embodiment 74, wherein the SMAD7 antisense oligonucleotide targets region 108-128 of human SMAD7 (SEQ ID NO: 2).

114. The method of embodiment 73 or embodiment 74, wherein the SMAD7 antisense oligonucleotide targets nucleotides 403, 233, 294, 295, 296, 298, 299 or 533 of human SMAD7 (SEQ ID NO: 2).

115. The method of embodiment 73 or embodiment 74, wherein the SMAD7 antisense oligonucleotide comprises the nucleotide sequence of SEQ ID NO: 3 (5'-GTCGCCCCTTCTCCCCGCAGC-3').

116. The method of embodiment 73 or embodiment 74, wherein the SMAD7 antisense oligonucleotide is an antisense oligonucleotide phosphorothioate comprising the following sequence: 5'-GTXGCCCCTTCTC- CCXGCAG-3' (SEQ ID NO: 4) wherein X is 5-methyl-2'-deoxycytidine and wherein the internucleoside linkages are phosphorothioate linkages.

117. The method of embodiment 116, wherein the SMAD7 antisense oligonucleotide is an antisense oligonucleotide phosphorothioate comprising the following sequence: 5'-GTXGCCCCTTCTCCCXGCAGC-3' (SEQ ID NO: 1) wherein X is 5-methyl-2'-deoxycytidine and wherein the internucleoside linkages are phosphorothioate linkages.

118. The method of embodiment 117, wherein the SMAD7 antisense oligonucleotide is an antisense oligonucleotide according to Chemical Abstracts Service Registry Number (CAS RN) 1443994-98-6 or of CAS RN 1443994-46-4.

119. A method for treating or managing IBD in a patient with IBD having above normal CRP levels following administration of a dose of a SMAD7 antisense oligonucleotide, said method comprising administering to said patient a further dose of said oligonucleotide that is greater than or equal to the prior dose.

120. A method for treating or managing IBD in a patient with IBD having below normal CRP levels following administration of a dose of SMAD7 antisense oligonucleotide, said method comprising administering to said patient a further dose of said oligonucleotide that is less than or equal to the prior dose.

121. A method of treating or managing IBD in a patient with IBD having above normal CRP levels, said method comprising administering to said patient a dose of a SMAD7 antisense oligonucleotide.

122. The method of embodiment 121, wherein the administering is repeated until IL8 levels, CRP levels, or TNFα levels reach a normal level.

123. The method of embodiment 121, wherein the administering is repeated until the patient achieves a CDAI score of less than 150.

124. The method of embodiment 121, wherein the administering is repeated until the patient achieves clinical remission.

125. A method of monitoring the treatment or management of IBD in a patient with IBD, the method comprising analyzing CRP levels in the patient following each SMAD7 antisense oligonucleotide administration, wherein the absence of a decrease in CRP levels indicates that the treatment or management is not effective.

126. The method of embodiment 125, wherein CRP levels are analyzed one time, two times, three times, four times, about five times, about 10 times, about 15 times, about 20 times, or about 30 times after each administration of SMAD7 antisense oligonucleotide.

127. The method of embodiment 125, wherein the CRP levels are analyzed immediately after, about 1 hour after, about 3 hours after, about 6 hours after, about 12 hours after, about 1 day after, about 3 days after, about 1 week after, about 2 weeks after, and/or about 1 month after SMAD7 antisense oligonucleotide administration.

128. A method of treating or managing IBD in a patient with IBD having above normal levels of CRP, comprising increasing the amount of a SMAD7 antisense oligonucleotide administered to the patient until CRP levels in the patient decrease.

129. The method of embodiment 128, wherein CRP decreases to about a normal level of CRP or a below normal level of CRP.

130. A method for treating or managing inflammatory bowel disease (IBD) in a patient having IBD, comprising administering to the patient a combination of agents comprising a SMAD7 antisense oligonucleotide and one or more additional therapeutic agents, wherein the agents are administered in a therapeutically effective amount and wherein the combination does not consist of (a) Mongersen and mesalamine, (b) Mongersen and budesonide, (c) Mongersen, mesalmine, and budesonide, or (d) Mongersen and a systemically administered corticosteroid.

131. The method of embodiment 130, wherein the one or more additional therapeutic agents are selected from the group consisting of an aminosalicylate, an antibiotic, a steroid, an anti-inflammatory cytokine agent, and an immunomodulator.

132. The method of embodiment 131, wherein the one or more additional therapeutic agents comprise an aminosalicylate selected from the group consisting of 5-aminosalicylic acid, sulfasalazine, balsalazide, olsalazine, and mesalamine.

133. The method of embodiment 132, wherein the aminosalicylate comprises mesalamine.

134. The method of embodiment 131, wherein the one or more additional therapeutic agents comprise an antibiotic selected from the group consisting of a penicillin, a cephalosporin, a polymyxin, a rifampicin, a lipiarmycin, a quinolone, a sulfonamide, a macrolide, a lincosamide, a tetracycline, an aminoglycoside, a cyclic lipopeptide, a glycylcycline, an oxazolidinone, and a lipiarmycin.

135. The method of embodiment 131, wherein the one or more additional therapeutic agents comprise an antibiotic selected from the group consisting of erythromycin, clindamycin, genatmycin, meclycycline, sulfacetamide, benzoyl peroxide, ciprofloxacin, rifaximin, rifabutin, clofazimine, clarithromycin, azithromycin, isoniazid, tobramycin, rifaximin, amoxcillin, tetracycline, tinidazole, vancomycin, daptomycin, tigecyclin, linezolid, fidaxomicin, and metronidazole.

136. The method of embodiment 135, wherein the antibiotic comprises ciprofloxacin or metronidazole.

137. The method of embodiment 131, wherein the steroid is a corticosteroid.

138. The method of embodiment 137, wherein the corticosteroid is selected from the group consisting of budesonide, dexamethasone, betamethasone, tixocortol pivalate, triamcinolone acetonide, mometasone, amcinonide, desonide, fluocinonide, halcinonide, fluocortolone, hydrocortisone, fluticasone propionate, mometasone furotate, prednisone, prednisolone, beclomethasone dipropionate, flunisolide, and methylprednisolone.

139. The method of embodiment 137, wherein the corticosteroid comprises budenoside, dexamethasone, hydrocortisone, methylprednisolone, prednisolone, or prednisone.

140. The method of embodiment 139, wherein the patient having IBD is administered an oral dose of less than or equal to 40 mg/day prednisolone or less than or equal to 9 mg/day budesonide.

141. The method of embodiment 131, wherein the immunomodulator is an immunosuppressant.

142. The method of embodiment 141, wherein the immunosuppressant comprises azathioprine, 6-mercaptopurine, cyclosporine A, dactinomycin, anthracycline, mitomycin C, bleomycin, mithramycin, tacrolimus, mitoxanthrone, cyclophosphamide, micophenolate mofetile, rapamycine, minocycline, or methotrexate.

143. The method of embodiment 131, wherein the one or more additional therapeutic agents comprise an inflammatory cytokine antagonist selected from the group consisting of a tumor necrosis factor (TNF) antagonist and an interleukin 10 (IL10) antagonist.

144. The method of embodiment 143, wherein the TNF antagonist is selected from the group consisting of infliximab, adalimumab, certolizumab pegol, golimimab, etanercept, pentoxifylline, and bupropion.

145. The method of any of embodiments 130-144, wherein the patient is resistant to an IBD therapy.

146. The method of any of embodiments 130-145, wherein the patient is steroid-resistant.

147. The method of any of embodiments 130-146, wherein the SMAD7 antisense oligonucleotide and the one or more additional therapeutic agents are administered orally.

148. The method of any of embodiments 130-147, wherein (a) the amount of the SMAD7 antisense oligonucleotide administered is lower than the therapeutically effective amount of the SMAD7 antisense oligonucleotide when administered as a stand-alone therapy or (b) the amount of the one or more additional agents administered is lower than the therapeutically effective amount of the one or more additional agents when administered as a stand-alone therapy.

149. The method of any of embodiments 130-148, wherein one of a therapeutically effective dose of the SMAD7 antisense oligonucleotide alone or of a therapeutically effective dose of the one or more additional therapeutic agents alone is administered to the patient for a first period of time prior to administering the other of the SMAD7 antisense oligonucleotide or the one or more additional therapeutic agents.

150. The method of embodiment 149, wherein the period of time is sufficient for the patient having IBD to experience a reduction in IBD symptoms or to experience remission.

151. The method of any of embodiments 130-150, wherein the SMAD7 antisense oligonucleotide and the one or more additional therapeutic agents are administered concomitantly.

152. The method of embodiment 151, wherein the SMAD7 antisense oligonucleotide and the one or more additional therapeutic agents are administered in combination in a unit dosage form.

153. The method of embodiment 151, wherein the SMAD7 antisense oligonucleotide and the one or more additional therapeutic agents are administered in separate unit dosage forms.

154. The method of any of embodiments 130-150, wherein the SMAD7 antisense oligonucleotide and the one or more additional therapeutic agents are administered sequentially.

155. The method of any of embodiments 130-154, wherein the patient having IBD was undergoing an IBD therapy comprising the administration of the one or more additional therapeutic agents prior to receiving the first administration of the SMAD7 antisense oligonucleotide.

156. The method of any of embodiments 130-154, wherein the patient having IBD was undergoing an IBD therapy comprising the administration of the SMAD7 antisense oligonucleotide prior to receiving the first administration of the one or more additional therapeutic agents.

157. The method of any of embodiments 130-156, wherein the IBD is Crohn's Disease (CD) or ulcerative colitis (UC).

158. The method of embodiment 157, wherein the patient having IBD is a steroid-dependent patient with active CD.

159. The method of embodiment 157, wherein the patient having IBD is a steroid-resistant patient with active CD.

160. The method of any of embodiments 130-159, wherein, if the patient having IBD experiences disease worsening after receiving the SMAD7 antisense oligonucleotide for a second period of time, then a rescue therapy with biologics and/or immunosuppressive drugs are administered to the patient.

161. The method of embodiment 160, wherein the period of time is about 2 weeks and disease worsening includes an increased score in the Crohn's Disease Activity Index (CDAI) of ≥70 points.

162. The method of any of embodiments 130-159, wherein, if the patient having IBD experiences remission after receiving a dose of the SMAD7 antisense oligonucleotide and a dose of the one or more additional therapeutically active agent for a third period of time, then the dose of the SMAD7 or the dose of the additional antisense oligonucleotide is reduced in subsequent administrations.

163. The method of embodiment 162, wherein the period of time is about 14 days or about 28 days and remission includes a CDAI <150.

164. The method of any of embodiments 130-163, wherein the SMAD7 antisense oligonucleotide is administered to the patient having IBD at a dose of between 10 mg/day to about 300 mg/day.

165. The method of embodiment 164, wherein the SMAD7 antisense oligonucleotide is administered at a dose of about 10 mg/day, about 20 mg/day, about 30 mg/day, about 40 mg/day, about 50 mg/day, about 60 mg/day, about 70 mg/day, about 80 mg/day, about 90 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day, about 200 mg/day, about 210 mg/day, about 220 mg/day, about 230 mg/day, about 240 mg/day, about 250 mg/day, about 260 mg/day, about 270 mg/day, about 280 mg/day, about 290 mg/day, or about 300 mg/day.

166. The method of embodiment 165, wherein the SMAD7 antisense oligonucleotide is administered at a dose of about 40 mg/day, about 80 mg/day, or about 160 mg/day.

167. The method of any of embodiments 130-166, wherein the SMAD7 antisense oligonucleotide is a plurality of SMAD7 antisense oligonucleotides.

168. The method of any of embodiments 130-167, wherein the SMAD7 antisense oligonucleotide is administered orally to the patient.

169. The method of any of embodiments 130-167, wherein the one or more additional therapeutic agents are administered orally, parenterally, rectally, intravenously, topically, or by inhalation spray.

170. The method of any of embodiments 130-169, wherein the SMAD7 antisense oligonucleotide targets region 108-128 of human SMAD7 (GCTGCGGGGA-GAAGGGGCGAC; SEQ ID NO:7).

171. The method of any of embodiments 130-169, wherein the SMAD7 antisense oligonucleotide targets nucleotides 403, 233, 294, 295, 296, 298, 299 or 533 of the human SMAD7 mRNA (SEQ ID NO:2).

172. The method of any of embodiments 130-169, wherein the SMAD7 antisense oligonucleotide comprises the nucleotide sequence of SEQ ID NO:3 (5'-GTCGCCCCTTCTCCCCGCAGC-3').

173. The method any of embodiments 130-169, wherein the SMAD7 antisense oligonucleotide is an antisense oligonucleotide phosphorothioate comprising the following sequence: 5'-GTXGCCCCTTCTCCCXGCAG-3' (SEQ ID NO:4) wherein X is 5-methyl-2'-deoxycytidine and wherein the internucleoside linkages are phosphorothioate linkages.

174. The method of embodiment 173, wherein the SMAD7 antisense oligonucleotide is an antisense oligonucleotide phosphorothioate comprising the following sequence: 5'-GTXGCCCCTTCTCCCXGCAGC-3' (SEQ ID NO:1) wherein X is 5-methyl-2'-deoxycytidine and wherein the internucleoside linkages are phosphorothioate linkages.

175. The method of embodiment 174, wherein the SMAD7 antisense oligonucleotide is an antisense oligonucleotide according to Chemical Abstracts Service Registry Number (CAS RN) 1443994-98-6 or CAS RN 1443994-46-4.

176. The method of any of embodiments 130-175, wherein said additional therapeutic does not comprise a systemically administered corticosteroid, budesonide, or mesalamine.

177. A system for the treatment of IBD comprising a therapeutically effective amount of a SMAD7 antisense oligonucleotide and a therapeutically effective amount of one or more additional therapeutic agents.

178. A kit for the treatment of IBD comprising a therapeutically effective amount of a SMAD7 antisense oligonucleotide and a therapeutically effective amount of one or more additional therapeutic agents.

179. A pharmaceutical composition for the treatment of IBD comprising a therapeutically effective amount of a SMAD7 antisense oligonucleotide, therapeutically effective amounts of one or more additional therapeutic agents, and a pharmaceutically acceptable adjuvant and/or excipient.

180. The pharmaceutical composition of embodiment 179, wherein the pharmaceutical composition is in a unit dosage form.

181. The pharmaceutical composition of embodiment 180, wherein the unit dosage form is a tablet having a methacrylic acid-ethyl acrylate copolymer coating.

182. The pharmaceutical composition of any of embodiments 179-181, wherein the pharmaceutical composition is for oral administration.

183. The pharmaceutical composition of any of embodiments 179-182, wherein the SMAD7 antisense oligonucleotide targets region 108-128 of human SMAD7 (SEQ ID NO:2).

184. The pharmaceutical composition of any of embodiments 179-182, wherein the SMAD7 antisense oligonucleotide targets nucleotides 403, 233, 294, 295, 296, 298, 299 or 533 of human SMAD7 (SEQ ID NO:2).

185. The pharmaceutical composition of any of embodiments 179-182, wherein the SMAD7 antisense oligo-nucleotide comprises the nucleotide sequence of SEQ ID NO:3 (5'-GTCGCCCCTTCTCCCCGCAGC-3').

186. The pharmaceutical composition of any of embodiments 179-182, wherein the SMAD7 antisense oligonucleotide is an antisense oligonucleotide phosphorothioate comprising the following sequence: 5'-GTXGCCCCTTCTCCCXGCAG-3' (SEQ ID NO:4) wherein X is 5-methyl-2'-deoxycytidine and wherein the internucleoside linkages are phosphorothioate linkages.

187. The pharmaceutical composition of any of embodiments 179-182, wherein the SMAD7 antisense oligonucleotide is an antisense oligonucleotide phosphorothioate comprising the following sequence: 5'-GTXGCCCCTTCTCCCXGCAGC-3' (SEQ ID NO:1) wherein X is 5-methyl-2'-deoxycytidine and wherein the internucleoside linkages are phosphorothioate linkages.

188. The pharmaceutical composition of any of embodiments 179-182, wherein the SMAD7 antisense oligonucleotide is an antisense oligonucleotide according to Chemical Abstracts Service Registry Number (CAS RN) 1443994-98-6 or CAS RN 1443994-46-4.

189. The pharmaceutical composition of any of embodiments 179-182, wherein the one or more additional therapeutic agents comprise an aminosalicylate, an antibiotic, a steroid, a tumor necrosis factor (TNF) antagonist, or an immunomodulator.

190. An in vitro method for predicting the responsiveness of a patient with inflammatory bowel disease to an anti-SMAD therapy, wherein the method comprises comparing the level of C-reactive protein (CRP) in the patient to a threshold level of CRP; and wherein a higher level of CRP in the patient than the threshold level of CRP indicates that the patient is likely to respond, or is responsive to the anti-SMAD therapy.

191. A SMAD7 antisense oligonucleotide for use in a method of treating or managing inflammatory bowel disease (IBD) in a patient having IBD, wherein the method comprises: (a) analyzing the level of C-reactive protein (CRP) in a patient; and (b) if the level of CRP is above a threshold level of CRP, then administering to the patient an initial dose of a SMAD7 antisense oligonucleotide.

192. The SMAD7 antisense oligonucleotide for use of embodiment 191, wherein the threshold level of CRP is about 0.5 mg/L or more, about 1.0 mg/L or more, about 1.5 mg/L or more, about 2.0 mg/L or more, about 2.5 mg/L or more, about 3.0 mg/L or more, about 3.5 mg/L or more, about 4.0 mg/L or more, about 4.5 mg/L or more, or about 5.0 mg/L or more.

193. The SMAD7 antisense oligonucleotide for use of embodiment 191, wherein the threshold level of CRP is about 3.0 mg/L.

194. The SMAD7 antisense oligonucleotide for use of embodiment 191, wherein the threshold level of CRP is the CRP level in the patient having IBD before onset of IBD symptoms or before diagnosis of IBD in the patient.

195. The SMAD7 antisense oligonucleotide for use of any one of embodiment 191 to 194, wherein the method further comprises:
(c) analyzing the level of CRP in the patient after said administration step; and
(d) if the level of CRP is above baseline levels of CRP, then administering to the patient a subsequent dose of the SMAD7 antisense oligonucleotide that is greater than or equal to the initial dose, or, if the level of CRP is below baseline levels of CRP, then administering to the patient a subsequent dose of the SMAD7 antisense oligonucleotide that is equal to or smaller than the initial dose; and wherein the baseline levels of CRP are the CRP levels in the patient having IBD before administration of the initial dose of the SMAD7 antisense oligonucleotide.

196. A method for treating or managing inflammatory bowel disease (IBD) in a patient having IBD, wherein the method comprises: (a) analyzing the level of C-reactive protein (CRP) in the patient; and (b) if the level of CRP is above a threshold level of CRP, then administering to the patient an initial dose of a CRP antagonist.

197. The method of embodiment 196, wherein the method further comprises: (c) analyzing the level of CRP in the patient after said administration step; and (d) if the level of CRP is above normal levels of CRP or at or above baseline levels of CRP, then administering to the patient a subsequent dose of the CRP antagonist that is greater than or equal to the initial dose, or, if the level of CRP is below normal levels of CRP or below baseline levels of CRP, then administering to the patient a subsequent dose of the CRP antagonist that is equal to or lower than the initial dose.

198. The method of embodiment 196 or embodiment 197, wherein the threshold level of CRP is about 0.5 mg/L or more, about 1.0 mg/L or more, about 1.5 mg/L or more, about 2.0 mg/L or more, about 2.5 mg/L or more, about 3.0 mg/L or more, about 3.5 mg/L or more, about 4.0 mg/L or more, about 4.5 mg/L or more, or about 5.0 mg/L or more.

199. The method of embodiment 196 or embodiment 197, wherein the threshold level of CRP is between about 0.5 mg/L and about 3 mg/L, between about 1 mg/L and about 3 mg/L, between about 1.5 mg/L and about 3 mg/L, between about 2 mg/L and about 3 mg/L, or between about 2.5 mg/L and about 3 mg/L.

200. The method of embodiment 196 or embodiment 197, wherein the threshold level of CRP is about 3.0 mg/L.

201. The method of embodiment 196 or embodiment 197, wherein the threshold level of CRP is the CRP level in the patient having IBD before onset of IBD symptoms or before diagnosis of IBD in the patient.

202. The method of any one of embodiment 196 to embodiment 201, wherein the normal levels of CRP are about 0.1 mg/L or less, about 0.2 mg/L or less, about 0.3 mg/L or less, about 0.4 mg/L or less, about 0.5 mg/L or less, about 0.5 mg/L or less, about 0.6 mg/L or less, about 0.7 mg/L or less, about 0.8 mg/L or less, about 0.9 mg/L or less, or about 1.0 mg/L or less.

203. The method of any one of of embodiment 196 to embodiment 201, wherein the normal levels of CRP are about 1.0 mg/L or less.

204. The method of any one of embodiment 196 to embodiment 203, wherein the baseline level of CRP is the CRP level in the patient having IBD before administration of the initial dose of the CRP antagonist.

205. The method of any one of embodiment 196 to embodiment 204, wherein the patient having IBD is a patient having Crohn's disease (CD).

206. The method of any one of embodiment 196 to embodiment 204, wherein the patient having IBD is a patient having UC.

207. A method for treating or managing gastroduodenal Crohn's disease in a patient having gastroduodenal Crohn's disease comprising administering to the patient a therapeutically effective dose of a CRP antagonist.

208. A method for treating or managing Crohn's (granulomatous) colitis in a patient having Crohn's (granulomatous) colitis comprising administering to the patient a therapeutically effective dose of a CRP antagonist.

209. A method for treating or managing collagenous colitis in a patient having collagenous colitis comprising administering to the patient a therapeutically effective dose of a CRP antagonist.

210. A method for treating or managing lymphocytic colitis in a patient having lymphocytic colitis comprising administering to the patient a therapeutically effective dose of a CRP antagonist.

211. A method for treating or managing ischaemic colitis in a patient having ischaemic colitis comprising administering to the patient a therapeutically effective dose of a CRP antagonist.

212. A method for treating or managing diversion colitis in a patient having diversion colitis comprising administering to the patient a therapeutically effective dose of a CRP antagonist.

213. A method for treating or managing Behcet's disease in a patient having Behcet's disease comprising administering to the patient a therapeutically effective dose of a CRP antagonist.

214. A method for treating or managing microscopic colitis in a patient having microscopic colitis comprising administering to the patient a therapeutically effective dose of a CRP antagonist.

215. A method for treating or managing proctosigmoiditis in a patient having proctosigmoiditis comprising administering to the patient a therapeutically effective dose of a CRP antagonist.

216. A method for treating or managing jejunoileitis in a patient having jejunoileitis comprising administering to the patient a therapeutically effective dose of a CRP antagonist.

217. A method for treating or managing left-sided colitis in a patient having left-sided colitis comprising administering to the patient a therapeutically effective dose of a CRP antagonist.

218. A method for treating or managing pancolitis in a patient having pancolitis comprising administering to the patient a therapeutically effective dose of a CRP antagonist.

219. A method for treating or managing ileocolitis in a patient having ileocolitis comprising administering to the patient a therapeutically effective dose of a CRP antagonist.

220. A method for treating or managing ileitis in a patient having ileitis comprising administering to the patient a therapeutically effective dose of a CRP antagonist.

221. A method for treating or managing indeterminate colitis in a patient having indeterminate colitis comprising administering to the patient a therapeutically effective dose of a CRP antagonist.

222. The method of any one of claims 190 to 221, wherein the CRP antagonist is a CRP antisense oligonucleotide (CRP AON).

223. A CRP antagonist for use in a method of treating or managing inflammatory bowel disease (IBD) in a patient having IBD, wherein the method comprises: (a) analyzing the level of C-reactive protein (CRP) in a patient; and (b) if the level of CRP is above a threshold level of CRP, then administering to the patient an initial dose of the CRP antagonist.

224. A method for treating inflammatory bowel disease, the method comprising administering an oligonucleotide in an amount effective to reduce a level of CRP in a subject relative to a control level.

225. A method for treating inflammatory bowel disease, the method comprising administering an oligonucleotide to a subject having an elevated level of CRP, thereby to induce remission in the subject.

226. A method for treating inflammatory bowel disease in a patient having a circulating CRP concentration greater than 3 mg/liter, the method comprising administering an oligonucleotide to the subject.

227. A method for reducing CRP levels in a subject with inflammatory bowel disease, the method comprising administering an oligonucleotide to the subject.

228. A method for predicting responsiveness of a patient having IBD to an anti-SMAD7 or an anti-CRP therapy comprising measuring CRP levels in the patient having IBD, wherein CRP levels above 3 mg/L indicate that the patient is responsive to the anti-SMAD7 or the anti-CRP therapy.

229. The method of any one of embodiment 196 to embodiment 228, wherein the anti-CRP agent (CRP antagonist or anti-CRP therapy) or the oligonucleotide is an anti-CRP antisense oligonucleotide selected from
   i. CRP AONs as disclosed in
      1. WO 2005/005599 (e.g., AONs of Table 2),
      2. WO 2003/010284 A2 (e.g., AONs of Table 1)
      3. WO 2007/143317 A2 (e.g., AONs of Table 9)
         a. U.S. Pat. No. 8,859,514 B2 (e.g., AONs of Table 13)
      4. U.S. Pat. Nos. 7,425,545 B2; 7,863,252 B2, 6,964,950 B2, 7,491,815 B2, 7,915,231 B2, 8,093,224 B2 and 7,326,693 B2;
   ii. ISIS 329993 (ISIS-CRP$_{Rx}$ (phosphorothioate)), ISIS 353491, ISIS 353512
   iii. CRP AONs complementary to a sequence of 8 or more nucleotides of CRP mRNA of paragraph [00114] (Entrez GeneID No. 1401; SEQ ID NO: 8) and allelic variants thereof.

230. The method of embodiment 223 or embodiment 228, wherein the anti-CRP agent (CRP antagonist or anti-CRP therapy) is a neutralizing CRP Antibody.

231. An SMAD7 antisense oligonucleotide for use in the methods of any one of the preceding embodiments.

DETAILED DESCRIPTION

Figure 1:
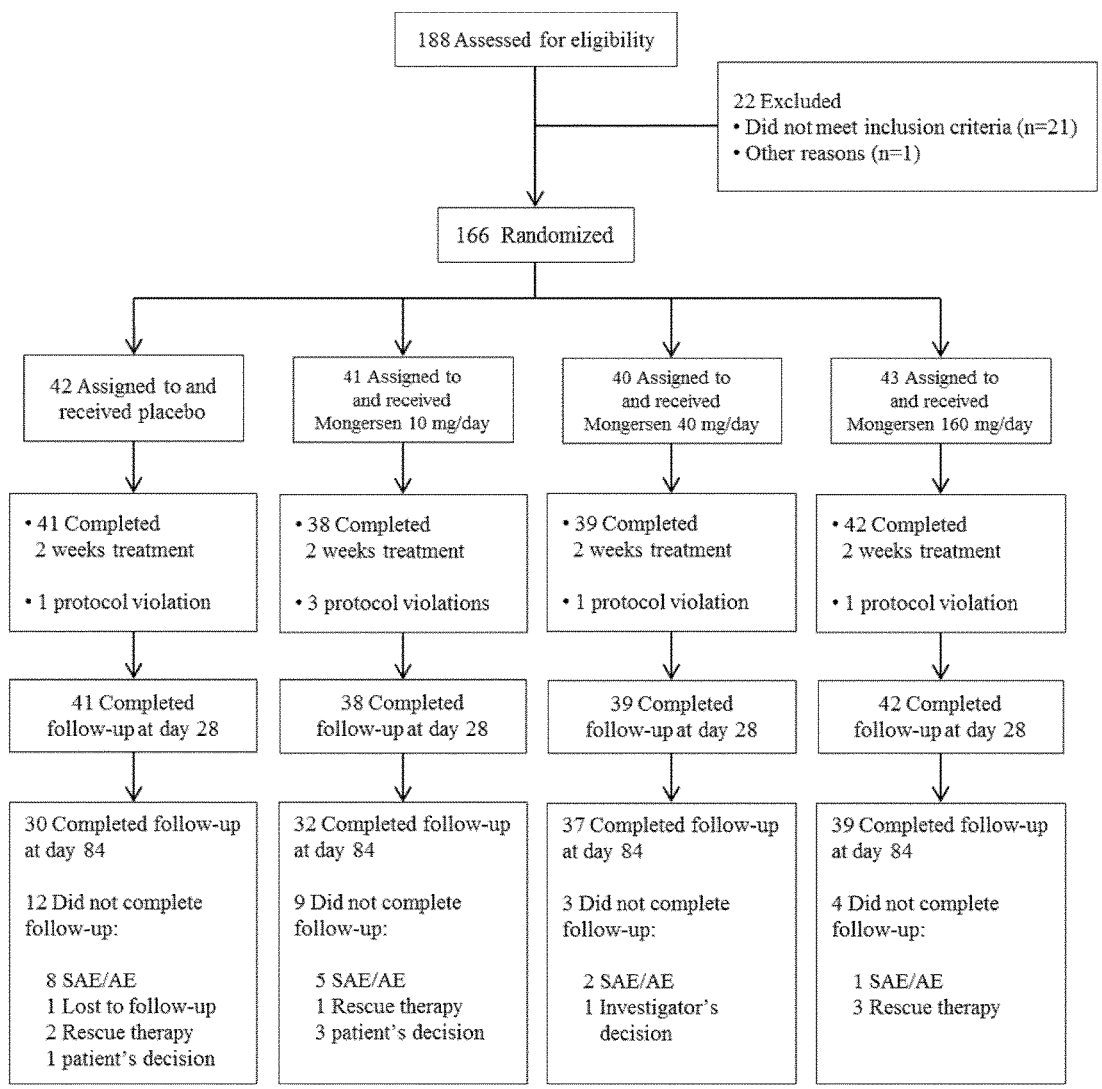
FIG. 1 is a flow diagram showing the evaluation of patients assessed for eligibility in the trial and the progress of patients allowed to enter the trial (trial progression displayed from top to bottom). As indicated, prior to starting the trial 188 patients were assessed for eligibility. 22 patients failed the screening process, and 166 patients were allowed to enter the trial on day 0. As indicated 42 patients were assigned to receive placebo, 41 patients were assigned to receive Mongersen at 10 mg/day, 40 patients were assigned to receive Mongersen at 40 mg/day, and 43 patients were assigned to receive Mongersen at 160 mg/day. 41 patients completed the treatment in the placebo group, 38 patients completed the treatment in the 10 mg/day Mongersen group, 39 patients completed the treatment in the 40 mg/day Mongersen group, and 42 patients completed the treatment in the 160 mg/day Mongersen group. Of the patients who completed the assigned treatment correctly, 30 patients in the placebo group, 32 patients in the 10 mg/day Mongersen group, 37 patients in the 40 mg/day Mongersen group, and 39 patients in the 160 mg/day Mongersen group completed a follow-up procedure.

The invention provides methods that are generally useful for treating and managing IBD in a patient having IBD. Patients having IBD include, but are not limited to, patients having UC and CD, including steroid-dependent and steroid-resistant forms of the latter. The method is particularly useful in terms of managing treatment in a patient being treated with an anti-SMAD7 therapy, such as a SMAD7 antisense oligonucleotide therapy. Without being bound by any theory the SMAD7 antisense oligonucleotide therapy may be any therapy that includes an oligonucleotide that is capable of binding to a SMAD7 mRNA transcript and inducing degradation of the SMAD7 mRNA transcript via RNase H, preventing splicing of the SMAD7 mRNA transcript, or preventing protein translation of the SMAD7 mRNA transcript.

Methods of the invention are useful for predicting and determining responsiveness of patients having IBD to treatment with SMAD7 antisense oligonucleotide. Thus, methods of the invention can be used to identify patients that are likely to respond to SMAD7 antisense oligonucleotide treatment as well as patients that are unlikely to respond to SMAD7 antisense oligonucleotide treatment. The methods described herein are also useful for determining whether a patient is or is not responsive to IBD treatment. Generally, methods of the invention can also be used to determine the level or likely level of responsiveness in a patient having IBD being treated with a SMAD7 antisense oligonucleotide. Based upon a determination of a level of responsiveness or a likely level of responsiveness, administration of the SMAD7 antisense oligonucleotide may be initiated, repeated, maintained, increased, decreased, or terminated. Responsiveness may be determined using a number of factors including, but not limited to: analysis of levels or changes in levels of biomarkers and/or other analytes (e.g., IL8, CRP, TNFα), CDAI score or changes in CDAI score, or assessment of symptoms of IBD (e.g., weight loss, tissue inflammation, bloody stool).

Similarly, the methods are useful for evaluating efficacy and safety of treatment with a SMAD7 antisense oligonucleotide in patient having IBD. For example, methods of the invention may include determining changes in levels of biomarker expression or other indicators or manifestations of disease state that can indicate that treatment with the SMAD7 antisense oligonucleotide is effective or not effective to cause partial or complete remission or amelioration of IBD. Determining levels or changes in levels of biomarker expression, disease symptoms, tissue, blood, or systemic levels of the SMAD7 antisense oligonucleotide, or indicators of general health may also indicate a worsening of disease state or unsafe drug levels. Assessment of multiple indicators before, during, between, and/or after treatment(s) may be used to monitor disease stage, progression, and severity.

The invention is based in part on the discovery of a relationship between IBD disease state and CRP levels. Specifically, the inventors have discovered that CRP levels are a useful biomarker for determining whether a patient is responsive to, likely to be responsive to, not responsive to, or likely not responsive to treatment of IBD using a SMAD7 antisense oligonucleotide.

Furthermore, CRP levels can be used to manage disease treatment using a SMAD7 antisense oligonucleotide, specifically with respect to dose amount of the SMAD7 antisense oligonucleotide. For example, levels of CRP may be used to determine whether a patient having IBD should be given a specific dose amount, for example, a higher dose or a lower dose, of SMAD7 antisense oligonucleotide, for example in a subsequent dose, with respect to, for example, a previously administered dose, for example, an initial dose, of SMAD7 antisense oligonucleotide. Thus, administration of a SMAD7 antisense oligonucleotide may be adjusted in terms of, for example, dose amount or frequency, with respect to absolute levels of CRP or relative levels of CRP in a patient having IBD. For instance, administration of a SMAD7 antisense oligonucleotide may be adjusted based on absolute levels of CRP by comparing absolute levels of CRP measured in a sample from a patient having IBD with a normal level of CRP, where the normal level of CRP is, for instance, either a benchmark value or a median level of CRP in a healthy control group matched to the patient having IBD. In some embodiments of the invention, administration of a SMAD7 antisense oligonucleotide may be adjusted based on relative levels of CRP, for instance, based on a comparison of CRP levels before and after SMAD7 antisense oligonucleotide administration, immediately after and later after SMAD7 antisense oligonucleotide administration, or during and after SMAD7 antisense oligonucleotide administration. In some embodiments, the SMAD7 antisense oligonucleotide may be administered multiple times between an initial detection of CRP levels and a later detection of CRP levels used to generate the comparison of CRP levels in the patient sample.

In some embodiments of the invention the IBD patient being treated is a patient with above normal CRP levels. In some embodiments, a patient is known to have high CRP levels before treatment. In some embodiments, CRP levels in the IBD patient are determined before treatment, after treatment, before administration of an initial dose of a SMAD7 antisense oligonucleotide, after administration of an initial dose of a SMAD7 antisense oligonucleotide, before administration of a subsequent dose of a SMAD7 antisense oligonucleotide, and/or after administration of a subsequent dose of a SMAD7 antisense oligonucleotide.

The present inventors have also developed methods for treating IBD (e.g., Crohn's disease and ulcerative colitis) in patients using a combination of an antisense oligonucleotide directed against SMAD7 and one or more additional therapeutic agents. Use of a combination therapy can result in synergistic benefits, which can lead to improved patient outcome, reduced side effects, allow for lower dosages, or allow less frequent administration of one or both the therapeutics being administered. This approach can also reduce resistance to stand-alone therapies (e.g., steroid resistance).

Inflammatory Bowel Disease

The present invention provides methods for treatment of IBD. "Inflammatory bowel disease" (or "IBD"), as used herein, ay refer to a number of chronic inflammatory diseases including Crohn's disease (CD), gastroduodenal Crohn's disease, Crohn's (granulomatous) colitis, ulcerative colitis (UC), collagenous colitis, lymphocytic colitis, ischaemic colitis, diversion colitis, Behcet's disease, microscopic colitis, ulcerative proctitis, proctosigmoiditis, jejunoileitis, left-sided colitis, pancolitis, ileocolitis, ileitis, and indeterminate colitis. CD and UC are the two most common forms of IBD. IBD is an autoimmune disease of the digestive system. CD may be localized to any portion of the gastrointestinal tract, including the terminal ileum, and may impact all cell types of the gastrointestinal tract. UC is localized to the colon and rectum, and affects cells of the mucosa only.

Both environmental and genetic factors are believed to play a role in IBD, although the identity of such factors is not well-defined. Environmental components may include alterations in flora of the gut which are affected by exposure to ingested foods and medications.

IBD is associated with symptoms including abdominal pain, vomiting, diarrhea, rectal bleeding, severe cramps, muscle spasms, weight loss, malnutrition, fever, anemia, skin lesions, joint pain, eye inflammation, liver disorders, arthritis, pyoderma gangrenosum, primary sclerosing cholangitis, and non-thyroidal illness syndrome. Children suffering from UC may suffer from growth defects.

Forms of CD include steroid-dependent and steroid-resistant forms of CD, including active CD. Patients with IBD who suffer from a steroid-dependent form of CD are responsive to treatment with steroid therapy, but cannot terminate or curtail steroid therapy without suffering from an increase in occurrence of symptoms associated with CD. Patients with IBD who suffer from a steroid-resistant form of CD are not responsive to treatment with steroid therapy. Steroid therapeutics, including steroid therapeutics commonly prescribed and/or administered to patients with IBD, include: corticosteroids, for example, prednisone, dexamethasone, hydrocortisone, methylprednisolone, prednisone, and budesonide. A human patient suffering from active CD is a patient actively suffering from symptoms of CD, for example, but not limited to, bloody stool, weight loss, and/or abdominal cramps.

Treatment, Management, and Evaluation

A "subject" or "patient" as described herein, refers to any animal at risk for, suffering from or diagnosed for IBD, including, but not limited to, mammals, primates, and humans. In certain embodiments, the subject may be a non-human mammal such as, for example, a cat, a dog, or a horse. In a preferred embodiment, the subject is a human subject. A subject may be an individual diagnosed with a high risk of developing IBD, someone who has been diagnosed with IBD, someone who previously suffered from IBD, or an individual evaluated for symptoms or indications of IBD, for example, high CRP expression levels or a high CDAI index score.

"A patient with IBD," as used herein, refers to a patient suffering from any of the symptoms or manifestations of IBD, a patient who may suffer from any of the symptoms or manifestations of IBD, or any patient who might benefit from a method of the invention for treating or evaluating treatment for IBD. A patient in need may include a patient who is diagnosed with a risk of developing IBD, a patient who has suffered from IBD in the past, or a patient who has previously been treated for IBD. Of particular relevance are individuals that suffer from IBD associated with increased levels of CRP, TNFα, and/or IL8 expression. In some embodiments, the patient with IBD is a Crohn's disease (CD) patient. In some embodiments, the patient with IBD is an ulcerative colitis (UC) patient.

The terms "treat," "treatment," "treating," and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., preventing the disease from increasing in severity or scope; (c) relieving the disease, i.e., causing partial or complete amelioration of the disease; or (d) preventing relapse of the disease, i.e., preventing the disease from returning to an active state following previous successful treatment of symptoms of the disease or treatment of the disease. The term "treating" may also mean reducing at least one symptom associated with the disease or condition being treated.

In some embodiments, the methods of treating provided herein refer to (a) an anti-SMAD7 monotherapy with use of CRP as a biomarker; (b) an anti-SMAD7 combination therapy; (c) an anti-SMAD7 combination therapy with use of CRP as a biomarker; (d) an anti-CRP monotherapy; (e) an anti-CRP monotherapy with use of CRP as a biomarker; (f) an anti-CRP combination therapy; and (g) an anti-CRP combination therapy with use of CRP as a biomarker.

The terms "manage," "management," "managing," and the like are used herein to generally mean controlling the severity or manifestation of symptoms of a disease, or the means of treating the disease. Generally, management is used to obtaining a desired pharmacological and/or physiological effect. The effect may be therapeutic in terms of partially or completely curing a disease and/or adverse effect attributed to the disease or ensuring that a particular symptom or manifestation of the disease does not occur or reoccur in a patient or does not rise to an undesirable or intolerable level in a patient. The term "management" as used herein covers any management of a disease in a mammal, particularly a human, and includes: (a) inhibiting the disease, e.g., preventing the disease from increasing in severity or scope; (b) relieving the disease, e.g., causing partial or complete amelioration of the disease; or (c) preventing relapse of the disease, e.g., preventing the disease from returning to an active state following previous successful treatment of symptoms of the disease or treatment of the disease. "Management" as used herein may also be used with reference to administration of a specific treatment for the disease, for example, a SMAD7 antisense oligonucleotide.

In some embodiments of the invention, a patient having IBD will be administered an initial dose of an anti-SMAD7 therapy, for instance, a SMAD7 antisense oligonucleotide. As used herein, "initial dose" refers to a dose of an anti-SMAD7 therapy administered to a patient having IBD, in a series of doses. A series of doses may include one or more doses. For instance, a series of doses may comprise a single dose of an anti-SMAD7 therapy or more than a single dose of an anti-SMAD7 therapy. An initial dose may be a dose of an anti-SMAD7 therapy administered to a patient prior to any later dose administered to the patient. For instance, an initial dose may be, but is not limited to, the first dose of an anti-SMAD7 therapy administered to a patient during a patient's entire treatment history. An initial dose may also be a first dose in a treatment regimen administered to a patient following previous administration of an anti-SMAD7 therapy, for instance, during an earlier round of treatment. Furthermore, an initial dose may be a first dose in a series of doses within a round of treatment, such that the initial dose may be administered after a prior dose in the same round of treatment. Alternatively, an "initial dose" may be the first dose administered to a patient after analyzing levels of CRP and/or another biomarker or biomarkers in a patient, or may be the most recently administered dose before a determination of the levels of CRP and/or another biomarker or biomarkers in a patient.

In some embodiments of the invention, a patient having IBD will be administered a subsequent dose of an anti-SMAD7 therapy, for instance, a SMAD7 antisense oligonucleotide. As used herein, "subsequent dose" refers to a dose of an anti-SMAD7 therapy administered to a patient having IBD, after administration of a prior dose, for example, an initial dose. Thus, a subsequent dose may be administered to a patient having IBD in a series of doses comprising two or more doses. Furthermore, in some instances, the amount of a subsequent dose may be calibrated with respect to an initial dose or a prior dose, such that a subsequence dose is greater, equal to, or lesser than a prior dose. Calibration of the amount of a subsequent dose may be based on levels or changes in levels of CRP and/or another biomarker or biomarkers in a patient having IBD, for instance: levels of CRP in a patient having IBD analyzed prior to or after a prior dose, for instance, an initial dose; or changes in CRP levels in a patient having IBD before and after a prior dose, for instance, an initial dose. A subsequent dose may be a dose administered to a patient having IBD after a first dose, for instance, an initial dose, of an anti-SMAD7 therapy administered to a patient having IBD. A subsequent dose may also be a dose administered after a prior dose of an anti-SMAD7 therapy administered to a patient having IBD, for instance, a dose administered after a prior dose in the same round of treatment or a different round of treatment, for instance, a previous round of treatment. A subsequent dose may be a subsequent dose with respect to any prior dose, for instance, a prior dose immediately preceding the subsequent dose or a prior dose followed by one or more doses administered prior to administration of the subsequent dose.

As used herein, "Crohn's Disease Activity Index" or "CDAI" refers to a measurement or index used to assess the progress of patients suffering from CD as described by Best et al., GASTROENTEROLOGY, 70:439-44 (1976). CDAI scores of 150 or below are generally associated with inactive disease and are indicative of better prognosis than higher scores. Values above 150 are generally associated with active disease and values above 450 are associated with extremely severe disease. CDAI scores may be used to determine how well a patient is responding to therapy and may be used to identify patients in remission. In certain embodiments, a benchmark clinical response means that the subject displays a decrease in CDAI score by at least 100 points. In a clinical trial, a CDAI score of 150 or below is generally associated with remission.

As used herein, "Ulcerative Colitis Disease Activity Index" or "UCDAI" refers to a measurement or index used to assess the progress of patients suffering from UC as described by Sutherland et al., Gastroenterology, 92:1894-98 (1987). The UCDAI is a series of qualifiers about the symptoms of UC including stool frequency, rectal bleeding, the appearance of the colon lining, and a physician's rating of disease activity. Each of these qualifiers is given a number from 0 to 3, with 3 being the highest disease activity. In a clinical trial, remission is often defined as a UCDAI score of 1 or less, and improvement is a reduction of 3 or more points from the score at the beginning of the trial. UCDAI may be used in clinical trials to determine how well a patient is responding to therapy and may be used to identify patients in remission. Other commonly used indices for measuring disease severity in UC patients include the Truelove and Witts Index, the St. Mark's Index, the Simple Clinical Colitis Activity Index (SCCAI), the Lichtiger Index, the Ulcerative Colitis Symptom Score (UCSS), and the Mayo Clinic Score.

As used herein, "remission" or "clinical remission" refers to a reduction—partial or complete—of a clinical manifestation or manifestations or symptoms of IBD. For instance, clinical remission may include an easing of the severity of symptoms associated with IBD, for example, bloody stool, weight loss, or tissue inflammation, or a complete disappearance of symptoms of IBD from the patient. In embodiments of the invention, clinical remission may be indicated by changes in or measurement of CDAI score. For example, a CDAI score of less than about 150, less than about 155, less than about 160, less than about 165, less than about 170, or less than about 175 may indicate clinical remission. Clinical remission may be observed following administration of the SMAD7 antisense oligonucleotide to the patient having IBD. Clinical remission may be observed by measuring factors that contribute to a disease activity index score, such as a CDAI score, or by measurement of objective factors, for instance, but not limited to, levels of analytes in a sample from a patient. Furthermore, in some embodiments of the invention, clinical remission is both observed after an administration step and maintained for a period of time following the initial observation. For instance, in some embodiments clinical remission is observed about one week, about two weeks, or about three weeks after administration of the SMAD7 antisense oligonucleotide and maintained for a period of at least 1 week, at least 2 weeks, at least 3 weeks, at least 4 weeks, at least 6 weeks or at least 8 weeks following the initial observation of clinical remission. In particular embodiments, remission is defined as maintaining a CDAI score of less than 150 for at least two weeks.

As used herein, "response" or "responding" to treatment means that a subject with CD displays: (a) a decrease in CDAI score, e.g., a decrease in CDAI score by 20 points, 30 points, 40 points, 50 points, 60 points, 70 points, 80 points, 90 points, 100 points or more; (b) a CDAI score of less than 150; and/or (c) the induction of remission.

With respect to a subject with UC, "response" or "responding" to treatment means that the subject displays (a) a decrease in UCDAI score, e.g., a decrease in UCDAI score by 1 point, 2 points or more; (b) a UCDAI score of 1 or less; and/or (c) the induction of remission.

In some embodiments a baseline (e.g., a baseline score, level, or value) is analyzed. In some embodiments, a baseline is analyzed in methods involving the selection of a patient having IBD for treatment with an anti-SMAD7 therapy or an anti-CRP therapy. In some embodiments, a baseline is analyzed in a method involving a method of monitoring a patient having IBD during a period of treatment with an anti-SMAD7 therapy or an anti-CRP therapy. In some embodiments, a baseline level of CRP in a patient is at or above a threshold level (e.g., above 3 mg/L), that may result in the selection of the patient for administration of an anti-SMAD7 therapy or an anti-CRP therapy. In some embodiments, a baseline level of CRP in a patient is below a threshold level (e.g., below 3.0 mg/L) that may result in the selection of the patient for an anti-SMAD7 therapy or an anti-CRP therapy. In some embodiments, the baseline is analyzed before administering the initial dose of an anti-SMAD7 therapy or an anti-CRP therapy to a patient having IBD. For example, the baseline can be analyzed, at least 1 day, at least 1 week, at least 2 weeks, at least 4 weeks, at least 6 weeks, at least 6 weeks, at least 2 months, at least 3 months, at least 6 months, at least 9 months, at least 1 year, at least 3 years, or at least 5 years before administering the initial dose of the anti-SMAD7 therapy or the anti-CRP therapy to the patient. In some embodiments, the baseline is analyzed at the same time or immediately before or after administering the initial dose of an anti-SMAD7 therapy or an anti-CRP therapy to the patient. For example, the baseline can be analyzed less than 6 hours, less than 4 hours, less than 2 hours, less than 1 hour, less than 30 min, less than 15 min, less than 10 min, or less than 5 min before or after administering the initial dose of the anti-SMAD7 therapy or the anti-CRP therapy to the patient. In some embodiments, the baseline is analyzed during a chronic phase of IBD (flare up) in the patient having IBD, e.g., before administering the initial dose of the anti-SMAD7 therapy or the anti-CRP therapy to the patient. In some embodiments, the baseline is analyzed when the patient is in remission (e.g., while receiving a previous IBD treatment, which can be an IBD treatment other than an anti-SMAD7 therapy or an anti-CRP therapy). In some embodiments, the baseline is an average score from several timepoints before administering the initial dose of the anti-SMAD7 therapy or the anti-CRP therapy.

In some embodiments, a subject (e.g., a patient having IBD, such as CD or UC) responds to treatment if the subject displays an improvement in an endoscopic outcome (e.g., mucosal healing), a clinical parameter (e.g., CDAI), or a histological score.

In some embodiments, a subject responds to treatment if the subject (e.g., a patient having IBD, such as CD or UC) displays mucosal healing. In some embodiments, mucosal healing is analyzed using the Simple Endoscopic Score for Crohn's Disease (SES-CD). In some embodiments, analyzing the SES-CD comprises analyzing the presence and size of ulcers, the extent of ulcerated surface, the extent of affected surface, or the presence and type of narrowings in the ileum, the right colon, the transverse colon, the left colon, the rectum, or in a combination or all of the listed colon regions. In some embodiments, mucosal healing is analyzed by analyzing the presence or absence of ulcers in the subject. In some embodiments, a subject displaying mucosal healing has an SES-CD=0 or an SES-CD ≤2. In some embodiments, ulcers are absent in a subject displaying mucosal healing.

In some embodiments, analyzing the SES-CD comprises analyzing an absolute SES-CD. In some embodiments, analyzing the SES-CD comprises analyzing changes in SES-CD from baseline (e.g., SES-CD increases or decreases).

In some embodiments, the SES-CD is analyzed using variables according to Table 1:

TABLE 1

| | SES-CD Values | | | |
|---|---|---|---|---|
| Variable | 0 | 1 | 2 | 3 |
| Size of ulcers | None | Aphthous ulcers (Diameter: 0.1 to 0.5 cm) | Large ulcers (Diameter: 0.5 to 2.0 cm) | Very large ulcers (Diameter: >2.0 cm) |

TABLE 1-continued

| Variable | SES-CD Values | | | |
|---|---|---|---|---|
| | 0 | 1 | 2 | 3 |
| Ulcerated surface | None | <10% | 10%-30% | >30% |
| Affected surface | Unaffected segment | <50% | 50%-75% | >70% |
| Presence of narrowing | None | Single, can be passed | Multiple, can be passed | Cannot be passed |

In some embodiments, a subject has a SES-CD ≥7 before administering an anti-SMAD7 therapy or an anti-CRP therapy to the subject. In some embodiments, a subject has a CDAI score ≥220 and ≤450 and a SES-CD ≥7 before administering an anti-SMAD7 therapy or an anti-CRP therapy to the subject.

In some embodiments, a subject responds to an anti-SMAD7 therapy or an anti-CRP therapy if the subject's SES-CD is ≤5, ≤4, ≤3, ≤2, ≤1, or 0 after administering the anti-SMAD7 therapy or an anti-CRP therapy to the subject. In some embodiments, a subject responds to an anti-SMAD7 therapy or an anti-CRP therapy if the subject's SES-CD is ≤2 after administering the anti-SMAD7 therapy or the anti-CRP therapy to the subject. In some embodiments, a subject responds to an anti-SMAD7 therapy or an anti-CRP therapy if the subject's SES-CD is 0 after administering the anti-SMAD7 therapy or the anti-CRP therapy to the subject.

In some embodiments, a subject responds to an anti-SMAD7 therapy or an anti-CRP therapy if the subject's SES-CD is <80%, <75%, <70%, <65%, <60%, <55%, <50%, <45%, <40%, <35%, <30%, <25%, or <20% of the subject's baseline SES-CD after administering the anti-SMAD7 therapy or the anti-CRP therapy to the subject. In some embodiments, a subject responds to an anti-SMAD7 therapy or an anti-CRP therapy if the subject's SES-CD is <50% of the subject's baseline SES-CD after administering the anti-SMAD7 therapy or the anti-CRP therapy to the subject.

In some embodiments, a subject responds to an anti-SMAD7 therapy or an anti-CRP therapy if the subject's SES-CD is reduced ≥50% from baseline after administering the anti-SMAD7 therapy or the anti-CRP therapy to the subject. In some embodiments, a subject responds to an anti-SMAD7 or an anti-CRP therapy if the subject's SES-CD is reduced by 4 points compared to baseline after administering the anti-SMAD7 therapy or the anti-CRP therapy to the subject.

In some embodiments, a subject responds to an anti-SMAD7 therapy or an anti-CRP therapy if intestinal mucosal ulcerations are absent in the subject after administering the anti-SMAD7 therapy or the anti-CRP therapy to the subject.

In some embodiments, a subject (e.g., a patient having IBD, such as CD or UC) responds to a treatment if the subject displays an improvement in a histological score. Histological scores can be analyzed as absolute histological sores from intestinal mucosa of the subject. In some embodiments, the histological score is analyzed as a change in the histological score from intestinal mucosa of the subject from baseline.

In some embodiments, analyzing the CDAI comprises analyzing CDAI components, such as abdominal pain, stool frequency or composite scores (like PRO-2 or PRO-3). Patient Reported Outcome (PRO) analysis involves patients quantifying their own symptoms, which can be useful in assessing IBD severity. A two-item Patient Reported Outcome (PRO-2) for CD considers two CDAI variables, e.g., liquid or soft stool frequency and abdominal pain. Methods for determining PRO-2 scores are well known in the art. For example, a total PRO-2 score can be calculated based on information provided in a patient questionnaire or diary. Daily scores of liquid or soft stool frequency and abdominal pain can be averaged over 7 days and weighted, e.g., using multiplication factors applied also during CDAI determinations. In some embodiments, PRO-2 values of 8, 14, and 34 points can correspond to CDAI scores of 150, 220, and 450 points and PRO-2 score changes from baseline of 2, 5, and 8 points can correspond to changes in CDAI scores of 50, 70, and 100 points.

In some embodiments, a subject (e.g., a patient having IBD, such as CD or UC) responds to a treatment if the subject displays an improvement in a two-item patient reported outcome (PRO-2) test. In some embodiments, the improvements in the PRO-2 test comprise improvements in absolute PRO-2 scores. In some embodiments, the improvements in the PRO-2 test comprise improvements in PRO-2 scores relative to baseline (e.g., PRO-2 score increases or decreases).

In some embodiments, a subject responds to an anti-SMAD7 therapy or an anti-CRP therapy if the subject's PRO-2 score is ≥2, ≥3, ≥4, ≥5, ≥6, ≥7, ≥8, ≥9, ≥10, ≥12, or ≥14 points lower compared to baseline after administering the anti-SMAD7 therapy or the anti-CRP therapy to the subject.

In some embodiments, a subject responds to an anti-SMAD7 therapy or an anti-CRP therapy if the subject's PRO-2 score is <14, <12, <10, <8, <6, <4, or <2 after administering the anti-SMAD7 therapy or the anti-CRP therapy to the subject.

In some embodiments, a subject responds to an anti-SMAD7 therapy or an anti-CRP therapy if the subject's average daily liquid or soft stool frequency score is reduced by ≥20%, ≥30%, ≥40%, ≥50%, ≥60%, ≥70%, ≥80%, or ≥90% compared to baseline after administering the anti-SMAD7 therapy or the anti-CRP therapy to the subject.

In some embodiments, a subject responds to an anti-SMAD7 therapy or an anti-CRP therapy if the subject's average daily abdominal pain score is reduced by ≥20%, ≥30%, ≥40%, ≥50%, ≥60%, ≥70%, ≥80%, or ≥90% compared to baseline after administering the anti-SMAD7 therapy or the anti-CRP therapy to the subject.

In some embodiments, a subject responds to an anti-SMAD7 therapy or an anti-CRP therapy if the subject displays a decrease of SES-CD score from baseline ≥50%, a decrease of CDAI score from baseline ≥100 points; and/or a decrease of PRO-2 score from baseline ≥8 points.

In some embodiments, a subject (e.g., a patient having IBD, such as CD or UC) responds to a treatment if the subject displays an improvement in the Crohn's disease endoscopic index of severity (CDEIS).

In some embodiments, "clinical remission" can be indicated by changes in or measurement of PRO-2 score or of SES-CD. In some embodiments, a subject (e.g., a patient having IBD, such as CD or UC) experiences remission if the PRO-2 score is ≤8. In some embodiments, a subject experiences remission if the SES-CD score is ≤2, the CDAI score is <150 and/or the PRO-2 score is ≤8. In some embodiments, a subject experiences remission if the SES-CD score is 0.

As used herein, "SMAD7" (also known as CRCS3, FLJ16482, MADH7, MADH8, MAD (mothers against decapentaplegic, Drosophila) homolog 7, MAD homolog 8, SMAD, mothers against DPP homolog 7, mothers against DPP homolog 8) means the human protein or any of the mRNA transcripts encoded by the gene identified by Entrez GeneID No. 4092 and allelic variants thereof.

As used herein, "CRP" (also known as C-reactive protein, pentraxin-related; Pentraxin; and PTX1) means the human protein or any of the mRNA transcripts encoded by the gene identified by Entrez GeneID No. 1401 and allelic variants thereof (SEQ ID NO: 8).

As used herein, "IL8" (also known as Interleukin-8 (IL-8); Tumor Necrosis Factor-Induced Gene 1; NAF; Granulocyte Chemotactic Protein 1 (GCP1); LECT; LUCT; Protein 3-10C; Beta-Thromboglobulin-Like Protein; Neutrophil-Activating Peptide 1; Neutrophil-Activating Protein 1 (NAP1; NAP-1); Emoctakin; GCP-1; LYNAP; Lymphocyte Derived Neutrophil Activating Peptide; Lung Giant Cell Carcinoma-Derived Chemotactic Protein; Small Inducible Cytokine Subfamily B, Member 8; Beta Endothelial Cell-Derived Neutrophil Activating Peptide; Monocyte-Derived Neutrophil Chemotactic Factor (MDNCF); Monocyte-Derived Neutrophil-Activating Peptide (MONAP); Alveolar Macrophage Chemotactic Factor I; C-X-C Motif Chemokine 8; and Chemokine (C-X-C Motif) Ligand 8 (CXCL8)) means the human protein or any of the mRNA transcripts encoded by the gene identified by Entrez GeneID No. 3576 and allelic variants thereof.

As used herein, "TNFα" (also known as Tumor Necrosis Factor, DIF, Tumor Necrosis Factor Ligand Superfamily Member 2 (TNFSF2), APC1 Protein, cachectin, Tumor Necrosis Factor A (TNFA), Tumor Necrosis Factor-α (TNF-α), and Tumor Necrosis Factor-alpha (TNF-alpha)) means the human protein or any of the mRNA transcripts encoded by the gene identified by Entrez GeneID No. 7124 and allelic variants thereof.

Control Levels and Control Samples

A control level of CRP, TNFα, and/or IL8 may be determined by determining the level of CRP, TNFα, and/or IL8 protein or mRNA transcript in a sample (e.g., a blood sample) obtained from the subject prior to treatment with an anti-SMAD7 therapy. The control level of CRP, TNFα, and/or IL8 may provide a baseline for monitoring a subject's response to treatment. A control sample may be obtained from the subject on the day the anti-SMAD7 therapy is first administered (e.g., Day 1 of a treatment regimen), for example, immediately after administration of at least one anti-SMAD7 therapy. In other embodiments, a control sample may be obtained from a subject one day prior to the start of an anti-SMAD7 therapy (e.g., Day 0 of a treatment regimen). Alternatively, a control sample may be obtained from a subject 2, 3, 4, 5, 6, 7 or more days prior to the start of an anti-SMAD7 therapy. For example, the increase or decrease in CRP, TNFα, or IL8 concentration may be measured prior to treatment (e.g., in a control sample), during treatment, and/or after treatment to monitor a subject's response to therapy, e.g., an anti-SMAD7 therapy. In an exemplary embodiment of the invention, a control level of CRP is equal to or greater than about 3 mg/liter.

In some embodiments, a control level may be established for a subject based on long-term monitoring of circulating CRP, TNFα, and/or IL8 concentration in the subject. In such instances, it is contemplated that a subject may undergo multiple rounds of treatment with an anti-SMAD7 therapy. The circulating CRP, TNFα, and/or IL8 concentration detected following multiple rounds of treatment may be compared to a prior control level of CRP, TNFα, and/or IL8 for the subject to determine whether the subject has responded to therapy and/or is likely to respond to further treatment with an anti-SMAD7 therapy. In other embodiments, a control or baseline level for a subject may be established based on an average measurement of a circulating CRP, TNFα, and/or IL8 concentration determined from multiple baseline samples obtained over time (e.g., obtained over the course of days, weeks, months, or years). Accordingly, any test or assay conducted as disclosed herein may be compared with a previous or established control level and it may not be necessary to obtain a new control sample from the subject for comparison, e.g., if the subject is receiving more than one round of treatment with an anti-SMAD7 therapy.

Normal levels of CRP, TNFα, and/or IL8 may be determined based on numerical reference values or with respect to levels of CRP, TNFα, and/or IL8 in a healthy control group.

For instance, in some embodiments, normal levels of CRP are about 0.01 mg/L, about 0.05 mg/L, about 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, about 1.0 mg/L, about 1.5 mg/L, about 2.0 mg/L, about 2.5 mg/L, or about 3.0 mg/L.

In other embodiments of the invention, normal levels of CRP, TNFα, and/or IL8 are defined as median levels of CRP, TNFα, and/or IL8 in a healthy control group.

A healthy control group may be defined based on various criteria related to genetic background, habits, and physical attributes matched to the same set of criteria in the patient. For instance, in some embodiments, the healthy control group and the patient having IBD are matched with respect to age, gender, ethnic origin, smoking habits, dietary habits, body-mass index (BMI), recreational drug use, medical drug use, drug use related to IBD, and/or exercise habits. Other factors that can be matched between the patient and control group include, but are not limited to, clinical criteria (e.g., CDAI score, Mayo score, severity of IBD-related symptoms), metabolism, IBD patient's personal disease history, genetic factors, IBD patient's family disease history, exposure to environmental factors (e.g., pollutants, toxins, allergens), and life-style (e.g., urban, suburban, or rural place of work and/or domicile).

In some embodiments, the control group is the patient receiving a treatment with an SMAD7 antisense oligonucleotide prior to receiving an initial dose of the SMAD7 antisense oligonucleotide. In some embodiments, the patient is a treatment naive patient.

Data Interpretation

In some embodiments, prior to initial administration of an anti-SMAD7 therapy, the level of CRP in a patient having IBD is analyzed and compared to a threshold level. As described herein, a threshold level may be established based on CRP levels in a healthy control group or a group of IBD patients. In general, a threshold level will be elevated with respect to normal CRP levels, for example median CRP levels, in a healthy control group or it may fall within the spectrum of CRP levels in a control group, for example a control group comprised of IBD patients.

A subject's responsiveness to treatment with an anti-SMAD7 therapy can be interpreted with respect to the control level of CRP in a sample obtained from the subject prior to treatment. A subject may be identified as sensitive to treatment (e.g., responsive or likely to respond) to treatment with an anti-SMAD7 therapy if there is a decrease in the concentration of CRP in the sample obtained from the subject compared to the control sample. In some embodiments the sample may be obtained while the subject is receiving an anti-SMAD7 therapy treatment. In other embodiments, the sample may be obtained after the subject has stopped receiving treatment, for example, about 1 day, about 7 days (i.e., about 1 week), about 14 days (i.e., about 2 weeks), about 28 days, about 56 days, about 70 days and/or longer, after stopping treatment. In a preferred embodiment, the sample may be obtained about one day after stopping anti-SMAD7 therapy treatment. In some embodiments, a decrease in the concentration of CRP, for example, a decrease from a CRP control level concentration of greater than or about 3.0 mg/liter to a CRP concentration of less than 3.0 mg/liter in the sample indicates that the subject is likely to enter remission or has entered remission.

In a contemplated embodiment of the invention, a decrease in the amount of CRP in the sample coincides with a CDAI score indicating that the subject is responsive to therapy and/or has entered remission or is likely to enter remission. For example, in some embodiments, a decrease in the amount of CRP in the sample compared to the control level coincides with a CDAI score of less than about 200, less than about 190, less than about 180, less than about 170, less than about 160, or less than about 150 in the subject. In a particular embodiment, a decrease in the amount of CRP in the sample compared to the control level coincides with a CDAI score of less than about 150 in the subject. In some embodiments, the CDAI score that coincides with the decrease in CRP concentration is maintained for at least one day, at least one week, at least two weeks, or at least 10 weeks in the subject. In some embodiments, the CDAI score that coincides with the decrease in CRP concentration is observable after stopping treatment with the anti-SMAD7 therapy. For example, the CDAI score that coincides with the decrease in CRP concentration may be observable about 1 day, about 1 week, about 2 weeks, about 10 weeks, about 1 day and about 2 weeks, or longer after stopping treatment with an anti-SMAD7 therapy.

In some embodiments, a decrease in the amount of CRP in the sample coincides with a decrease in CDAI score indicating that the subject is responsive to therapy and/or has entered remission or is likely to enter remission. For example, in some embodiments of the invention, a decrease in the amount of CRP in the sample compared to the control level coincides with a decrease in CDAI score of about 50, about 60, about 70, about 80, about 90, about 100, about 110, about 120, about 130, about 140, or about 150 in the subject. In particular embodiments, a decrease in the amount of CRP in the sample compared to the control level coincides with a decrease in CDAI score of about 70 to about 100 in the subject. In some embodiments, the decrease in CDAI score that coincides with the decrease in the amount of CRP is observable after stopping treatment with the anti-SMAD7 therapy. For example, the decrease in CDAI score that coincides with the decrease in the amount of CRP may be observable about 1 day, about 1 week, about 2 weeks, about 3 weeks, about 4 weeks, about 10 weeks, or longer after stopping treatment with an anti-SMAD7 therapy. In some embodiments, the decrease in CDAI score that coincides with the decrease in the amount of CRP is observable about 1 day or about 2 weeks after stopping treatment with an anti-SMAD7 therapy.

In some embodiments, patients receiving an anti-SMAD7 therapy, such as a SMAD7 antisense oligonucleotide, also receive one or more additional IBD therapies, e.g., steroids. In some embodiments, patients receiving the anti-SMAD7 therapy and the one or more additional IBD therapies can taper the one or more additional IBD therapies if they respond to the anti-SMAD7 therapy and/or experience clinical remission, e.g., as indicated by decreasing CDAI scores and/or decreasing CRP levels. In some embodiments, patients experiencing clinical remission following the administration of an anti-SMAD7 therapy (e.g., CDAI<150 at both day 14 and day 28 following completion of a 2-week treatment regimen with a SMAD7 antisense oligonucleotide) can taper steroid use.

Alternatively, a subject may be identified as resistant to treatment (e.g., non-responsive or unlikely to respond) with an anti-SMAD7 therapy if there is no change or an increase in circulating CRP concentration in the sample obtained from the subject, compared to the control level. In one embodiment, the sample may be obtained while the subject is receiving an anti-SMAD7 therapy treatment. In other embodiments, the sample may be obtained after the subject has stopped receiving treatment, for example, about 1 day, about 7 days (i.e., about 1 week), about 14 days (i.e., about 2 weeks), about 28 days, about 56 days, about 70 days, and/or longer after stopping treatment. In a preferred embodiment, the sample may be obtained about one day after stopping anti-SMAD7 therapy treatment.

In some embodiments, patients experiencing a worsening of disease during a course of treatment with an anti-SMAD7 therapy, e.g., as indicated by increasing CDAI scores (e.g., >70 CDAI score increase) and/or increasing CRP levels (e.g., >50% increase in CRP levels), are administered a rescue therapy (e.g., biologics such as TNF$\alpha$ inhibitors) and/or immunosuppressive drugs).

Differences in patient CRP levels and threshold CRP levels are indicative of a patient's potential responsiveness to anti-SMAD7 therapy. For example, patient CRP levels that are elevated relative to a threshold CRP level indicate that a patient may be responsive to anti-SMAD7 therapy. Threshold levels of CRP can be established using different criteria. In some embodiments, the threshold level of CRP is determined with respect to normal CRP levels, for example median CRP levels, in a control group. Control groups may be comprised of healthy/normal subjects (e.g., a healthy control group) or groups of IBD patients.

For instance, in some embodiments, a CRP threshold level is at least 2-fold, at least 3-fold, at least 5-fold, at least 8-fold, at least 10-fold, at least 20-fold, at least 30-fold, at least 50-fold, at least 80-fold, or at least 100-fold above normal levels. In other embodiments, the CRP threshold level is in the $50^{th}$ percentile, $60^{th}$ percentile, $70^{th}$ percentile, $80^{th}$ percentile or $90^{th}$ percentile of CRP levels with respect to CRP levels, for example median CRP levels, in a group of IBD patients. Additionally, in some embodiments, the threshold level of CRP is more than 0.5 mg/L, more than 1.0 mg/L, more than 1.5 mg/L, more than 2.0 mg/L, more than 2.5 mg/L, more than 3.0 mg/L, more than 3.5 mg/L, more than 4.0 mg/L, more than 4.5 mg/L, more than 5.0 mg/L, more than 7.5 mg/L, or more than 10 mg/L. In some embodiments, the threshold level of CRP is about 0.5 mg/L, about 1.0 mg/L, about 1.5 mg/L, about 2.0 mg/L, about 2.5 mg/L, about 3.0 mg/L, about 3.5 mg/L, about 4.0 mg/L, about 4.5 mg/L, about 5.0 mg/L, about 7.5 mg/L, or about 10 mg/L.

In some embodiments, the control group may consist of the patient receiving an initial dose of a SMAD7 antisense oligonucleotide. In some embodiments, normal CRP levels, or CRP threshold levels, may be the CRP baseline levels that are observed in a patient prior to administration of an initial dose of SMAD7 antisense oligonucleotide. CRP levels can subsequently be monitored in a patient over time, following the administration of the initial dose or of subsequent doses of SMAD7 antisense oligonucleotide to the patient. CRP levels in the patient following one or more administrations of a SMAD7 antisense oligonucleotide can be compared to the CRP baseline level in the patient. Dosing regimens for the SMAD7 antisense oligonucleotide can be adjusted, depending on whether CRP levels in the patient increase, decrease or remain constant relative to the patient's CRP baseline level.

In some embodiments, the control group may consist of the patient receiving an initial dose of a SMAD7 antisense oligonucleotide. In some embodiments, normal CRP levels, or CRP threshold levels, may be the CRP baseline levels that are observed in a patient prior to administration of an initial dose of SMAD7 antisense oligonucleotide. CRP levels can subsequently be monitored in a patient over time, following the administration of the initial dose or of subsequent doses of SMAD7 antisense oligonucleotide to the patient. CRP levels in the patient following one or more administrations of a SMAD7 antisense oligonucleotide can be compared to the CRP baseline level in the patient. Dosing regimens for the SMAD7 antisense oligonucleotide can be adjusted, depending on whether CRP levels in the patient increase, decrease or remain constant relative to the patient's CRP baseline level.

Pharmaceutical Compositions

Pharmaceutical compositions containing an antisense oligonucleotide against SMAD7, the additional therapeutic, or a combination thereof, can be presented in a dosage unit form and can be prepared by any suitable method. A pharmaceutical composition should be formulated to be compatible with its intended route of administration. Useful formulations can be prepared by methods well known in the pharmaceutical art. For example, see *Remington: The Science and Practice of Pharmacy*, $22^{nd}$ ed. (Pharmaceutical Press and Philadelphia College of Pharmacy at University of the Sciences, 2012).

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Anti-SMAD7 Therapies

The present disclosure is directed in part to methods of treating IBD in a subject with anti-SMAD7 therapies, including pharmaceutical compositions that include an antisense oligonucleotide. The present disclosure is also directed to methods of treating IBD in a patient with a therapeutic combination that includes an anti-SMAD7 therapeutic, including pharmaceutical compositions that include an antisense oligonucleotide. Anti-SMAD7 therapy includes targeted therapies against SMAD7 (e.g., anti-SMAD7 antisense therapies, for example the SMAD7 antisense oligonucleotide represented by SEQ ID NO: 1, and antibodies against SMAD7).

Antisense oligonucleotides are short synthetic oligonucleotide sequences complementary to the messenger RNA (mRNA), which encodes for the target protein (e.g., SMAD7). Antisense oligonucleotide sequences hybridize to the mRNA producing a double-strand hybrid that can lead to the activation of ubiquitary catalytic enzymes, such as RNase H, which degrades DNA/RNA hybrid strands thus preventing protein translation. Without being bound by theory, an antisense oligonucleotide provided herein can hybridize to its target sequence as RNA or DNA. Thus, even if a DNA sequence is provided as target, the corresponding RNA sequence (including uracil instead of thymine) is included.

The contemplated SMAD7 antisense oligonucleotide may target any region of a SMAD7 mRNA or DNA. In certain embodiments, an anti-SMAD7 antisense oligonucleotide may target site 403, 233, 294, 295, 296, 298, 299, and/or 533 (i.e., nucleotides 403, 233, 294, 295, 296, 298, 299, and 533, respectively) of the human SMAD7 mRNA (e.g., of SEQ ID NO: 2; which represents the coding sequence CDS (288-1568) of NM_005904.3, homo sapiens SMAD family member 7 (SMAD7), transcript variant 1, mRNA; the SMAD7 antisense oligonucleotides provided herein can target both a DNA having a nucleotide sequence of SEQ ID NO: 2 and a corresponding RNA of SEQ ID NO: 2 with Ts replaced by Us). In certain embodiments, the anti-SMAD7 antisense oligonucleotide targets nucleotide 108-128 of the SMAD7 coding sequence (GCTGCGGGGAGAAGGGGCGAC; SEQ ID NO: 7), or of a corresponding RNA sequence having Ts replaced by Us.). The nucleotides 108-128 of the SMAD7 coding sequence correspond to nucleotides 395-416 of NCBI Reference Sequence NM_005904.3.

In certain embodiments, an antisense oligonucleotide may be derived from the following anti-SMAD7 antisense oligonucleotide 5'-GTCGCCCCTTCTCCCCGCAGC-3' (SEQ ID NO: 3).

It is contemplated herein that an antisense oligonucleotide targeting SMAD7 may comprise a mixed-backbone wherein the cytosine residues in a CpG pair are replaced by 5'-methylcytosine (abbreviated as Me-dC). Methylphosphonate linkages may also be placed at the 5' and/or 3' ends of an antisense oligonucleotide (abbreviated as MeP).

Exemplary antisense oligonucleotide therapies that target SMAD7 include, but are not limited to 5'-GTXYCCCCT-TCTCCCXYCAG-3' (SEQ ID NO: 5), wherein X is a nucleoside comprising or including a nitrogenous base selected from the group consisting of cytosine and 5-methylcytosine or a 2'-O-methyl nucleoside comprising a cytosine nucleobase, and wherein Y is a nucleoside including or comprising a nitrogenous base selected from the group consisting of guanine and 5-methylguanine or a 2'-O-methyl nucleoside comprising a guanine nucleobase, optionally provided that least one of the nucleosides X or Y comprises or includes a methylated nitrogenous base. In some specific embodiments, all internucleoside linkages are phosphorothioate linkages;

5'-GTXGCCCCTTCTCCCXGCAG-3' (SEQ ID NO: 4), wherein X is 5-methyl 2'-deoxycytidine (See, e.g., U.S. Pat. Nos. 7,807,818 and 6,159,697, which are each incorporated herein by reference.);

5'-GTXGCCCCTTCTCCCXGCAGC-3' (SEQ ID NO: 1), wherein X is 5-methyl 2'-deoxycytidine;

ZTXGCCCCTTCTCCCXGCAZ-3' (SEQ ID NO: 6), wherein X is 5-methyl 2'-deoxycytidine and Z is 2'-deoxyguanosine methylphosphonate; and Antisense oligonucleotides described in U.S. Pat. No. 8,648,186 and International Patent Application Publication WO 2010/054826, each of which is incorporated herein by reference.

Contemplated antisense oligonucleotides include those comprising SEQ ID NO: 1: 5'-GTC* GCC CCT TCT CCC C*GC AGC-3', where C* represents 5-methyl-2'-deoxycytidine. In some embodiments, at least one of the internucleoside linkages of a contemplated antisense oligonucleotide is an O,O-linked phosphorothioate, for example, each of the 20 internucleoside linkages of SEQ ID NO: 1 may be an O,O-linked phosphorothioate. In some embodiments, the contemplated antisense oligonucleotide is an antisense oligonucleotide including the nucleic acid sequence of SEQ ID NO: 1, wherein each of the 20 internucleoside linkages is an O,O-linked phosphorothioate linkage, referred to herein as "Mongersen." In some embodiments, contemplated compositions disclosed herein may include a pharmaceutically acceptable salt, e.g., a sodium salt of the antisense oligonucleotide of SEQ ID NO: 1, that optionally may include 1 to 20 O,O-linked phosphorothioate internucleoside linkages. Contemplated salts of oligonucleotides include those that are fully neutralized, e.g., each phosphorothioate linkage is associated with an ion such as $Na^+$. Oligonucleotides may include naturally occurring nucleobases, sugars, and covalent internucleotide (backbone) linkages as well as non-naturally occurring portions. In various embodiments, the antisense oligonucleotides described herein, for example, the antisense oligonucleotides of SEQ ID NO: 1, SEQ ID NO: 4, and SEQ ID NO: 6, may include nucleotides comprising deoxycytidine and/or 5-methyl 2'-deoxycytidine, including, but not limited to, 5-methyl-2'-deoxycytidine 5'-monophosphate and 5-methyl-2'-deoxycytidine 5'-monophosphorothioate.

Contemplated anti-SMAD7 therapies include oligonucleotides that act against SMAD7 and may be administered orally. Disclosed therapies may, when administered orally to a subject suffering from IBD, deliver an effective amount of an antisense oligonucleotide to the intestinal system of a patient, e.g., deliver an effective amount of an antisense oligonucleotide to the terminal ileum and/or right colon of a patient.

In some embodiments of the invention, the anti-SMAD7 therapy, an antisense oligonucleotide against SMAD7, an additional therapeutic, or a combination thereof may be suitable for oral delivery of an antisense oligonucleotide, e.g., tablets, that include an enteric coating, e.g., a gastro-resistant coating, such that the compositions may deliver the antisense compound to, e.g., the terminal ileum and right colon of a patient. For example, such administration may result in a topical effect, substantially topically applying the antisense compound directly to an affected portion of the intestine of a subject. Such administration, may, in some embodiments, substantially avoid unwanted systemic absorption of the antisense compound.

For example, a tablet for oral administration may comprise granules (e.g., is at least partially formed from granules) that include a disclosed antisense compound or an antisense oligonucleotide against SMAD7, e.g., Mongersen, and in some embodiments an additional therapeutic, or a combination thereof; and pharmaceutically acceptable excipients. Such a tablet may be coated with an enteric coating. Contemplated tablets may include pharmaceutically acceptable excipients such as fillers, binders, disintegrants, and/or lubricants, as well as coloring agents, release agents, coating agents, sweetening, flavoring such as wintergreen, orange, xylitol, sorbitol, fructose, and maltodextrin, and perfuming agents, preservatives and/or antioxidants.

In some embodiments, contemplated pharmaceutical formulations include an intra-granular phase that includes a contemplated antisense compound or a pharmaceutically acceptable salt, e.g., Mongersen, and in some embodiments an additional therapeutic, and a pharmaceutically acceptable filler. For example, Mongersen and a filler may be blended together, with optionally other excipients, and formed into granules. In some embodiments, the intragranular phase may be formed using wet granulation, e.g., a liquid (e.g., water) is added to the blended antisense compound and filler, and then combination is dried, milled and/or sieved to produce granules. One of skill in the art would understand that other processes may be used to achieve an intragranular phase.

In some embodiments, contemplated formulations include an extra-granular phase, which may include one or more pharmaceutically acceptable excipients, and which may be blended with the intragranular phase to form a disclosed formulation.

An anti-SMAD7 therapy formulation or, in some embodiments, a formulation of an antisense oligonucleotide against SMAD7, an additional therapeutic, or a combination thereof, may include an intragranular phase that includes a filler. Exemplary fillers include, but are not limited to, cellulose, gelatin, calcium phosphate, lactose, sucrose, glucose, mannitol, sorbitol, microcrystalline cellulose, pectin, polyacrylates, dextrose, cellulose acetate, hydroxypropyl methylcellulose, partially pregelatinized starch, calcium carbonate, and others including combinations thereof.

In some embodiments, an anti-SMAD7 therapy formulation or, in other embodiments, a formulation of an antisense oligonucleotide against SMAD7, an additional therapeutic, or a combination thereof, may include an intragranular phase and/or an extragranular phase that includes a binder, which may generally function to hold the ingredients of the pharmaceutical formulation together. Exemplary binders include invention may be, but are not limited to, the following: starches, sugars, cellulose or modified cellulose such as hydroxypropyl cellulose, lactose, pregelatinized maize starch, polyvinyl pyrrolidone, hydroxypropyl cellulose, hydroxypropyl methylcellulose, low substituted hydroxypropyl cellulose, sodium carboxymethyl cellulose, methyl cellulose, ethyl cellulose, sugar alcohols and others including combinations thereof.

Contemplated anti-SMAD7 therapy formulations, or a formulation of an antisense oligonucleotide against SMAD7, an additional therapeutic, or a combination thereof, e.g., that include an intragranular phase and/or an extragranular phase, may include a disintegrant such as but are not limited to, starch, cellulose, crosslinked polyvinyl pyrrolidone, sodium starch glycolate, sodium carboxymethyl cellulose, alginates, corn starch, crosmellose sodium, crosslinked carboxymethyl cellulose, low substituted hydroxypropyl cellulose, acacia, and others including combinations thereof. For example, an intragranular phase and/or an extragranular phase may include a disintegrant.

In some embodiments, a contemplated anti-SMAD7 therapy formulation or a formulation of an antisense oligonucleotide against SMAD7, an additional therapeutic, or a combination thereof, includes an intra-granular phase comprising a disclosed antisense compound and excipients chosen from: mannitol, microcrystalline cellulose, hydroxypropyl methylcellulose, and sodium starch glycolate or combinations thereof, and an extra-granular phase comprising one or more of: microcrystalline cellulose, sodium starch glycolate, and magnesium stearate or mixtures thereof.

In some embodiments, a contemplated anti-SMAD7 therapy formulation or a formulation of an antisense oligonucleotide against SMAD7, an additional therapeutic, or a combination thereof, may include a lubricant, e.g., an extra-granular phase may contain a lubricant. Lubricants include but are not limited to talc, silica, fats, stearin, magnesium stearate, calcium phosphate, silicone dioxide, calcium silicate, calcium phosphate, colloidal silicon dioxide, metallic stearates, hydrogenated vegetable oil, corn starch, sodium benzoate, polyethylene glycols, sodium acetate, calcium stearate, sodium lauryl sulfate, sodium chloride, magnesium lauryl sulfate, talc, and stearic acid.

In some embodiments, the pharmaceutical formulation comprises an enteric coating. Generally, enteric coatings create a barrier for the oral medication that controls the location at which the drug is absorbed along the digestive track. Enteric coatings may include a polymer that disintegrates a different rates according to pH. Enteric coatings may include for example, cellulose acetate phthalate, methyl acrylate-methacrylic acid copolymers, cellulose acetate succinate, hydroxylpropyl methylcellulose phthalate, methyl methacrylate-methacrylic acid copolymers, ethylacrylate-methacrylic acid copolymers, methacrylic acid copolymer type C, polyvinyl acetate-phthalate, and cellulose acetate phthalate.

In some embodiments, the enteric coating includes an anionic, cationic, or neutral copolymer based on methacrylic acid, methacrylic/acrylic esters or their derivatives. In some embodiments, the enteric coating includes an ethylacrylate-methacrylic acid copolymer. Commercially available and exemplary enteric coatings include Opadry® AMB, Acryl-EZE®, Eudragit® grades. In some embodiments, an enteric coating makes up or may comprise about 5% to about 10%, about 5% to about 20%, about 8 to about 15%, about 8% to about 18%, about 10% to about 12%, or about 12% to about 16%, of a contemplated tablet by weight. For example, enteric coatings may include an ethylacrylate-methacrylic acid copolymer.

In one embodiment, the antisense oligonucleotide against SMAD7, the additional therapeutic, or the combination thereof may be a tablet for oral use comprising: about 0.5% to about 10% by weight of the active ingredients (e.g., Mongersen) or a pharmaceutically acceptable salt thereof; about 30% to about 50% by weight mannitol; and about 10% to about 30% by weight microcrystalline cellulose.

For example, an anti-SMAD7 therapy, or the antisense oligonucleotide against SMAD7, the additional therapeutic, or the combination thereof, in the form of a tablet is provided that comprises or consists essentially of about 0.5% to about 70%, e.g., about 0.5% to about 10%, or about 1% to about 20%, by weight of the active ingredients (for example, an antisense oligonucleotide or a pharmaceutically acceptable salt thereof (e.g., Mongersen)). Such a tablet may include for example, about 0.5% to about 60% by weight of mannitol, e.g., about 30% to about 50% by weight mannitol, e.g., about 40% by weight mannitol; and/or about 20% to about 40% by weight of microcrystalline cellulose, or about 10% to about 30% by weight of microcrystalline cellulose. For example, a contemplated tablet may comprise an intragranular phase that includes about 30% to about 60%, e.g., about 45% to about 65% by weight, or alternatively, about 5 to about 10% by weight Mongersen, about 30% to about 50%, or alternatively, about 5% to about 15% by weight mannitol, about 5% to about 15% microcrystalline cellulose, about 0% to about 4%, or about 1% to about 7% hydroxypropyl methylcellulose, and about 0% to about 4%, e.g., about 2% to about 4% sodium starch glycolate by weight.

Exemplary anti-SMAD7 therapy formulations include dosage forms that include or consist essentially of about 10 mg to about 500mg of Mongersen, for example, tablets that include about 10 mg, about 15 mg, about 20 mg, about 25 mg, about 30 mg, about 35 mg, about 40 mg, about 50 mg, about 60 mg, about 70 mg, about 80 mg, about 90 mg, about 100 mg, about 150 mg, about 160 mg, about 200 mg, or about 250 mg of Mongersen are contemplated herein. In one embodiment, the anti-SMAD7 therapy may be a tablet for oral use comprising: about 0.5% to about 10% by weight of an antisense oligonucleotide represented by SEQ ID NO: 1 or a pharmaceutically acceptable salt thereof; about 30% to about 50% by weight mannitol; and about 10% to about 30% by weight microcrystalline cellulose.

In an exemplary embodiment of the invention, a pharmaceutically acceptable tablet for oral administration is provided that includes an intra-granular phase that may comprise about 50% by weight Mongersen (or salt thereof), about 11.5% by weight mannitol, about 10% by weight microcrystalline cellulose, about 3% by weight hydroxypropyl methylcellulose, and about 2.5% by weight sodium starch glycolate; and an extra-granular phase that may comprise about 20% by weight microcrystalline cellulose, about 2.5% by weight sodium starch glycolate, and about 0.5% by weight magnesium stearate. The tablet may also include an enteric coating.

In another exemplary embodiment, a pharmaceutically acceptable tablet for oral administration is provided that includes or consists essentially of: an intra-granular phase that may comprise or consist essentially of about 5% to about 10%, e.g., about 8% by weight Mongersen (e.g., wherein the internucleoside linkages are each O,O-linked phophorothioates, and/or salt thereof, e.g., a sodium salt), about 40% by weight mannitol, about 8% by weight microcrystalline cellulose, about 5% by weight hydroxypropyl methylcellulose, and about 2% by weight sodium starch glycolate; and an extra-granular phase that may comprise about 17% by weight microcrystalline cellulose, about 2% by weight sodium starch glycolate, and about 0.4% by weight magnesium stearate.

Contemplated tablets may also include an enteric coating, e.g., a disclosed tablet may include about 13%, about 14%, about 15%, about 16%, about 17% by weight of an enteric coating, e.g., ethylacrylate-methacrylic acid copolymers (e.g., AcrylEZE®).

For example, the anti-SMAD7 therapy may be in the form of a pharmaceutically acceptable tablet for oral use comprising an intra-granular phase and extra-granular phase, wherein for example, the intra-granular phase comprises about 5% to about 10%, by weight (for example about 8% by weight) of an antisense oligonucleotide represented by SEQ ID NO: 1 or a pharmaceutically acceptable salt thereof (e.g., Mongersen), about 40% by weight mannitol, about 8% by weight microcrystalline cellulose, about 5% by weight hydroxypropyl methylcellulose, and about 2% by weight sodium starch glycolate, and for example, the extra-granular phase comprises about 17% by weight microcrystalline cellulose, about 2% by weight sodium starch glycolate, and about 0.4% by weight magnesium stearate, where the tablet may further comprise an enteric coating.

Contemplated formulations, e.g., tablets, in some embodiments, when orally administered to the patient may result in minimal plasma concentration of the oligonucleotide in the patient. In another embodiment, contemplated formulations, when orally administered to a patient, topically deliver to the terminal ileum and/or right colon of a patient, e.g., to an affected or diseased intestinal site of a patient.

Parenteral Administration

The pharmaceutical compositions of the invention can be formulated for parenteral administration, e.g., formulated for injection via the intravenous, intramuscular, subcutaneous, intralesional, or intraperitoneal routes. The preparation of an aqueous composition, such as an aqueous pharmaceutical composition containing an antisense oligonucleotide against SMAD7, an additional therapeutic, or a combination thereof, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. In addition, sterile, fixed oils may be employed as a solvent or suspending medium. For this purpose any bland fixed oil can be employed including synthetic mono- or diglycerides. In addition, fatty acids such as oleic acid can be used in the preparation of injectables. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In one embodiment, the antisense oligonucleotide against SMAD7, the additional therapeutic, or the combination thereof may be suspended in a carrier fluid comprising 1% (w/v) sodium carboxymethylcellulose and 0.1% (v/v) TWEEN™ 80. Under ordinary conditions of storage and use, these preparations contain a preservative to prevent the growth of microorganisms.

Injectable preparations, for example, sterile injectable aqueous or oleaginous suspensions may be formulated according to the known art using suitable dispersing or wetting agents and suspending agents. Generally, dispersions are prepared by incorporating the various sterilized active ingredients into a sterile vehicle which contains the basic dispersion medium and the required other ingredients from those enumerated above. Sterile injectable solutions of the invention may be prepared by incorporating an antisense oligonucleotide against SMAD7, an additional therapeutic, or a combination thereof in the required amount of the appropriate solvent with various of the other ingredients enumerated above, as required, followed by filtered sterilization. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The injectable formulations can be sterilized, for example, by filtration through a bacteria-retaining filter.

The preparation of more, or highly, concentrated solutions for intramuscular injection is also contemplated. In this regard, the use of DMSO as solvent is preferred as this will result in extremely rapid penetration, delivering high concentrations of the antisense oligonucleotide against SMAD7, the additional therapeutic, or the combination thereof to a small area.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

In an exemplary embodiment, a pharmaceutical composition for subcutaneous administration of an antisense oligonucleotide against SMAD7 comprises an antisense oligonucleotide such as that represented by SEQ ID NO:1, or a pharmaceutically acceptable salt thereof (such as a sodium salt, e.g., Mongersen), and a pharmaceutically acceptable carrier.

Dosing

Exemplary formulations include dosage forms that include about 10 mg to about 500 mg of an antisense oligonucleotide against SMAD7 optionally in combination with one or more additional therapeutics. For example, formulations that include about 10 mg to about 500 mg of Mongersen and tablets that include about 10 mg, about 15 mg, about 20 mg, about 25 mg, about 30 mg, about 35 mg, about 40 mg, about 50 mg, about 60 mg, about 70 mg, about 80 mg, about 90 mg, about 100 mg, about 150 mg, about 160 mg, about 200 mg, or about 250 mg of an antisense oligonucleotide against SMAD7 are contemplated herein. In one embodiment, a formulation may include about 40 mg, 80 mg, or 160 mg of an antisense oligonucleotide against SMAD7. In some embodiments, a formulation may include at least 100 µg of an antisense oligonucleotide against SMAD7. For example, formulations may include about 0.1 mg, 0.2 mg, 0.3 mg, 0.4 mg, 0.5 mg, 1 mg, 5 mg, 10 mg, 15 mg, 20 mg, or 25 mg of an antisense oligonucleotide against SMAD7. The amount administered will depend on variables such as the type and extent of disease or indication to be treated, the overall health and size of the patient, the in vivo potency of the antisense oligonucleotide, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Human dosage can be optimized, e.g., in a conventional Phase I dose escalation study designed to run from 40 mg to 160 mg. Dosing frequency can vary, depending on factors such as route of administration, dosage amount and the disease being treated. Exemplary dosing frequencies are once per day, once per week and once every two weeks. In some embodiments, dosing is once per day for 7 days.

Appropriate dosages for the additional agent or combinations will depend on the identity of the additional agent and can be determined by the skilled artisan.

Dosing can be varied as necessary depending on the clinical response of the subject. For example, a subject that has undergone remission can have dosing of one or more of the individual therapeutics reduced (e.g., by at least or about 2%, 5%, 8%, 10%, 12%, 15%, 20%, 25%, 30%, 35%, 40%, 50%, 60%, 65%, 70%, 75%, 80%, 85%, 88%, 90%, 92%, 95%, 98%, or 99%) as compared to the dosing prior to remission.

Administration

The antisense oligonucleotide and additional therapy can be administered at about the same time in the same or in separate dosage formations. If the antisense oligonucleotide and the additional therapy are administered in separate dosage formulations, the antisense oligonucleotide and the additional therapy can be administered in short succession, e.g., within 1 minute, within 3 minutes, within 5 minutes, within 10 minutes, within 15 minutes, within 20 minutes, within 30 minutes, within 45 minutes or within 1 hour of each other. The antisense olignucleotide and the additional therapy can be administered in any order, e.g., the antisense olignucleotide can be administered first or the additional therapy can be administered first.

The routes of administration of the antisense oligonucleotide and additional therapy can be the same (e.g., oral) or can be different (e.g., oral and parenteral). In certain embodiments, the anti-SMAD7 therapy is administered orally.

In other embodiments, a single therapeutic is started as a stand-alone therapy to which the second therapeutic is added (i.e., pretreatment with the single agent). For example, combination treatment methods can include one or more initial administrations of a stand-alone anti-SMAD7 therapy or stand-alone therapy with the one or more additional therapeutically effective agent. The initial administration(s) of stand-alone therapy, in some embodiments, are followed by combination treatments with the anti-SMAD7 therapy and the one or more additional therapeutically effective agent.

The length of pretreatment can be predetermined. For example, pretreatment may start about 12 hours, 1 day, 2 days, 3 days, 4 days, 7 days, 10 days, 14, days, 21 days, 28 days, 1 month, 1.5 months, 2 months, 2.5 months, 3 months, 4 months, 5 months, 6 months, 8 months, 10 months, 12 months, 15 months, 18 months, or 24 months prior to the administration of the additional therapeutic(s) in combination.

In other cases, the pretreatment period is based on the clinical response of the patient to the pretreatment. For example, a predetermined biomarker level or CDAI or UCAI score is reached before commencing the second therapeutic (e.g., any level or score described herein).

In particular embodiments, the pretreatment involves administration of a "subthreshold" level of the therapeutic, i.e., a dose lower than would typically be given when the therapeutic is used as a monotherapy. For example, the dose may be at least or about 2%, 5%, 8%, 10%, 12%, 15%, 20%, 25%, 30%, 35%, 40%, 50%, 60%, 65%, 70%, 75%, 80%, 85%, 88%, 90%, 92%, 95%, 98%, or 99% lower than that a dose that is typically given for the agent as a monotherapy.

The pretreatment using stand-alone therapy can sensitize the patient to the combination therapy. For example, the pretreatment may result in greater clinical efficacy using the combination, than if treatment is commenced with both therapies simultaneously or within a short (e.g., 1 day, 2 days, 3 days, 4 days, or 7 days) of each other. In particular embodiment, the pre-treatment can sensitize patients to the combination therapy that would other exhibit limited or no response to the combination therapy.

In cases where the combination therapy results in worse patient outcomes, the patient can be given a "rescue" therapy, which can include an immunosuppressant or a biologic (e.g., any of those described herein).

Synergy

Combination therapy can demonstrate synergistic improvements in efficacy as compared to the expected additive benefits of the two therapeutics individually. Synergy can be achieved using any of the dosing schemes described herein, e.g., where combination therapy is started at the same time (e.g., in the same or in different compositions), or where pretreatment using a stand-alone therapy (e.g., the anti-SMAD7 therapeutic or the additional agent) is employed.

Advantages associated with synergistic improvements in efficacy is that lower doses, less frequent doses, or a shorter duration of administration of one or both of the individual therapeutics can be used to treat the IBD. Dosing of an individual therapeutic can be reduced by at least or about 2%, 5%, 8%, 10%, 12%, 15%, 20%, 25%, 30%, 35%, 40%, 50%, 60%, 65%, 70%, 75%, 80%, 85%, 88%, 90%, 92%, 95%, 98%, or 99% as compared to the dosage used when the therapy is given as a monotherapy. In other cases, the frequency of dosing can be reduced, for example, to frequency that is less than or about 95%, 90%, 80%, 75%, 60%, 50%, 40%, 35%, 30%, 25%, 20%, 15%, or 10% of the frequency that would be employed for the monotherapy.

In addition, the duration of therapy can be reduced (e.g., by at least or about 2%, 5%, 8%, 10%, 12%, 15%, 20%, 25%, 30%, 35%, 40%, 50%, 60%, 65%, 70%, 75%, 80%, 85%, 88%, 90%, 92%, 95%, 98%, or 99%). In cases where the dosing is given in treatment cycles, e.g., where the therapy not given continuously, the "on" cycles can be shortened or the "off" cycles can be lengthened, e.g., by at least or about 2%, 5%, 8%, 10%, 12%, 15%, 20%, 25%, 30%, 35%, 40%, 50%, 60%, 65%, 70%, 75%, 80%, 85%, 88%, 90%, 92%, 95%, 98%, or 99%.

In some cases, the administration at the lower dose(s) permitted by the observed synergy can start at the same time as therapy is commenced. In other cases, higher doses of the therapeutics, e.g., those associated without synergy can be used initially. In these cases, the higher doses and be reduced, either gradually or stepwise over time. For example, doses can be reduced over a predetermined time period, or as the patient achieves certain measures of clinical response (e.g., any of those described herein).

In addition to allowing for lower doses, the combination therapy can also result in improved clinical efficacy. This may be observed in individual patients. For example, a patient receiving the combination therapy will show reduced disease symptoms as compared to the same patient when receiving a monotherapy. Alternatively, the efficacy improvements can be observed in a population of patients, for example, where the average clinical score of the patient population is improved relative to the monotherapy, or where a greater proportion of patients achieve a desired clinical threshold (e.g., disease remission). For example, the combination therapy may result in response or remission rates that are at least 5%, at least 10%, at least 15%, at least 20%, at least 25%, at least 30%, at least 35%, or at least 40% greater than response or remission rates of respective monotherapies.

In some cases, patients who are resistant to the anti-SMAD7 therapy or to the additional therapeutic exhibit sensitization upon administration of the combination of the invention to the patient. In particular cases, anti-SMAD7 therapy-resistant patients respond better to a combination therapy including an anti-SMAD7 therapy and one or more additional therapeutically effective agents than to a stand-alone therapy involving the administration of the one or more additional therapeutically effective agents. In other cases, patients resistant to one or more of the additional therapeutically effective agents can respond better to combinations of an anti-SMAD7 therapy and the one or more additional therapeutically effective agents than to anti-SMAD7 therapy standing alone.

Response to therapeutics can be determined by any means known in the art, e.g., using any of the biomarkers or indices described herein. Another advantage associated with synergy is a reduction in side effects. Because dosage can be reduced, any drug-related toxicity can likewise be reduced. Rate of occurrence or severity of side effects can also be reduced. Potential side effects of anti-SMAD7 therapy or the additional therapeutic agent include vomiting, nausea, anemia, cough, dyspepsia, increase in creatine phosphokinase, bronchitis, decreased appetite, sleepiness, aphthous stomatitis, fistula, leukopenia, abdominal abscess, abscess, acne, anal prolapse, anxiety, decrease in blood calcium, decrease in blood potassium, increase in blood urea, cholelithiasis, dental issues, depression, dry mouth, ear pain, endodontic procedure, extrasystoles, eyelid irritation, gastrointestinal motility disorder, hematochezia, hemorrhoids, hyperhidrosis, intestinal obstruction, jaundice, joint stiffness, myalgia, neck pain, oral herpes, palpitations, pruritus, tachycardia, thermal burn, tongue disorder, toothache, upper respiratory tract congestion, gastroenteritis, macrocytic anemia, anal fissure, back pain, chest discomfort, contusion, dermal cyst, dizziness, infectious erythema, increase in mean cell volume, increase in platelet count, and sub-occlusive symptoms. The reduction in drug toxicity, or occurrence or severity of side effects can be at least or about 2%, 5%, 8%, 10%, 12%, 15%, 20%, 25%, 30%, 35%, 40%, 50%, 60%, 65%, 70%, 75%, 80%, 85%, 88%, 90%, 92%, 95%, 98%, or 99%.

Additional Therapeutics

In some embodiments of the invention, the anti-SMAD7 therapy may be administered following or concurrently with other treatments, for instance, but not limited to, a steroid or steroids, an immunomodulator or immunomodulators, and/or mesalamine. The anti-SMAD7 therapy may be administered following or concurrently with any combination of these treatments. For instance, in some embodiments, the anti-SMAD7 therapy may be administered with only a steroid or steroids, only an immunomodulator or immunomodulators, only mesalamine, a steroid or steroids and an immunomodulator or immunomodulators, a steroid or steroids and mesalamine, or an immunomodulator or immunomodulators and mesalamine.

Examples of immunomodulators include azathioprine, mercaptopurine, methotrexate, cyclosporine A, and tacrolimus. Examples of steroids include corticosteroids, for example, prednisone, dexamethasone, hydrocortisone, methylprednisolone, prednisone, and budesonide. In some embodiments, a different salicylate, for example, sulfasalazine, may be administered in place of mesalamine. In some embodiments of the invention, the steroid(s), immunomodulator(s), or mesalamine may be administered by the same route as the anti-SMAD7 therapy (i.e., orally). In some embodiments of the invention the steroid(s), immunomodulator(s), or mesalamine may be administered by a different route than the anti-SMAD7 therapy. For instance, the steroid(s), immunomodulator(s), or mesalamine may be administered parenterally, rectally, intravenously, topically, or by inhalation spray.

The methods, kits, and compositions of the invention may include a therapeutic in addition to the anti-SMAD7 therapeutic. Such additional agents can include aminosalicylates, antibiotics, steroids, inflammatory cytokine antagonist, and immunomodulators, or combinations thereof. Exemplary agents are described in greater detail below.

In some embodiments, the anti-SMAD7 therapeutic can be combined with any additional therapeutic agent. In some embodiments, the anti-SMAD7 therapeutic can be combined with any additional therapeutic agent suitable for the treatment of IBD (e.g., CD or UC). In some embodiments, the additional therapeutic agent can include one or more of an aminosalicylate, an antibiotic, a steroid, an inflammatory cytokine antagonist and/or an immunomodulator. In some embodiments, the additional therapeutic agent does not include an aminosalicylate. In some embodiments, the additional therapeutic agent does not include and antibiotic. In some embodiments, the additional therapeutic agent does not include a steroid. In some embodiments, the additional therapeutic agent does not include an inflammatory cytokine antagonist. In some embodiments, the additional therapeutic agent does not include one or more of mesalamine, budenoside, and/or a systemically administered corticosteroid.

In some embodiments, the additional therapeutic agent is administered separately from the anti-SMAD7 therapeutic. In some embodiments, the additional therapeutic agent is administered first and the anti-SMAD7 therapeutic is administered second. For example, the additional therapeutic agent is administered more than 1 minute later, more than 3 minutes later, more than 5 minutes later, more than 10 minutes later, more than 15 minutes later, more than 20 minutes later, more than 30 minutes later, more than 45 minutes later, more than 1 hour later, more than 2 hours later, more than 3 hours later, more than 6 hours later, more than 9 hours later, more than 12 hours later, more than 18 hours later or more than 24 hours later than the anti-SMAD7 therapeutic. In some embodiments, the anti-SMAD7 therapeutic is administered first and the additional therapeutic agent is administered second. For example, the anti-SMAD7 therapeutic is administered more than 1 minute later, more than 3 minutes later, more than 5 minutes later, more than 10 minutes later, more than 15 minutes later, more than 20 minutes later, more than 30 minutes later, more than 45 minutes later, more than 1 hour later, more than 2 hours later, more than 3 hours later, more than 6 hours later, more than 9 hours later, more than 12 hours later, more than 18 hours later or more than 24 hours later than the additional therapeutic agent.

Aminosalicylates

In certain embodiments, the additional agents is an aminosalicylate. Particular examples of aminosalicylates include 5-aminosalicylic acid (5-ASA or mesalamine), sulfasalazine, balsalazide, and olsalazine. In generally, these compounds have anti-inflammatory effects.

In some embodiments, the aminosalicylates include 2-hydroxy-4-(4-(5-(2-methyl-3-phenylprop-2-enylidene)-4-oxo-2-sulfanylidene-1,3-thiazolidin-3-yl)butanoylamino)benzoic acid, 2-methoxy-5-amino-N-hydroxybenzamide, 3-methoxysalicylamine, 4-(N-(4-cyclohexylbenzyl)-2-(N,2,4,6-tetramethylphenylsulfonamido)acetamido)-2-hydroxybenzoic acid, 5-(7-hydroxy-3-O-phosphonocholyl)aminosalicylic acid, 5-aminomethylsalicylic acid, 5-aminosalicyl-glycine, 5-aminosalicyltaurine, acetyl 4-aminosalicylic acid, acetyl-4-dimethylaminosalicylic acid, acetyl-5-aminosalicylic acid, aminosalicylic acid, dersalazine, dextran-5-aminosalicylic acid, Dolo-Menthoneurin, ipsalazide, 2-hydroxy-5-(N-((2,5-dihydroxyphenyl)methyl)amino)benzoic acid 3-phenylpropyl ester, methyl 5-aminosalicylate, N-acetyl-5-aminosalicylic acid, N-glucopyranosyl-5-aminosalicylic acid, N-methacryloyl-5-aminosalicylic acid, N,N'-bis(5-aminosalicyl)cysteine, NOmesalamine, NSC 74859, olsalazine-O-sulfate, pasiniazide, phenyl 4-aminosalicylate, diethylamine salicylate, or UR 12746.

In some embodiments, compounds related to sulfasalazine include homosulfasalazine, methylsulfasalazine, salazodimethoxine, salazodin, salicylazoiminopyridine, susalimod, or TL-118.

Antibiotics

In certain embodiments, the additional therapeutic is an antibiotic. In some embodiments the antibiotic includes a penicillin, a cephalosporin, a polymyxin, a rifampicin, a lipiarmycin (fidaxomicin), a quinolone, a sulfonamide, a macrolide, a lincosamide, a tetracycline, a aminoglycoside, a cyclic lipopeptide, a glycylcycline, or an oxaindole.

Penicillins are a group of antibiotics that contain 6-aminopenicillanic acid with a side chain attached to the 6-amino group. In some embodiments, the penicillin includes benzylpenicillin, phenoxymethylpenicillin, benzathine benzylpenicillin, benzathine phenoxymethylpenicillin, penicillin G, penicillin G procaine, penicillin V, carfecillin, ampicillin, pivampicillin, carbenicillin, amoxicillin, carindacillin, bacampicillin, pivmecillinam, azlocillin, mezlocillin, piperacillin, ticarcillin, talampicillin, sulbenicillin, hetacillin, propicillin, pheneticillin, dicloxacillin, cloxacillin, meticillin, oxacillin, flucloxacillin, biapenem, apalcillin, aspoxicillin, ciclacillin, clemizole penicillin, imipenem, lenampicillin, nafcillin, or panipenem.

Cephalosprins are a class of β-lactam antibiotics originally derived from the fungus *Acremonium*. In some embodiments, the cephalosporin includes cefatrizine, cefamandole, cefuzoname, cefpimizole, cephapirin, cephaloridine, cefsulodin, cefotiam, ceforanide, ceftexzole, cefoxitin, latamoxef, flomoxef, cefmetazole, cefotetan, cefpiramide, cephaloglycin, cephalexin, cefadroxil, cefroxadine, ceferadine, cefaclor, or cefoperazone.

Polymyxins are antibiotics that, generally have structure consisting of a cyclic peptide with a long hydrophobic tail. They disrupt the structure of the bacterial cell membrane by interacting with its phospholipids and are selectively toxic for Gram-negative bacteria. In some embodiments, the polymyxin includes polysporin, neosporin, polymyxin B, polymyxin E, polymyxin S, or polymyxin T.

Rifampicin is a broad spectrum antibiotic derived from produced from *Streptomyces mediterranei* that inhibits DNA-dependent RNA polymerase activity. In some embodiments, the rifampicin includes 18,19-dihydrorifampicin, 21-(O-phosphoryl)rifampicin, 23-(O-(beta-glucopyranosyl))rifampicin, 23-(O-ribofuranosyl)rifampicin, 25-deacetylrifampicin, 25-desacetylrifapentine, 3-formyl-21-(O-phosphoryl)rifamycin SV, 3-formyl-23-(O-(beta-glucopyranosyl))rifamycin SV, 3-formyl-23-(O-ribofuranosyl) rifamycin SV, CGP 43371, CGS 24565, cotrifazid, dehydrorifampicin, DMB-rifampicin, Myrin P, rifamazid, rifampicin N-oxide, rifapentine, Rifaprim, rivicycline, or Sinerdol EH.

Quinolones are a class of synthetic antibiotics that inhibit bacterial DNA unwinding and replication. In some embodiments, the quinolone includes cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, delafloxacin JNJ-Q2, or nemonoxacin.

Antibacterial sulfanomides are a group of synthetic antimicrobial agents that contain the sulfonamide group. In some embodiments, the sulfonamide includes sulfacetamide, sulfadiazine, sulfadimidine, sulfafurazole, sulfisomidine (sulfaisodimidine), sulfadoxine, sulfamethoxazole, sulfamoxole, sulfadimethoxine, sulfamethoxypyridazine, sulfametoxydiazine, sulfadoxine, or sulfametopyrazine.

Macrolides are a group of compounds that include a macrocyclic lactone ring. In some embodiments, the macrolide includes azithromycin, clarithromycin, erythromycin, telithromycin, carbomycin A, josamycin, kitasamycin, midecamycin/midecamycin acetate, oleandomycin, solithromycin, spiramycin, troleandomycin, or tylosin/tylocine.

Lincosamides are a class of compounds that have contain a pyrrolidine ring linked via an amide-bond to a pyranose moiety. In some embodiments, the lincosamide includes 7-azido-7-deoxylincomycin, 7-deoxylincomycin, antibiotic Bu 2545, chloramlincomycin, Clindamycin, Linco-HAP, lincomycin sulfone, lincomycin sulfoxide, lincospectin, sparsolincomycin, Stomapin, dl-N-ethylclindamycin, mirincamycin, pirlimycin, or pirlimycin adenylate.

Tetracyline antibiotics have a naphthacene structure and inhibit amino acyl tRNA binding during protein synthesis. In some embodiments, the tetracycline antibiotic includes tetracycline, chlortetracycline, oxytetracycline, demeclocycline, semi-synthetic, lymecycline, meclocycline, methacycline, minocycline, and rolitetracycline.

Aminoglycoside antibiotics are a group of Gram-negative antibacterial therapeutic agents that inhibit protein synthesis. In some embodiments, the aminoglycoside antibiotic includes genatmicin, kanamycin A, amikacin, tobramycin, dibekacin, gentamicin, sisomicin, netilmicin, neomycins B and C, neomycin E (paromomycin), or streptomycin.

Cyclic lipopeptide antibiotics include a lipid moiety connected to peptide moiety. In some embodiments, the cyclic lipopeptide antibiotic includes daptomycin or battacin.

Glycylcyclines are class of antibiotics related to tetracycline and have a similar mechanism of action. In some embodiments, the glycylcycline includes tigecycline.

Oxazolidinones are class of antibiotics that usually include a 2-oxazolidone structure. They function by inhibiting tRNA binding to the ribosome. In some embodiments, the oxazolidinone includes linezolid, posizolid, torezolid, tedizolid, radezolid, or cycloserine.

In some embodiments, the antibiotic includes benzoyl peroxide, rifaximin, clofazimine, isoniazid, tinidazole, vancomycin, or metronidazole.

Steroids

In certain embodiments, the additional therapeutic is a steroid, for example, a corticosteroid. Corticosteroids can be naturally occurring or synthetic and are generally characterized by a by a hydrogenated cyclopentanoperhydrophenanthrene ring system. In some embodiments, the corticosteroid includes budesonide, dexamethasone (e.g., 21-acetate), betamethasone (e.g., 17-valerate), tixocortol pivalate, triamcinolone, triamcinolone (e.g., acetonide, acetonide 21-palmitate, diacetate, or hexacetonide), mometasone, amcinonide, desonide, fluocinonide, halcinonide, fluocortolone, hydrocortisone, fluticasone propionate, mometasone furotate, prednisone, prednisolone, beclomethasone (e.g., dipropionate (e.g., monohydrate)), flunisolide, or methylprednisolone (e.g., acetate or sodium succinate).

In some embodiments, the corticosteroid includes 6-hydroxydexamethasone, 9-fluorocortisone, a clobetasol (e.g., propionate), a clobetasone, a clocortolone (e.g., pivalate), a cortisone (e.g., acetate), a dichlorisone, a diflorasone (e.g., diacetate), diflucortolone, doxibetasol, flucmolone, a flumethasone (e.g., pivalate), a fluocinolone (e.g., acetonide), fluorohydroxyandrostenedione, a fluorometholone (e.g., acetate), fluoxymesterone, flupredidene, fluprednisolone, halometasone, halopredone, hydrocortisone, an isoflupredone (e.g., acetate), meclorisone, or a paramethasone (e.g., acetate).

Immunomodulators

In certain embodiments, the additional therapeutic is an immunomodulator, for example, an immunosuppressant. In some embodiments, the immunosuppressant includes a purine analog (e.g., azathioprine and 6-mercaptopurine), a folic acid analog (e.g., methotrexate), a pyrimidine analog (e.g., fluorouracil), or a cytotoxic antibiotic (e.g., dactinomycin, mitomycin C, bleomycin, mithramycin, anthracycline, and minocycline). In some embodiments, the immunosuppressant includes tacrolimus, mitoxantrone, cyclophosphamide, mycophenolate mofetil, or rapamycin.

Inflammatory Cytokine Antagonists

In certain embodiments, the additional therapeutic is an inflammatory cytokine antagonist, for example, an tumor necrosis factor (TNF) antagonist or an IL-10 antagonist. In some embodiments, the TNF antagonist includes infliximab, adalimumab, certolizumab pegol, golimumab, etanercept, pentoxifylline, or bupropion.

Methods of Monitoring Treatment

In some embodiments, the methods described herein entail monitoring the treatment, disease state, or biomarkers associated with a disease state of a patient having IBD. Monitoring treatment may be useful in terms of assessing treatment efficacy and safety, as well as evaluating the need to modulate treatment. Monitoring treatment may also be useful for evaluating whether the amount of SMAD7 antisense oligonucleotide being administered to a patient or which will be administered to a patient should be increased or decreased. Furthermore, monitoring treatment may be useful in terms of determining the amount or relative amount by which a dose of SMAD7 antisense oligonucleotide should be modulated, i.e., increased or decreased.

The effectiveness of a combination therapy in treating inflammatory bowel disease can be monitored using any appropriate approach. For example, any biomarker known to be associated with inflammatory bowel disease or excess SMAD7 activity can be used to monitor the effectiveness of the therapy in a patient, as can any subjective or objective clinical scale. Monitoring treatment may be useful in terms of assessing treatment efficacy and safety, as well as evaluating the need to modulate treatment. Monitoring treatment may also be useful for evaluating whether the amount of the antisense oligonucleotide against SMAD7, the additional therapeutic, or the combination thereof being administered to a patient or which will be administered to a patient should be increased or decreased or whether the therapy is effective. Furthermore, monitoring treatment may be useful in terms of determining the amount or relative amount by which a dose of the antisense oligonucleotide against SMAD7, the additional therapeutic, or the combination thereof should be modulated, e.g., increased or decreased.

Monitoring, for example, monitoring of CRP levels in a patient having IBD, may commence prior to, during, or after an initial dose of a SMAD7 antisense oligonucleotide. Furthermore, monitoring may continue after an initial dose. For example monitoring may be performed after administration of an initial dose. Monitoring may also be performed before, during, or after a subsequent dose of SMAD7 antisense oligonucleotide. Monitoring may be continuous or discontinuous such that monitoring may be performed at regular intervals, for example, after each dose of a SMAD7 antisense oligonucleotide is administered to a patient, before each dose of a SMAD7 antisense oligonucleotide is administered to a patient, or before and after each dose of a SMAD7 antisense oligonucleotide is administered to a patient.

Monitoring, for example, the level of a biomarker or a combination of biomarkers (e.g., CRP, TNFα, and IL8) in a patient having IBD, may commence prior to, during, or after an initial dose of the antisense oligonucleotide against SMAD7, the additional therapeutic, or the combination thereof. Furthermore, monitoring may continue after an initial dose. For example monitoring may be performed after administration of an initial dose. Monitoring may also be performed before, during, or after a subsequent dose of the antisense oligonucleotide against SMAD7, the additional therapeutic, or the combination thereof. Monitoring may be continuous or discontinuous such that monitoring may be performed at regular intervals, for example, after each dose of the antisense oligonucleotide against SMAD7, the additional therapeutic, or the combination thereof is administered to a patient, before each dose is administered to a patient, or before and after each dose is administered to a patient.

Monitoring may be performed multiple times in a single day (for instance, 2 times, 3 times, 4 times, about five times, or about 10 times in a single day), once a day, multiple times in a single week (for instance, 2 times, 3 times, 4 times, about five times, or about 10 times in a single week), once a week, multiple times in a single month (for instance, 2 times, 3 times, 4 times, about five times, or about 10 times in a single month), or once a month. In methods of the invention, monitoring may be performed at various times relative to an administering step. For instance, in some embodiments, monitoring may be performed immediately after, or at least 1 day, at least 3 days, at least 5 days, at least 1 week, at least 2 weeks, at least 3 weeks, at least 1 month, at least 2 months, at least 4 months, or at least 6 months after an administration step. In some embodiments, monitoring is performed about 15 days or about 28 days after an administration step.

As described above, the invention is based in part on the discovery that levels of CRP and other biomarkers can be used to evaluate and modify management and treatment with a SMAD7 antisense oligonucleotide in a patient having IBD. Thus, in embodiments of the invention, it is useful to know, determine, analyze, or compare levels of CRP and/or another biomarker in a patient or a sample from a patient having IBD. For example, in some instances it will be useful to know a threshold value for normal or abnormal levels of CRP and/or another biomarker in order to determine whether levels of the SMAD7 antisense oligonucleotide, the anti-SMAD7 therapy, the additional therapeutic, or the combination thereof, should be increased, decreased, or left untouched. In the methods described herein, a normal level of CRP may be tied to a specific value, for instance, a value of about 0.01 mg/L, about 0.05 mg/L, about 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, about 1.0 mg/L, about 1.5 mg/L, about 2.0 mg/L, about 2.5 mg/L, or about 3.0 mg/L. A normal level of TNFα may be about 11 μg/L (e.g., 11.2 μg/L), or may be another value (e.g., 5, 6, 7, 8, 9, 10, 12, 13, 14, or 15 μg/L), depending on the control subject in serum. A normal level of IL8 in serum may be about 13 μg/L (e.g., 12.9 μg/L), or may be another value (e.g., 6, 7, 8, 9, 10, 11, 12, 14, 15, 16, or 17 µg/L), depending on the control subject. See, e.g., Arican et al., Mediators Inflamm. 2005:273, 2005. In some embodiments, a normal level of CRP and/or another biomarker may be determined by comparison to median levels of CRP and/or another biomarker in a healthy control group that is matched to the patient with respect to various factors, for example, age, gender, ethnic origin, smoking habits, dietary habits, body-mass index (BMI), and/or exercise habits.

Levels of CRP and/or other analytes may be determined by obtaining a sample from the patient. Levels of a biomarker or combination of biomarkers (e.g., CRP, TNFα, and IL8) may be determined by obtaining a sample from the patient. According to the methods described herein, a sample may be a tissue sample (e.g., a gastrointestinal tissue sample) or a bodily fluid sample (e.g., a saliva sample, a stool, a urine sample, or any liquid biopsy). Samples may include solid tissue biopsies that contain CRP-expressing or other biomarker-expressing cells, for example, epithelial colon tissue cells. A sample can be a sample obtained from a patient tissue biopsy, for example, a mucosal tissue biopsy, for example, an intestinal mucosal tissue biopsy. Furthermore, the sample may be a blood, serum, or plasma sample. A blood sample from a subject may be obtained using techniques well-known in the art. Blood samples may include peripheral blood mononuclear cells (PMBCs), RBC-depleted whole blood, or blood serum. PBMCs can be separated from whole blood samples using different density gradient (e.g., Ficoll density gradient) centrifugation procedures. For example, whole blood (e.g., anticoagulated whole blood) is layered over the separating medium and centrifuged. At the end of the centrifugation step, the following layers are visually observed from top to bottom: plasma/platelets, PBMC, separating medium and erythrocytes/granulocytes.

Samples may also be obtained or extracted from the patient based on temporal parameters. For instance, samples may be taken from the same patient at different time points, for example, about every 30 minutes, about every hour, about every three hours, about every 6 hours, or about every 12 hours, throughout a given time period, for example, about 1 hour, about 6 hours, about 12 hours, about 1 day, about 3 days, about 1 week, or about 1 month. Samples may also be taken after individual meals, for example, immediately after, about 30 minutes after, about 1 hour after, about 2 hours after, about 3 hours after, about 4 hours after, about 5 hours after, or about 6 hours after a meal.

Methods of monitoring treatment may also include methods of monitoring other factors, including, but not limited to levels of other biomarkers or analytes (e.g., CRP, TNFα, IL8), CDAI score, clinical remission, and presence or severity of IBD symptoms.

In embodiments of the invention where levels of an analyte, a biomarker or a combination of biomarkers (e.g., CRP, TNFα, and IL8) are measured, various methods may be used to measure the biomarker or analyte. The level of an analyte or biomarker, for example, IL8, TNFα, or CRP, may be determined using any method known in the art, including, but not limited to, immunochemistry and/or by nucleotide analysis.

For example, the amount of CRP and/or another biomarker in a blood or tissue sample, or a fraction of a blood or tissue sample of a known volume may be determined by immunochemistry. Methods of determining biomarker or analyte concentration by immunochemistry include, but are not limited to, Western blotting, ELISA, and immunostaining methods. In some embodiments, a method of determining biomarker or analyte concentration by immunochemistry is performed using an antibody that can bind to the biomarker or analyte of interest, for instance, an anti-CRP antibody or an antibody directed against the biomarker. Assaying biomarker or CRP concentration by immunochemistry requires, for example, at least one antibody against a biomarker or a CRP protein, e.g., at least one anti-CRP antibody. A primary antibody may be tagged with a detectable label, e.g., a fluorescent marker. Alternatively, a secondary antibody tagged with a detectable label, e.g., a fluorescent marker, that binds specifically to the species isotype of the primary antibody may be used to perform immunochemistry. Methods of determining biomarker or analyte concentration by immunochemistry may also involve the use of buffers, blocking reagents, unconjugated primary antibodies, and primary and/or secondary antibodies conjugated to tags that allow for antibody detection, such as fluorescent probes or substrate-specific enzymes.

Methods of determining biomarker or analyte concentration by nucleotide analysis include, but are not limited to, methods of analyzing biomarker or analyte mRNA transcript levels such as Northern blotting and polymerase chain reaction methods, for example, quantitative polymerase chain reaction methods. Nucleotide analysis may be performed using an oligonucleotide probe that binds a biomarker or analyte nucleotide sequence (e.g., a CRP, TNFα, or IL8 nucleotide sequence) or a pair of oligonucleotide primers capable of amplifying an analyte or biomarker nucleotide sequence via a polymerase chain reaction, for example, by a quantitative polymerase chain reaction. Oligonucleotide probes and oligonucleotide primers may be linked to a detectable tag, such as, for example, a fluorescent tag. In determining analyte or biomarker concentration by nucleotide analysis, the practitioner may evaluate a particular analyte's or biomarker's mRNA transcript concentration in a sample. Alternatively, in determining analyte or biomarker concentration by nucleotide analysis, the practitioner may establish a correlation between a particular analyte's or biomarker's mRNA transcript abundance and the particular analyte's or biomarker's protein abundance in order to extrapolate analyte or biomarker protein concentration based on a measure of analyte or biomarker mRNA transcript abundance.

Methods of the claimed invention include steps that may be carried out in vitro. For instance, it is contemplated that the steps of measuring CRP and/or other biomarker levels in the subject, determining the levels of CRP and/or other biomarkers in a sample, and/or determining CDAI score or taking measurements necessary to determine CDAI score may be carried out in vitro. For example, the level of CRP and/or another biomarker in a sample may be determined by performing immunochemistry or nucleotide analysis on the sample in vitro. Examples of contemplated in vitro assays include, but are not limited to, time-resolved fluorescence resonance energy transfer assays (TR-FRET; e.g., Cisbio HTRF®), surface plasmon resonance assays (e.g., Biacore® surface plasmon resonance array systems), real-time polymerase chain reaction (RT-PCR), and cell-based assays (e.g., reporter cell-based assays). Alternatively, in some embodiments of the invention, the steps of determining and analyzing the CRP and/or other biomarker levels in a patient having IBD, determining and analyzing the CRP and/or other biomarker levels in a sample, and/or determining CDAI score or taking measurements necessary to determine CDAI score may be carried out in vivo.

A primary clinical endpoint can include, e.g., the achievement of clinical remission or maintenance of clinical remission for a period of time (e.g., 1 week, 2 weeks, 1 month, 2 months, 3 month, 6 months, or 1 year), as determined by a physician, e.g., on the basis of the Crohn's Disease Activity Index (CDAI) or the Ulcerative Colitis Activity Index (UCAI). For example, a clinical endpoint could be the achievement of a CDAI score <150, <125, <100, or <75 in a patient; a certain maximum CDAI score can will not be exceeded, e.g., for at least 1 week, 2 weeks, 1 month, 2 months, 3 month, 6 months, or one year).

A secondary clinical endpoint can include, e.g., the observation of a clinical response, as determined by a physician, e.g., on the basis of an observed improvement in a CDAI score or UCAI of at least 50 points, 75 points, 100 points, 125 points, or 150 points. In certain embodiments, the clinical response is observed within a certain period of time, e.g., within 1 week, 2 weeks, 3 weeks, 1 month, or 2 months from the first administration of a combination treatment.

Anti-IL8 antibodies suitable for immunochemistry are commercially available, including, but not limited to, goat anti-human IL8 from Abcam (Cat. No. ab10769), mouse anti-human IL8 from Santa Cruz (Cat. Nos. sc-73321, sc-52870, and sc-7302), mouse anti-human IL8 (3IL8-H10) from Pierce (Cat. No. M801), and a mouse anti-human IL8 from Sigma-Aldrich (Cat. No. WH0003576M5) antibody.

Anti-TNFα antibodies suitable for immunochemistry are commercially available, including, but not limited to, rabbit anti-human TNFα from Abcam (Cat. No. ab9635), rabbit anti-human TNFα from Cell Signaling Technology (Cat. No. 3707), mouse anti-human TNFα from affymetrix eBioscience (Cat. No. 14-7348-81), and rabbit anti-human TNFα from Rockland Antibodies & Assays (Cat. No. 209-401-306S) antibody.

Anti-CRP antibodies suitable for immunochemistry are commercially available, such as, for example, goat anti-human CRP polyclonal antibodies from Santa Cruz Biotechnology (Catalog Numbers sc-18304 and sc-18306), a rabbit anti-human CRP polyclonal antibody from from Santa Cruz Biotechnology (Catalog Number sc-30047), a mouse anti-human CRP monoclonal antibody from Santa Cruz Biotechnology (Catalog Number sc-70883), a mouse anti-human CRP monoclonal antibody from Sigma-Aldrich (Catalog Number C1688-.2ML), a rabbit anti-human monoclonal antibody from abcam (Catalog Number ab32412), a mouse anti-human CRP monoclonal antibody from abcam (Catalog Number ab13426), and a goat anti-human CRP polyclonal antibody from Thermo Scientific (Catalog Number G0301-1B).

Enzyme-Linked Immunosorbent Assay

In some embodiments, CRP concentration may be determined by Enzyme-linked immunosorbent assay (ELISA). Specifically, levels of CRP in a sample, especially a blood sample, for example, a blood serum sample, can be determined by ELISA. Assaying CRP concentration by ELISA requires at least one antibody against CRP protein, e.g., at least one anti-CRP antibody, and/or at least one secondary antibody, e.g., at least one labeled secondary antibody. In some embodiments, the anti-CRP antibody is labeled with, e.g., a fluorescent label. In certain embodiments, the anti-CRP antibody is not labeled and a secondary antibody capable of binding the species isotype of the primary antibody is labeled, e.g., with a fluorescent probe or enzyme capable of reacting with a specific substrate, thereby providing a detectable signal.

Performing an ELISA requires at least one capture antibody, at least one detection antibody, and/or at least one enzyme-linked or fluorescent labeled secondary antibody. For example, assaying CRP levels by ELISA may require an anti-CRP antibody as the capture antibody. The anti-CRP antibody is immobilized on a solid support such as a polystyrene microtiter plate. A sample, for example, a blood serum sample is then added and allowed to complex with the bound antibody. Unbound serum components are removed with a wash. A detection antibody, e.g., a different anti-CRP antibody, e.g., an anti-CRP antibody that binds to a different portion of the CRP protein than the capture antibody, is added and is allowed to bind to the captured CRP. The detection antibody is linked to a detectable tag, such as an enzyme, either directly or indirectly, e.g., through a secondary antibody that specifically recognizes the detection antibody. Typically between each step, the plate, with bound protein, is washed with a wash buffer, e.g., a mild detergent solution. Typical ELISA protocols also include one or more blocking steps, which involve use of a non-specifically-binding protein such as bovine serum albumin to block unwanted non-specific binding of protein reagents to the plate. After a final wash step, the plate is developed by addition of an appropriate enzyme substrate, to produce a visible signal, which indicates the amount of CRP protein in the sample. The substrate can be, e.g., a chromogenic substrate or a fluorogenic substrate. ELISA methods, reagents and equipment are well-known in the art and commercially available.

Numerous anti-CRP antibodies suitable for ELISA are commercially available, such as, for example, a mouse anti-human CRP monoclonal antibody from abcam (Catalog Number ab13426), a mouse anti-human CRP monoclonal antibody from Sigma-Aldrich (Catalog Number C1688-.2ML), a rabbit anti-human CRP polyclonal antibody from from Santa Cruz Biotechnology (Catalog Number sc-30047), a goat anti-human CRP polyclonal antibody from Thermo Scientific (Catalog Number G0301-1B), and a goat anti-human CRP polyclonal antibody from Santa Cruz Biotechnology (Catalog Number sc-18306).

Nucleotide Analysis

In some embodiments, CRP concentration may be determined by performing a "nucleotide analysis." A nucleotide analysis may include analysis of CRP nucleotide transcript levels (e.g., CRP mRNA transcript levels) in a sample, for example, a blood sample. CRP transcript levels may be determined by Northern blot, for example, a quantitative Northern blot; or polymerase chain reaction, for example, a quantitative polymerase chain reaction. Reagents necessary to perform Northern blot include oligonucleotide probes, for example, oligonucleotide probes linked to a detectable label. Detectable labels may include fluorescent labels or enzymes capable of reacting with a specific substrate. Reagents necessary to perform polymerase chain reaction include oligonucleotide primers capable of specifically binding to a CRP mRNA transcript and amplifying the number of CRP mRNA transcripts by polymerase chain reaction. Oligonucleotide primers may be linked to a detectable label to enable, for example, quantitative polymerase chain reaction. Other reagents necessary to perform quantitative polymerase chain reaction include, but are not limited to, primers capable of amplifying a control transcript signal, for instance, a β-tubulin transcript signal. Buffers, reagents (including oligonucleotide primers and probes), techniques, and equipment necessary for performing Northern blotting and polymerase chain reactions are readily available and are well-known in the art.

Test Kits

The invention includes a test kit comprising certain components for performing the methods disclosed herein. A test kit may enhance convenience, speed and reproducibility in the performance of the disclosed methods. An exemplary kit may include detailed instructions for measuring a CDAI index score in a subject.

An exemplary immunochemistry-based test kit may contain materials for determining CRP protein levels by immunochemistry, for example, by ELISA or by Western blotting. An immunochemistry kit, for example, may contain a primary antibody against CRP and a secondary antibody conjugated to a reporter enzyme, e.g., horseradish peroxidase, or a fluorescent probe. In other embodiments, the test kit contains not only antibodies, but also buffers, reagents and detailed instructions for determining CRP concentration in a sample. Such a kit may include detailed instructions for measuring a CDAI index score in a subject.

In another embodiment, a test kit may contain materials for determining CRP mRNA transcript levels by polymerase chain reaction, for example, by quantitative polymerase chain reaction, or by Northern blotting, for example, by quantitative Northern blotting. A kit for determining CRP mRNA transcript levels by Northern blotting may include oligonucleotide probes, for example, oligonucleotide probes linked to a detectable label. Detectable labels may include fluorescent labels or enzymes capable of reacting with a specific substrate. A kit for determining CRP mRNA transcript levels by polymerase chain reaction may include oligonucleotide primers capable of specifically binding to a CRP mRNA transcript and amplifying the number of CRP mRNA transcripts by polymerase chain reaction. Oligonucleotide primers may be linked to a detectable label to enable, for example, quantitative polymerase chain reaction. Other reagents necessary to perform quantitative polymerase chain reaction including, but not limited to, primers capable of amplifying a control transcript signal, for instance, a beta tubulin transcript signal, may be included in the kit. In other embodiments, the kit for determining CRP mRNA transcript levels contains not only oligonucleotide primers and/or oligonucleotide probes, but also buffers, reagents and detailed instructions for determining CRP mRNA transcript levels in a sample. Such a kit may include detailed instructions for measuring a CDAI index score in a subject.

Methods of Selecting and Treating Patients

The therapeutic combination of the invention can be administered to any patient that is need of treatment for IBD or at increased risk of developing IBD. Because SMAD7 is known to be associated with inflammation in inflammatory bowel disorders such as ulcerative colitis and Crohn's disease, it can be beneficial to reduce SMAD7 activity in such patients.

The compositions and methods of the invention can be used to treat patients that are resistant to one or more of the individual therapeutics described herein, and in some cases, the combination therapy can be used to overcome the patient's resistance to the single therapeutic. In a particular example, the patient may be steroid-resistant and administration of the combination of the anti-SMAD7 therapeutic in combination with a steroid (e.g., a corticosteroid) may be used to overcome steroid resistance. In other cases, the patient is resistant to another therapeutic used to treat IBD, e.g., an anti-SMAD7 therapy.

In particular embodiments, the patient is a subject identified as having altered levels of a biomarker that is associated with IBD or with inflammation. For example, the patient may have elevated levels of interleukin-8 (IL-8), tumor necrosis factor-α (TNF-α), or C-reactive protein (CRP) relative to a normal control or a normal control value.

The invention described herein provides methods of selecting and treating patients in part by selecting patients that show some likelihood of responsiveness to SMAD7-antisense therapy. In particular embodiments, a patient is selected if the patient shows some likelihood of responsiveness to anti-SMAD7 therapy. Likeliness of responsiveness to anti-SMAD7 therapy is premised in part on determining levels of CRP, TNFα, and/or IL8 in a patient with IBD, for example, preexisting levels of CRP, TNFα, and/or IL8 (i.e., levels of CRP, TNFα, and/or IL8 in a patient prior to administration of an initial dose of a SMAD7 antisense oligonucleotide) or levels of CRP, TNFα, and/or IL8 determined after an initial dose or one or more subsequent doses of SMAD7 antisense oligonucleotide. For instance, in some embodiments of the invention, a patient will be selected for treatment or further treatment with a SMAD7 antisense oligonucleotide after detecting or analyzing absolute or relative CRP, TNFα, and/or IL8 levels or changes in CRP, TNFα, and/or IL8 levels. Levels of CRP, TNFα, and/or IL8 in a patient with IBD may be compared to a normal level of CRP, TNFα, and/or IL8, for example, normal levels of CRP, TNFα, and/or IL8 as defined by median CRP, TNFα, and/or IL8 levels in a matched control group or absolute levels of CRP, TNFα, and/or IL8. Levels of CRP, TNFα, and/or IL8 in a patient with IBD may also be compared to a threshold CRP, TNFα, and/or IL8 level, for example, a threshold CRP, TNFα, and/or IL8 level that is elevated relative to a normal CRP, TNFα, and/or IL8 level. In certain embodiments, a patient is selected for treatment with anti-SMAD-7 therapy if the CRP level in the blood is greater than 3.0 mg/ml, greater than 3.5 mg/ml, or greater than 4.0 mg/ml.

In some embodiments, a patient will be selected for treatment or further treatment with a SMAD7 antisense oligonucleotide if the levels of CRP, TNFα, and/or IL8 in the patient are more than 10%, 20%, 30%, 40%, 50%, 60%, 70%, 80%, 90%, or 100% elevated relative to the average, median or mean levels of CRP, TNFα, and/or IL8 in a matched control group.

In some embodiments, a patient will be selected for treatment or further treatment with a SMAD7 antisense oligonucleotide if the level of CRP, TNFα, and/or IL8 in the patient are more than 2-fold, more than 3-fold, more than 4-fold, more than 5-fold, more than 6-fold, more than 7-fold, more than 8-fold, more than 9-fold or more than 10-fold elevated relative to the average, median or mean levels of CRP, TNFα, and/or IL8 in a matched control group.

Typically, CRP, TNFα, and/or IL8 levels will be measured in terms of a concentration, for instance, mass of CRP, TNFα, and/or IL8 protein, peptide, or RNA per volume of sample, for example, volume of blood or tissue. Thus selection of patients for initial or continued treatment is tied to CRP, TNFα, and/or IL8 levels in the patient, such that, for example, high initial levels of CRP, TNFα, and/or IL8 may indicate a potential for responsiveness to SMAD7 antisense oligonucleotide treatment. Furthermore, high levels of CRP, TNFα, and/or IL8 (i.e., above normal levels of CRP, TNFα, and/or IL8) may indicate a need for increased doses of SMAD7 antisense oligonucleotide, whereas normal or below normal levels of CRP, TNFα, and/or IL8 may indicate a need for decreased or unchanged doses of SMAD7 antisense oligonucleotide, especially following one or more doses. Alternatively, continued levels of above normal levels of CRP, TNFα, and/or IL8 after repeated doses may indicate that the patient is not responsive to treatment.

Thus, if levels of CRP are above normal levels of CRP, a patient may be administered an initial and/or subsequent dose of SMAD7 antisense oligonucleotide. In some embodiments, CRP levels are already known to be above normal CRP levels prior to administration of an initial dose. In some embodiments, CRP levels in a patient with IBD will be determined prior to administration of an initial dose. In some embodiments, after an initial dose of SMAD7 antisense oligonucleotide, if CRP levels are analyzed and determined to be above normal levels of CRP, the patient will be administered a subsequent dose of SMAD7 antisense oligonucleotide, for instance a greater dose than the initial dose. Alternatively, if CRP levels are analyzed and determined to be below normal levels of CRP, the patient may be administered a subsequent dose of SMAD7 antisense oligonucleotide, for instance an equal or smaller dose than the initial dose.

In yet other embodiments, CRP levels may be analyzed and determined in a patient with IBD, and then an initial dose of SMAD7 antisense oligonucleotide may be administered to the patient if the CRP levels are above normal levels of CRP. Furthermore, in some embodiments, after an initial dose of SMAD7 antisense oligonucleotide, levels of CRP may be determined, and if the levels of CRP are above normal levels of CRP then a subsequent dose of SMAD7 antisense oligonucleotide that is greater than or equal to the initial dose may be administered to the patient. Alternatively, after an initial dose of SMAD7 antisense oligonucleotide, levels of CRP may be determined, and if the levels of CRP are below normal levels of CRP then a subsequent dose of SMAD7 antisense oligonucleotide that is smaller than or equal to the initial dose may be administered to the patient.

In yet other embodiments, the invention provides methods whereby: CRP levels may be analyzed and determined in a patient with IBD; an initial dose of SMAD7 antisense oligonucleotide may be administered to the patient if the CRP levels are above normal levels of CRP; the levels of CRP are analyzed after the initial administration; and if the level of CRP after the initial dose is administered is lower than the level of CRP before the initial dose is administered, then the patient is administered a subsequent dose that is the same as the initial dose or smaller than the initial dose. Alternatively, if the level of CRP is unchanged or increased after the initial dose is administered compared to the level of CRP before the initial dose is administered, then the patient is administered a subsequent dose that is greater than the initial dose or treatment is terminated.

Thus, the contemplated invention provides different methods for treating and managing IBD in a patient by accounting for multiple treatment scenarios based on analysis and determination of CRP levels and patient responsiveness to SMAD7 antisense oligonucleotide administration.

For instance, if after administration of a SMAD7 antisense oligonucleotide CRP levels in a patient are above normal CRP levels, treatment can continue at the same dose or at an increased dose of the SMAD7 antisense oligonucleotide.

If after administration of a SMAD7 antisense oligonucleotide CRP levels in a patient are below normal CRP levels, treatment can continue at the same dose or at a decreased dose of the SMAD7 antisense oligonucleotide.

If after an initial dose and one or more subsequent doses of a SMAD7 antisense oligonucleotide CRP levels continue to be above or below normal CRP levels, the treatment may be terminated. For example, treatment may be terminated either because the patient is in remission, because the patient is not responsive to treatment, or the patient has been administered the maximum tolerated dose.

In some instances, if CRP levels decrease in a patient following one or more doses of the SMAD7 antisense oligonucleotide, this may indicate that a patient is responsive to treatment. In these patients, subsequent doses of the SMAD7 antisense oligonucleotide may be administered but at the same dose or a smaller dose compared to the previous dose(s).

In some instances, if CRP levels are stable or increase following an initial or one or more subsequent doses of the SMAD7 antisense oligonucleotide, this may indicate that a patient is not responsive to treatment. In these patients, subsequent doses of the SMAD7 antisense oligonucleotide may be administered but at a greater dose compared to the previous dose(s). Alternatively, the treatment can be discontinued, for example, if the dose approaches the maximum tolerated dose.

In some instances, if a patient achieves clinical remission, as determined by clinical factors other than CRP levels, but CRP levels remain essentially unchanged or above normal after administration of a SMAD7 antisense oligonucleotide, then the SMAD7 antisense oligonucleotide treatments may be terminated. In such a case, CRP levels may not be indicative of IBD progression, but may be elevated due to other factors, e.g., another inflammatory disease.

EXAMPLES

The invention is further illustrated by the following examples. The examples are provided for illustrative purposes only, and are not to be construed as limiting the scope or content of the invention in any way.

Example 1

Design of a Phase 2 Clinical Trial to Evaluate Safety and Efficacy of an Anti-SMAD7 Antisense Treatment in CD Patients A phase 2 clinical trial was conducted to evaluate the safety and efficacy of an anti-SMAD7 antisense treatment in patients with CD. Male or female CD patients eligible for the trial were 18-75 years old and had a CDAI score ranging from 220 to 400 for at least one week prior to enrollment. Patients enrolled in the trial had inflammatory lesions in the terminal ileum and/or right colon and were steroid-dependent and/or steroid-resistant. Concomitant mesalamine and steroid therapy was maintained during the clinical trial at a stable dose in patients already receiving those drugs. Eligible patients had the option of continuing to take immunomodulators (e.g., azathioprine, mercaptopurine, methotrexate) if such therapy had begun at least 6 months before the treatment phase of the study commenced, and the patients did not receive treatment with anti-TNF-α antibodies or other biologics during the 90 days prior to enrollment in the trial.

The anti-SMAD7 therapy evaluated in the trial was an oral dosage form that included an enteric coating which allowed targeted topical delivery of the anti-SMAD7 antisense oligonucleotide Mongersen to the terminal ileum and right colon. Because the active compound of the oral dosage form of Mongersen was released in the terminal ileum and right colon, patients with lesions in the stomach and/or the proximal small intestine and/or the transverse and/or left colon were excluded from the trial. Patients were also excluded if they had strictures, fistulae or perianal disease or if they had extraintestinal manifestations. Patients were also excluded if they had active or recent infections or a history of malignancy. Patients were also excluded from the trial if they had undergone proctocolectomy or intestinal resection resulting in the short-bowel syndrome, or had experienced a clinically significant abnormality on an electrocardiogram or clinically significant laboratory abnormalities. Women who were pregnant or breast-feeding were also excluded. Female patients enrolled in the trial were required to use two forms of contraception throughout the study period.

The study was conducted as a multicenter, randomized, placebo-controlled, double-blind, phase 2 clinical trial. After providing written informed consent, patients entered a 9-day screening phase to determine eligibility and pre-treatment measurements. Patients were screened for eligibility at 17 centers in Italy and Germany after the local institutional review boards and ethics committees had approved the clinical trial protocol. Patients who were determined eligible for the trial were randomly assigned into active treatment and placebo groups. The trial included 1 placebo group and 3 experimental groups receiving varying doses of Mongersen (10 mg/day, 40 mg/day, and 160 mg/day). Patients were assigned to these groups in a 1:1:1:1 ratio, using an independent, computer-generated randomization schedule without stratification or block allocation. The three doses of the active drug were selected based on data generated by pre-clinical, toxicology and phase 1 studies. The four groups of patients received treatment of either placebo or one of the three doses of Mongersen for two weeks (i.e., days 1-14). Following the two week treatment, patients were evaluated on days 15, 28, and 84 (i.e., 1 day after stopping treatment, 2 weeks after stopping treatment, or 10 weeks after stopping treatment).

The study used different measurements to determine efficacy of treatment with Mongersen in IBD patients enrolled in the trial. Rates of remission, defined as a CDAI score of less than 150 at day 15 and maintained for at least 2 weeks, were assessed in patients. Rates of clinical response—defined as a decrease in patient CDAI score of at least 100 or 70 points as evaluated on day 15 or day 28 (i.e., 1 day or 2 weeks, respectively, after stopping drug treatment)—were also evaluated. The number of patients with a CDAI score less than 150 at each time point (i.e., day 15, 28, and 84) was also evaluated. Patient CDAI scores were measured before treatment and during the week preceding days 15, 28, and day 84. The percentage of patients who achieved normalization of CRP levels (i.e., CRP concentration of less than 3.0 mg/liter) at the end of treatment was also determined. Finally, the percentage of patients who had elevated CRP levels (i.e., greater than 3.0 mg/liter) before treatment and who also reached clinical remission was evaluated.

Patients who experienced disease worsening (≥70 CDAI score increase) could receive rescue therapy with biologics and/or immunosuppressive drugs after the 2-week treatment period. Six patients (two in the placebo group, one in the 10 mg/day Mongersen group, and three in the 160 mg/day Mongersen group) received rescue therapy with biologics and/or immunosuppressive drugs due to a worsening of disease after day 28 and were considered non-responders (CDAI >150) in the analysis of the secondary endpoints. Patients who were in clinical remission after the 2-week treatment period (CDAI <150 at both day 14 and day 28) could taper steroids.

Safety of Mongersen treatment was also assessed. Changes in clinical, biochemical, and hematologic variables were assessed on days 1, 7, 15, 28, and 84. ELISA was used to monitor complement activation in patients. Instances of adverse events (AE) that occurred during the trial were evaluated for severity, and the cause (i.e., study drug or procedure) of each AE was determined. The analysis of AE included all 166 patients who underwent randomization.

The following considerations were taken into account when establishing clinical trial parameters and performing statistical analysis of the data obtained from the clinical trial. Sample size was determined using a one-sided testing framework with an alpha error of 0.1 and a beta error of 0.1, as the prospective primary hypothesis was that 14-day treatment with the highest doses of Mongersen would result in a higher proportion of patients in clinical remission than 14-day placebo treatment. An assumption was made that the group receiving the highest dose of Mongersen would have a rate of remission of 50% and that the placebo group would have a remission rate of 20%. It was estimated that 40 patients would be needed in each group in order to detect a significant difference in remission rates between each group at a power of 90%. All efficacy analyses were conducted according to the intention-to-treat principle on all randomized patients who received at least one dose of the assigned treatment. Patients with missing primary endpoint data at day 15 and/or day 28 were classified as failure. Remission and response rates were compared using the Pearson's chi-square test or Fisher's exact test. The proportions of patients with changes from baseline CRP levels between each of the three Mongersen groups and the placebo group were also described.

188 patients were screened for participation in the clinical trial and 166 were deemed eligible for enrollment (FIG. 1). Eligible patients were randomly assigned to receive Mongersen at a dose of either 10 mg/day (N=41), 40 mg/day (N=40) or 160 mg/day (N=43), or placebo (N=42). Demographic and clinical characteristics of the patients in each treatment group were evaluated and noted to be similar (Table 1).

TABLE 1

Baseline Demographic and Clinical Characteristics

| Characteristic | Placebo (N = 42) | Mongersen 10 mg (N = 41) | Mongersen 40 mg (N = 40) | Mongersen 160 mg (N = 43) |
| --- | --- | --- | --- | --- |
| Age - yr | | | | |
| mean | 41 | 43 | 43 | 43 |
| range | 19-74 | 20-71 | 19-69 | 22-70 |
| Sex - no. (%) | | | | |
| male | 23 (54.76) | 17 (41.46) | 21 (52.5) | 20 (46.51) |
| female | 19 (45.23) | 24 (58.53) | 19 (47.5) | 23 (53.48) |
| Body Mass Index | | | | |
| mean | 23.24 | 22.23 | 23.63 | 23.60 |
| range | 15.76-39.84 | 15.89-29.94 | 18.29-38.45 | 15.06-36.36 |

TABLE 1-continued

Baseline Demographic and Clinical Characteristics

| Characteristic | Placebo (N = 42) | Mongersen 10 mg (N = 41) | Mongersen 40 mg (N = 40) | Mongersen 160 mg (N = 43) |
|---|---|---|---|---|
| Crohn's Disease Activity Index score median (range) | 264 (222-392) | 246 (221-399) | 240 (223-368) | 243 (221-396) |
| CRP - mg/L median (range) | 5.1 (0-102) | 4.3 (0-78) | 4.9 (0-47) | 4.6 (0-51) |
| Steroid-Dependent - no. (%) | 36 (85.7) | 32 (78.0) | 38 (95.0) | 36 (83.7) |
| Steroid-Resistant - no. (%) | 6 (14.3) | 9 (22.0) | 2 (5.0) | 7 (16.3) |
| Concomitant medication with immunomodulators - no. (%) | 12 (28.6) | 6 (14.6) | 7 (17.5) | 12 (27.9) |
| Smokers - no. (%) | 14 (33.3) | 18 (43.9) | 13 (32.5) | 17 (39.5) |
| Previous history of CDrelated intestinal resection: - no. (%) | 14 (33.3) | 21 (51.2) | 15 (37.5) | 19 (44.2) |
| Steroid use at baseline n (%) | 9 (21.4) | 7 (17.1) | 13 (32.5) | 9 (20.9) |
| Duration of CD: yr - mean (SEM) | 10.9 (1.44) | 12.3 (1.58) | 7 (1.3) | 9.3 (1.51) |

Of this group of 166 patients, 1 patient in the 160 mg/day Mongersen group, 1 patient in the 40 mg/day Mongersen group, 3 patients in the 10 mg/day Mongersen group, and 1 patient in the placebo group did not adhere to the drug administration protocol (FIG. 1). 160 patients out of 166 patients that entered the trial (96.38%) completed the 2-week treatment correctly, and 138 patients (83.1%; 39 patients in the 160 mg/day Mongersen group, 37 patients in the 40 mg/day Mongersen group, 32 patients in the 10 mg/day Mongersen group, and 30 patients in the placebo group) completed the entire protocol, including the 84-day follow-up period (FIG. 1). Some patients were withdrawn from the trial during the follow-up period due to AE, disease worsening, requests to be withdrawn by the patients, disappearance of the patient, or based on an investigator's decision.

No statistically significant differences in median steroid consumption were detected between the groups at baseline (Table 1). One patient receiving placebo and 1 receiving 10 mg/day Mongersen were taking 25 mg/day prednisone, and 1 patient receiving 40 mg/day Mongersen was taking 5 mg/day prednisone. Budesonide was taken by 8 patients receiving placebo (median dose 6 mg/day), six patients receiving 10 mg/day Mongersen (median dose 6 mg/day), 12 patients receiving 40 mg/day Mongersen (median dose 6 mg/day), and nine patients receiving 160 mg/day Mongersen (median dose 7.5 mg/day). At day 84, the percentage of patients who reached a steroid-free remission was significantly greater with 160 mg/day Mongersen (6/9, 67%) than with placebo (1/9, 11%, P=0.04), while there was no difference between 10 mg/day (3/7, 43%) or 40 mg/day (6/13, 46%) and placebo.

Example 2

Treatment with an Anti-SMAD7 Therapy Induces Remission in IBD Patients

Figure 2:
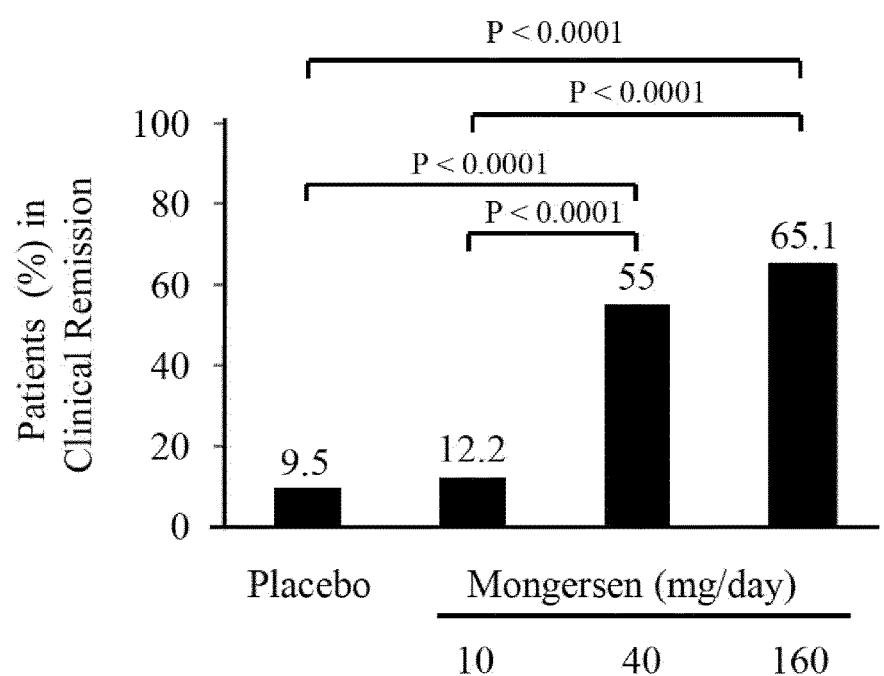
FIG. 2 is a bar graph showing the percent of clinical remission in patients after the two-week clinical trial drug treatment period. As indicated, 9.5% of patients in the placebo group, 12.2% of patients in the 10 mg/day Mongersen group, 55% of patients in the 40 mg/day Mongersen group, and 65.1% of patients in the 160 mg/day Mongersen group entered remission following the end of treatment. Numbers shown below the graph show the actual number of patients in each group with a CDAI score of greater than 150 and the number of patients in each group with a CDAI score of less than 150, at the time of evaluation. Remission rates in the 40 mg/day and 160 mg/day Mongersen groups were significantly greater than the remission rates in the placebo and 10 mg/day Mongersen groups ($P<0.0001$ for both the 40 mg/day and 160 mg/day Mongersen groups vs. either of the 10 mg/day or placebo groups).

In order to determine whether treatment with Mongersen resulted in remission in patients with CD, CDAI scores were evaluated after the two week treatment period ended. Patients with CDAI scores of less than 150 at both day 15 (1 day after stopping drug treatment) and day 28 (2 weeks after stopping drug treatment) were considered to have entered remission. In the placebo group, 4 out of 42 patients (9.5%) entered remission. By contrast, 22 out of 40 patients (55%) and 28 out of 43 patients (65.1%), respectively, in the 40 mg/day and 160 mg/day Mongersen groups entered remission. 5 out of 41 patients (12.2%) in the 10 mg/day Mongersen group entered remission (FIG. 2). The remission rates in the 160 mg/day and 40 mg/day Mongersen groups were significantly higher than those in the 10 mg/day Mongersen ($P<0.0001$ for both groups) and placebo groups ($P<0.0001$ for both groups). There was no significant difference in remission rates between the 160 mg/day and 40 mg/day Mongersen groups or between the 10 mg/day Mongersen and placebo groups. These results demonstrated that administration of an anti-SMAD7 antisense therapy was effective to induce clinical remission in IBD patients.

Figure 3A:
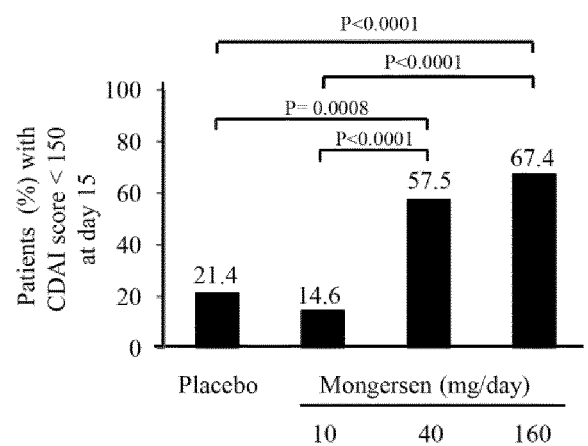
FIG. 3A is a bar graph showing the percentage of patients in each group with CDAI scores of less than 150 on day 15 of the trial. The percentage of patients with CDAI scores of less than 150 in the 160 mg/day, 40 mg/day, and 10 mg/day Mongersen groups and placebo groups were 67.4%, 57.5%, 14.6%, and 21.4%, respectively. On day 15, the percent of patients with CDAI scores lower than 150 was significantly higher in the 160 mg/day and 40 mg/day Mongersen groups compared to the 10 mg/day Mongersen group ($P<0.0001$ for both groups) and the placebo group ($P<0.0001$ and $P=0.0008$, respectively).

CDAI scores were also analyzed in each group at day 15, day 28, and day 84 of the trial in order to determine whether treatment with the anti-SMAD7 therapy resulted in maintenance of CDAI scores of less than 150 over a longer period of time. On day 15, the percentage of patients with CDAI scores of less than 150 in the 160 mg/day, 40 mg/day, and 10 mg/day Mongersen groups and placebo groups were 67.4%, 57.5%, 14.6%, and 21.4%, respectively (FIG. 3A). On day 15, the percent of patients with CDAI scores lower than 150 was significantly higher in the 160 mg/day and 40 mg/day Mongersen groups compared to the 10 mg/day Mongersen group ($P<0.0001$ for both groups) and the placebo group ($P<0.0001$ and $P=0.0008$, respectively).

Figure 3B:
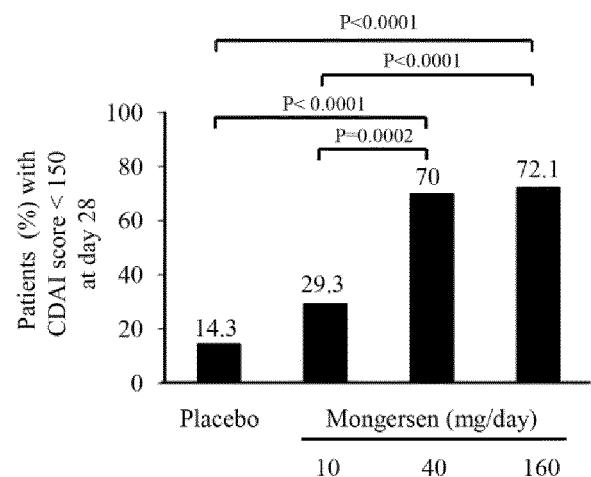
FIG. 3B is a bar graph showing the percentage of patients in each group with CDAI scores of less than 150 on day 28 of the trial. On day 28, the percentage of patients with CDAI scores of less than 150 in the 160 mg/day, 40 mg/day, and 10 mg/day Mongersen groups and placebo groups were 72.1%, 70%, 29.3%, and 14.3%, respectively. On day 28, the percent of patients with CDAI scores lower than 150 was significantly higher in the 160 mg/day and 40 mg/day Mongersen groups compared to the 10 mg/day Mongersen group ($P<0.0001$ and $P=0.0002$, respectively) and the placebo group ($P<0.0001$ for both groups).

On day 28, the percentage of patients with CDAI scores of less than 150 in the 160 mg/day, 40 mg/day, and 10 mg/day Mongersen groups and placebo groups were 72.1%, 70%, 29.3%, and 14.3%, respectively (FIG. 3B). On day 28, the percent of patients with CDAI scores lower than 150 was significantly higher in the 160 mg/day and 40 mg/day Mongersen groups compared to the 10 mg/day Mongersen group (P<0.0001 and P=0.0002, respectively) and the placebo group (P<0.0001 for both groups).

Figure 3C:
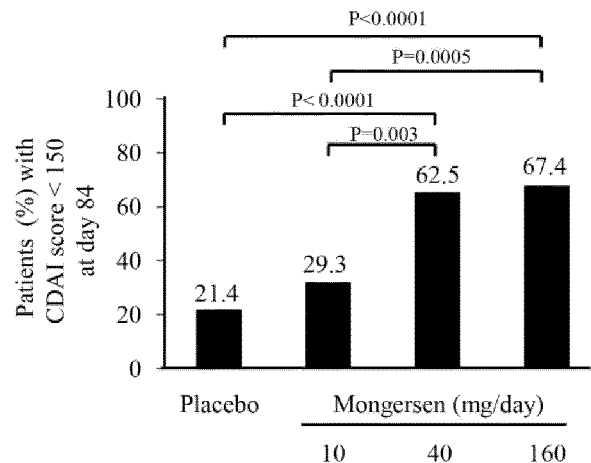
FIG. 3C is a bar graph showing the percentage of patients in each group with CDAI scores of less than 150 on day 84 of the trial. On day 84, the percentage of patients with CDAI scores of less than 150 in the 160 mg/day, 40 mg/day, and 10 mg/day Mongersen groups and placebo groups were 67.4%, 62.5%, 29.3%, and 21.4%, respectively. On day 84, the percent of patients with CDAI scores lower than 150 was significantly higher in the 160 mg/day and 40 mg/day Mongersen groups compared to the 10 mg/day Mongersen group ($P=0.0005$ and $P=0.003$, respectively) and the placebo group ($P<0.0001$ for both groups).

On day 84, the percentage of patients with CDAI scores of less than 150 in the 160 mg/day, 40 mg/day, and 10 mg/day Mongersen groups and placebo groups were 67.4%, 62.5%, 29.3%, and 21.4%, respectively (FIG. 3C). On day 84, the percent of patients with CDAI scores lower than 150 was significantly higher in the 160 mg/day and 40 mg/day Mongersen groups compared to the 10 mg/day Mongersen group (P=0.0005 and P=0.003, respectively) and the placebo group (P<0.0001 for both groups). These results demonstrated that treatment of IBD patients with an anti-SMAD7 therapy was effective to induce a CDAI score of less than 150 in patients at least 70 days following the end of drug treatment.

58.1% of patients receiving 160 mg/day Mongersen achieved remission at Day 15, which was maintained at both week 4 (28 days) and week 12 (84 days), compared to 9.5% of placebo patients (p<0001).

Table 2 provides the median values and value range for CDAI scores of patients in each treatment group at baseline, day 15, day 28, and day 84 of the trial. As indicated in Table 2, median changes in CDAI scores in the 40 mg/day and 160 mg/day Mongersen-treated groups were significantly greater compared with those in the placebo group at each time point. No statistical difference was observed between the 10 mg/day Mongersen and placebo groups at any time point.

TABLE 2

Crohn's Disease Activity Index (CDAI) Score at Baseline and Days 15, 28, and 84.

| CDAI score | Placebo | Mongersen 10 mg | Mongersen 40 mg | Mongersen 160 mg |
|---|---|---|---|---|
| Baseline | 264 (222-392) | 246 (221-399) | 240 (223-368) | 243 (222-392) |
| Day 15 | 217 (66-421) | 201 (95-484) | 147 (20-316)† | 142 (32-271)† |
| Day 28 | 235 (71-421) | 181 (67-484) | 137 (0-436)† | 137 (31-348)† |
| Day 84 | 222 (37-431) | 187 (49-484) | 124 (16-436)† | 121 (18-306)† |

Data indicate median values (range).
All P-values are for the change from baseline in each Mongersen group as compared with the placebo group.
†P < 0.001.

Example 3

Treatment with an Anti-SMAD7 Therapy Induces Steroid-Free Remission in IBD Patients The number of patients who achieved steroid-free clinical remission at the end of the trial was analyzed in order to determine if treatment with a SMAD7 antisense oligonucleotide therapy was able to facilitate steroid-free remission. At the beginning of the trial, 9 out of 42 (21.4%) of individuals in the placebo group, 7 out of 41 (17.1%) of individuals in the 10 mg/day Mongersen group, 13 out of 40 (32.5%) of individuals in the 40 mg/day Mongersen group, and 9 out of 43 (20.9%) of individuals in the 160 mg/day Mongersen group were actively taking steroids. No significant differences in median steroid consumption existed between the groups at the beginning of the trial. On day 84 of the trial, a significantly greater portion of those individuals in the 160 mg/day group taking steroids at the start of the trial had achieved steroid-free remission as compared to the same group of individuals in the placebo group (P=0.04; 160 mg/day, 6/9 individuals (67%) achieved steroid-free remission vs. placebo, 1/9 individuals achieved steroid-free remission). Steroid-free remission was defined as clinical remission (defined above) with the equivalent of 0 mg prednisone ingestion. No significant differences were observed between the placebo group and the other Mongersen groups. These results demonstrate that treatment with a SMAD7 antisense oligonucleotide resulted in steroid-free remission in a cohort of individuals with IBD ingesting steroids prior to SMAD7 antisense oligonucleotide treatment.

Example 4

Treatment with an Anti-SMAD7 Therapy Induces Clinical Response in IBD Patients

Figure 4A:
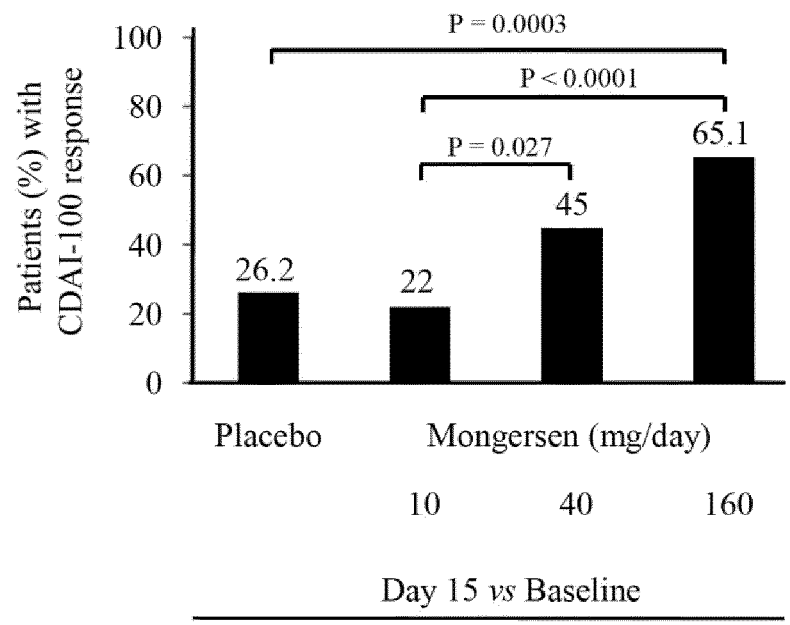
FIG. 4A is a bar graph showing the percent of patients in each treatment group with a 100-point CDAI score decrease at day 15 of the clinical trial compared to baseline. The graph shows that 65.1% of patients in the 160 mg/day Mongersen group, 45% of patients in the 40 mg/day Mongersen group, 22% of patients in the 10 mg/day Mongersen group, and 26.2% of patients in the placebo group experienced a 100-point CDAI decrease at day 15 compared to baseline. The percentage of patients who experienced a 100-point clinical response was significantly greater in the 160 mg/day and 40 mg/day Mongersen groups compared to the 10 mg/day Mongersen group ($P<0.0001$ and $P=0.027$ respectively). The percentage of patients who experienced a 100-point clinical response was also significantly greater in the 160 mg/day Mongersen group, compared to the placebo group (P=0.0003).

In order to determine whether treatment with an anti-SMAD7 therapy was effective to cause a clinical response in patients with CD, patient CDAI scores were evaluated after the two week treatment period ended (i.e., on day 15). Clinical response was defined as a 100-point decrease in CDAI score at day 15 compared to baseline (i.e., prior to drug treatment). A clinical response according to this criteria was documented in 65.1% of patients in the 160 mg/day Mongersen group, 45% of patients in the 40 mg/day Mongersen group, 22% of patients in the 10 mg/day Mongersen group, and 26.2% of patients in the placebo group (FIG. 4A). The percentage of patients who experienced a 100-point CDAI decrease was significantly greater in the 160 mg/day and 40 mg/day Mongersen groups compared to the 10 mg/day Mongersen group (P<0.0001 and P=0.027 respectively). The percentage of patients who experienced a 100-point clinical response was also significantly greater in the 160 mg/day Mongersen group, compared to the placebo group (P=0.0003).

Figure 4B:
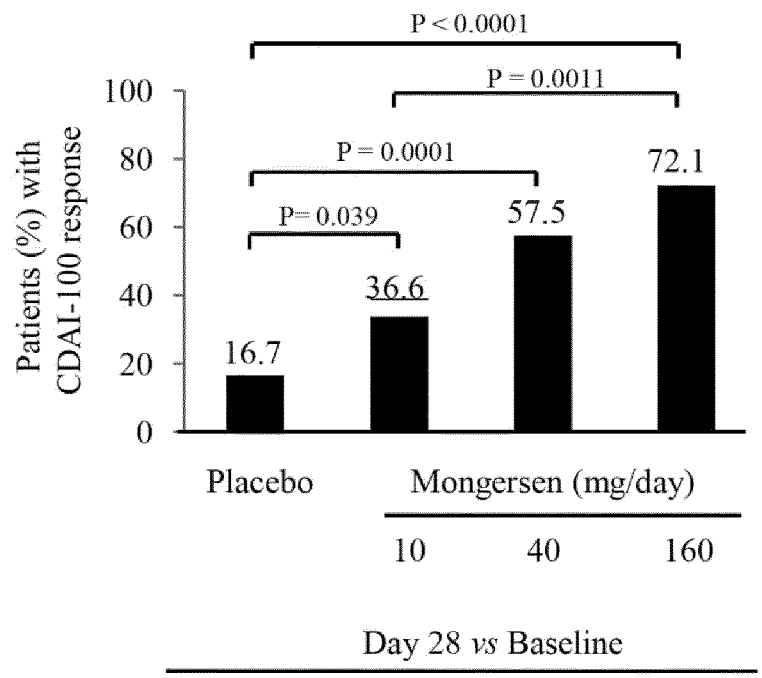
FIG. 4B is a bar graph showing the percent of patients in each treatment group with a 100-point CDAI score decrease at day 28 of the clinical trial compared to baseline. The graph shows that a clinical response according to this criteria was observed in 72.1% of patients in the 160 mg/day Mongersen group, 57.5% of patients in the 40 mg/day Mongersen group, 36.6% of patients in the 10 mg/day Mongersen group, and 16.7% of patients in the placebo group. The percentage of patients who experienced a 100-point CDAI decrease on day 28 was significantly greater in the 160 mg/day, 40 mg/day, and 10 mg/day Mongersen groups compared to the placebo group (FIG. 4B; P<0.0001 for the 160 mg/day group, P=0.0001 for the 40 mg/day group, and P=0.039 for the 10 mg/day group, compared to placebo for each group, respectively).

Additionally, patient CDAI scores were evaluated on day 28 of the clinical trial (2 weeks after the end of treatment). Clinical response was defined in this case as a 100-point decrease in CDAI score at day 28 compared to baseline (i.e., prior to drug treatment). A clinical response according to this criteria was documented in 72.1% of patients in the 160 mg/day Mongersen group, 57.5% of patients in the 40 mg/day Mongersen group, 36.6% of patients in the 10 mg/day Mongersen group, and 16.7% of patients in the placebo group (FIG. 4B). The percentage of patients who experienced a 100-point CDAI decrease was significantly greater in the 160 mg/day, 40 mg/day, and 10 mg/day Mongersen groups compared to the placebo group (FIG. 4B; P<0.0001 for the 160 mg/day group, P=0.0001 for the 40 mg/day group, and P=0.039 for the 10 mg/day group, compared to placebo for each group, respectively). These results demonstrated that both immediately after (i.e., day 15) and two weeks after (i.e., day 28) stopping drug treatment, treatment with an anti-SMAD7 therapy induced significant rates of clinical remission, defined as a CDAI decrease of at least 100 points compared to baseline, in IBD patients.

Figure 4C:
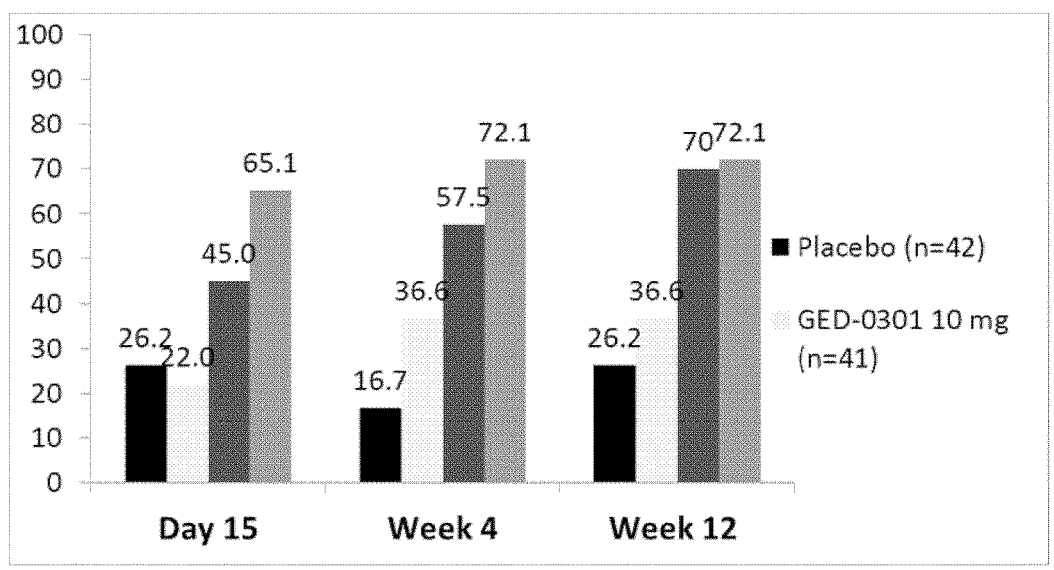
FIG. 4C is a bar graph showing the data from FIGS. 4A and 4B along with 12 week (day 84) data for a 100-point CDAI score decrease. The first bar for each time point indicates Placebo patient group; the second bar for each time point indicates 10 mg/day patient group; the third bar for each time point indicates 40 mg/day patient group; and the fourth bar for each time point indicates 160 mg/day patient group.

Similarly, patient CDAI scores were evaluated on day 84 of the clinical trial (10 weeks after the end of treatment). Clinical response was defined in this case as a 100-point decrease in CDAI score at day 84 compared to baseline (i.e., prior to drug treatment). A clinical response according to this criteria was documented in 72.1% of patients in the 160 mg/day Mongersen group, 70.0% of patients in the 40 mg/day Mongersen group, 36.6% of patients in the 10 mg/day Mongersen group, and 26.2% of patients in the placebo group (FIG. 4C). The percentage of patients who experienced a 100-point CDAI decrease was significantly greater in the 160 mg/day and 40 mg/day Mongersen groups as compared to the placebo group. These results demonstrated that both immediately after (e.g., day 15) and two weeks after (e.g., day 28) stopping drug treatment, treatment with an anti-SMAD7 therapy induced significant rates of clinical remission, defined as a CDAI decrease of at least 100 points compared to baseline, in IBD patients. These results demonstrated that both immediately after (e.g., day 15) and two and ten weeks after (e.g., day 28 and day 84) stopping drug treatment, treatment with an anti-SMAD7 therapy induced significant rates of clinical remission, defined as a CDAI decrease of at least 100 points compared to baseline, in IBD patients.

Figure 5A:
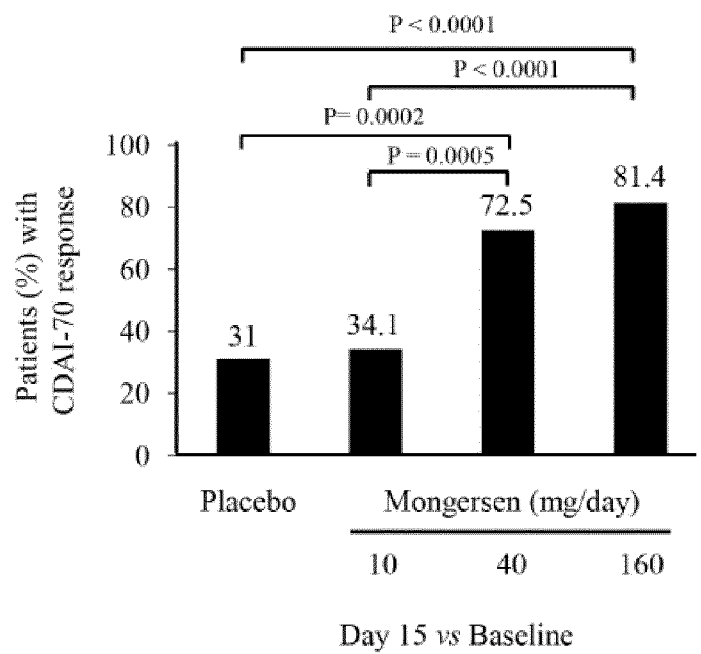
FIG. 5A is a bar graph showing the percent of patients in each treatment group with a 70-point CDAI score decrease at day 15 of the clinical trial compared to baseline. The graph shows that a 70-point CDAI decrease was documented in 81.4% of patients in the 160 mg/day Mongersen group, 72.5% of patients in the 40 mg/day Mongersen group, 34.1% of patients in the 10 mg/day Mongersen group, and 31% of patients in the placebo group. The percentage of patients who experienced a 70-point CDAI score decrease on day 15 was significantly greater in the 160 mg/day and 40 mg/day Mongersen groups compared to the 10 mg/day Mongersen (P<0.0001 and P=0.0005, respectively) and placebo groups (P<0.0001 and P=0.0002, respectively).
Figure 5B:
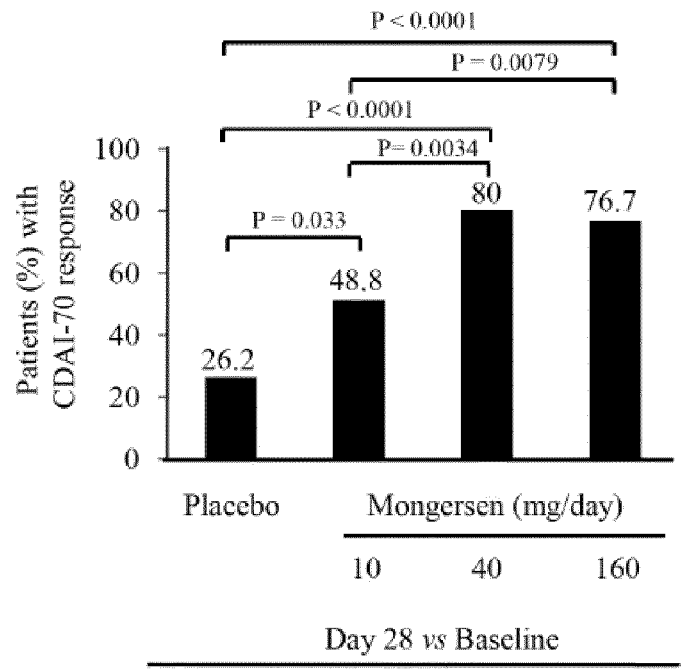
FIG. 5B is a bar graph showing the percent of patients in each treatment group with a 70-point CDAI score decrease at day 28 of the clinical trial compared to baseline. The graph shows that a 70-point CDAI decrease was documented in 76.7% of patients in the 160 mg/day Mongersen group, 80% of patients in the 40 mg/day Mongersen group, 48.8% of patients in the 10 mg/day Mongersen group, and 26.2% of patients in the placebo group. The percentage of patients who experienced a 70-point CDAI score decrease on day 28 was significantly greater in the 160 mg/day, 40 mg/day, and 10 mg/day Mongersen groups compared to placebo groups (P<0.0001, P<0.0001, and P=0.033, respectively).

Clinical response defined as a decrease in CDAI score in patients of 70 points compared to baseline was also evaluated on days 15 and 28 of the clinical trial. On day 15 a 70-point CDAI decrease was documented in 81.4% of patients in the 160 mg/day Mongersen group, 72.5% of patients in the 40 mg/day Mongersen group, 34.1% of patients in the 10 mg/day Mongersen group, and 31% of patients in the placebo group (FIG. 5A). The percentage of patients who experienced a 70-point CDAI score decrease on day 15 was significantly greater in the 160 mg/day and 40 mg/day Mongersen groups compared to the 10 mg/day Mongersen (P<0.0001 and P=0.0005, respectively) and placebo groups (P<0.0001 and P=0.0002, respectively). On day 28, a 70-point CDAI decrease was documented in 76.7% of patients in the 160 mg/day Mongersen group, 80% of patients in the 40 mg/day Mongersen group, 48.8% of patients in the 10 mg/day Mongersen group, and 26.2% of patients in the placebo group (FIG. 5B). The percentage of patients who experienced a 70-point CDAI score decrease on day 28 was significantly greater in the 160 mg/day, 40 mg/day, and 10 mg/day Mongersen groups compared to placebo groups (P<0.0001, P<0.0001, and P=0.033, respectively). These results demonstrated that both immediately after (i.e., at day 15) and two weeks after (i.e., day 28) stopping drug treatment, treatment with an anti-SMAD7 therapy induced significant rates of clinical remission, defined as a CDAI decrease of at least 70 points compared to baseline, in IBD patients.

Example 5

Figure 6A:
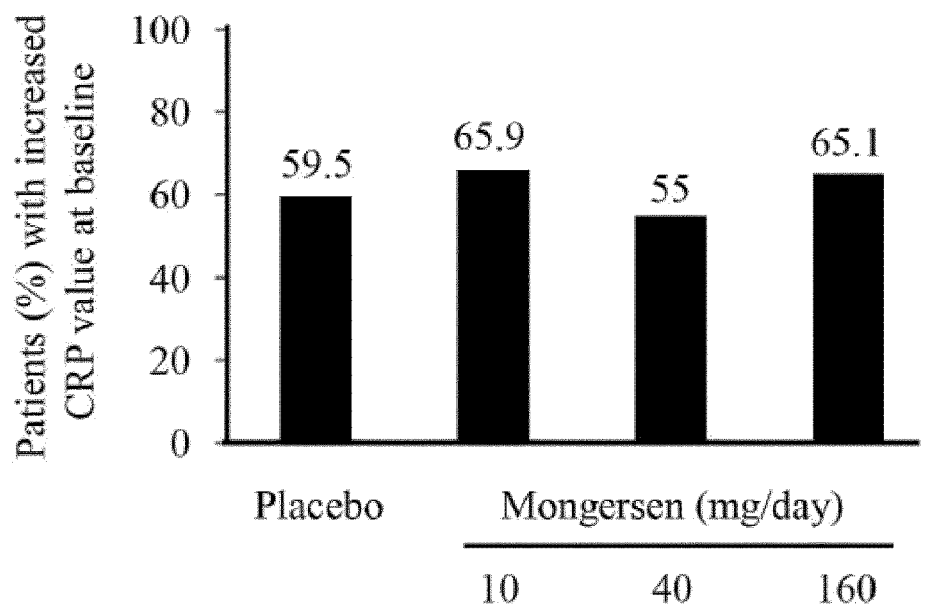
FIG. 6A is a bar graph that shows the percent of patients in each group with elevated CRP levels at baseline. Elevated CRP levels were observed in 59.5% of patients in the placebo group, 65.9% of patients in the 10 mg/day Mongersen group, 55% of patients in the 40 mg/day Mongersen group, and 65.1% of patients in the 160 mg/day Mongersen group.
Figure 6B:
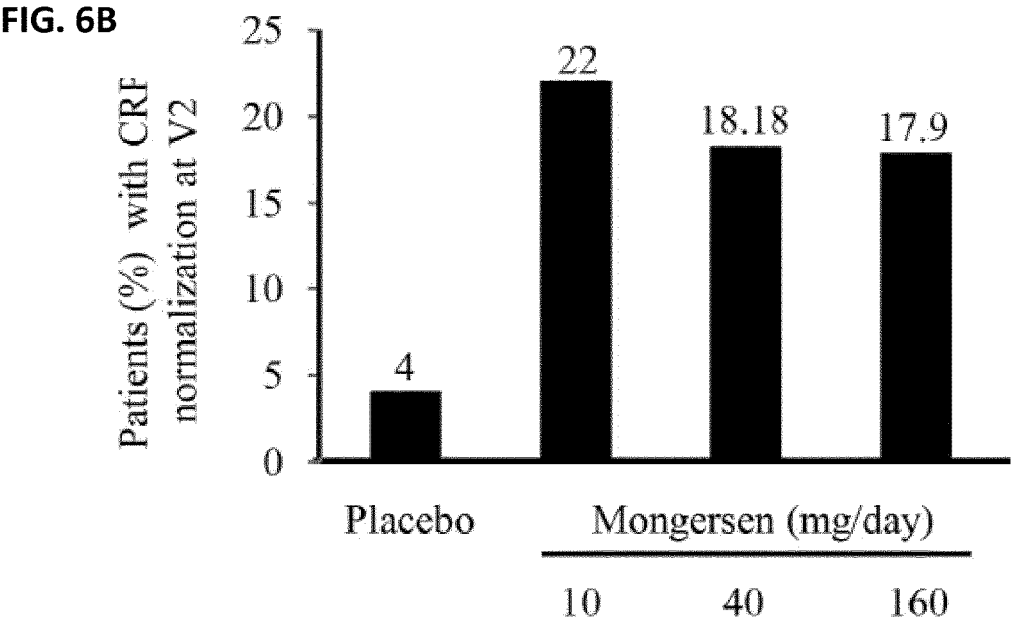
FIG. 6B is a bar graph that shows the percent of patients in each group with normalized CRP levels on day 15 of the clinical trial. Normalized CRP levels were observed in 4% of patients in the placebo group, and 22%, 18.18%, and 17.9% of patients, respectively, in the 10 mg/day, 40 mg/day and 160 mg/day Mongersen groups.
Figure 7:
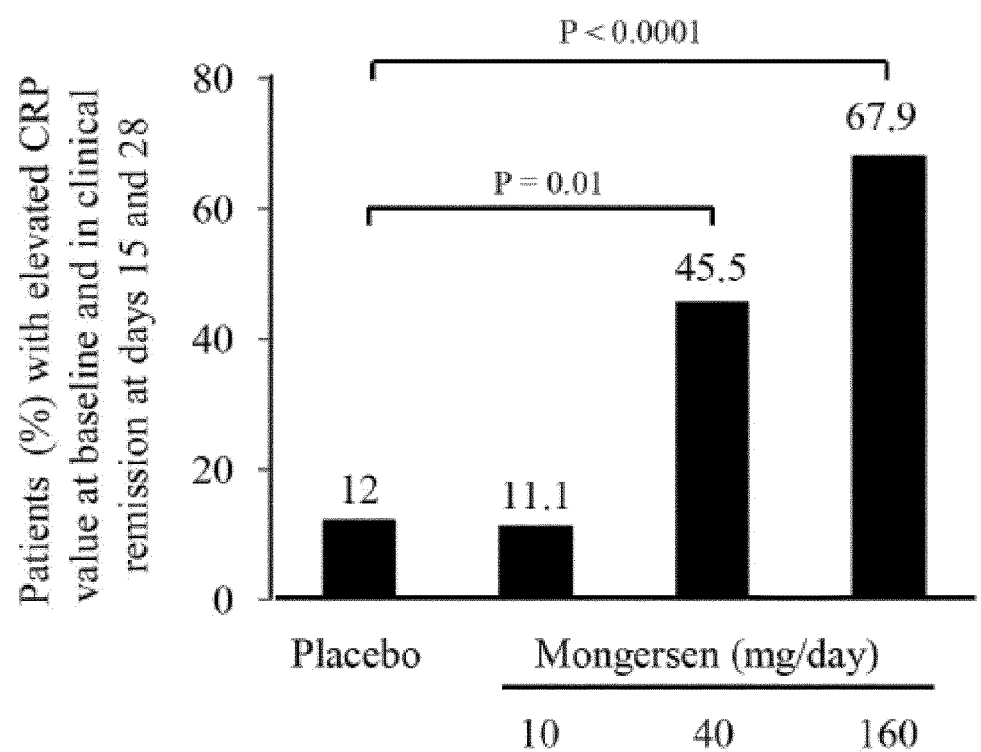
FIG. 7 is a bar graph showing the percent of patients in each treatment group with elevated baseline CRP levels at baseline that entered remission. In patients with elevated CRP levels at baseline, the percentage of patients that entered remission were 67.9%, 45.5%, 11.1%, and 12%, respectively, in the 160 mg/day, 40 mg/day, and 10 mg/day Mongersen groups and the placebo group. The percentage of patients with elevated CRP levels at baseline that entered remission was significantly higher in the 160 mg/day and 40 mg/day Mongersen groups compared to the placebo group (P<0.0001 and P=0.01, respectively). No significant difference was observed between the 160 mg/day and 40 mg/day Mongersen groups or between the 10 mg/day Mongersen and placebo groups.

Treatment with an Anti-SMAD7 Therapy Results in Decreased CRP Levels in IBD Patients Levels of CRP were evaluated in patients enrolled in the trial both prior to beginning the anti-SMAD7 therapy treatment and after treatment (i.e., day 15) in order to determine if the anti-SMAD7 therapy was able to induce a change in circulating CRP levels. Screening of patients prior to beginning Mongersen treatment demonstrated that 102 out of 166 patients (61.4%) had elevated CRP levels (i.e., greater than 3.0 mg/liter). Specifically, elevated CRP levels were observed in 25 out of 42 patients (59.5%) in the placebo group, 27 out of 41 patients (65.9%) in the 10 mg/day Mongersen group, 22 out of 40 patients (55%) in the 40 mg/day Mongersen group, and 28 out of 43 patients (65.1%) in the 160 mg/day Mongersen group (FIG. 6A). Evaluation of patients on day 15 demonstrated that the percentage of patients with normalized levels of CRP (i.e., <3 mg/liter) was 4% in the placebo group, and 22%, 18.18%, and 17.9%, respectively, in the 10 mg/day, 40 mg/day and 160 mg/day Mongersen groups (FIG. 6B). Table 3 shows the median CRP levels and the range of CRP levels in patients with elevated CRP levels (>3 mg/L) at baseline in each treatment group. Among patients with elevated CRP levels at baseline, neither placebo nor Mongersen treatment significantly reduced the median values of CRP at days 15, 28, or 84 compared to baseline.

TABLE 3

CRP Levels at Baseline and Days 15, 28, and 84 in Placebo and Mongersen-treated Patients with Elevated CRP Levels at Baseline

| C-reactive protein (mg/L) | Placebo (n = 25) | Mongersen 10 mg (n = 27) | Mongersen 40 mg (n = 22) | Mongersen 160 mg (n = 28) |
|---|---|---|---|---|
| Baseline | 10.6 (3.7-102) | 5.9 (3.02-78) | 8.02 (4.5-47.2) | 11.1 (3.17-51) |
| Day 15 | 20.6 (1.1-92.2) | 6.9 (0.4-104) | 6.2 (1.0-26.2) | 9.1 (1.4-52.3) |
| Day 28 | 17 (1.7-160.5) | 6.9 (1.0-101) | 5.6 (1.6-39.7) | 11.3 (0.9-65.1) |
| Day 84 | 8.5 (1.0-127.7) | 5.1 (1.4-44.6) | 4.8 (1.8-39) | 8.1 (1.5-54.3) |

Data indicate median values (range).

These results indicate that treatment of IBD patients with an anti-SMAD7 therapy, even at low concentrations, resulted in an increase in the percentage of patients with normalized CRP levels compared to a placebo treatment.

Additionally, elevated baseline CRP levels and remission data from individual patients were analyzed to determine whether treatment with the anti-SMAD7 therapy resulted in remission in patients with initially elevated CRP levels (i.e., greater than 3.0 mg/liter). At day 15, the proportion of remitters (as defined by CDAI scores <150 and normalized CRP) among patients with elevated baseline CRP was 1/6 (16.7%), 0/4 (0%), 2/11 (18.2%), and 5/20 (25%) in the placebo, 10 mg/day, 40mg/day, and 160mg/day Mongersen groups, respectively. The analysis also showed that in patients with elevated CRP levels at baseline, the rates of remission at days 15 and 28 in the 160 mg/day and 40 mg/day Mongersen groups (67.9% and 45.5%, respectively) were significantly higher than the rates of remission for the same category of patients in the placebo group (12%; P<0.0001 and P=0.01, respectively; FIG. 6). No significant difference was observed between the 160 mg/day and 40 mg/day Mongersen groups or between the 10 mg/day Mongersen group (11.1%) and placebo group. This result demonstrated that anti-SMAD7 treatment of IBD patients with elevated CRP levels resulted in a significant increase in remission compared to treatment with placebo. This result further demonstrated that elevated CRP levels are a useful criterion for determining whether a patient will respond or is likely to respond to treatment with an anti-SMAD7 therapy.

Example 6

Treatment with an Anti-SMAD7 Therapy Reduces IL8 and TNFα Plasma Biomarker Expression In order to determine if SMAD7 antisense oligonucleotide treatment resulted in changes in other biomarkers associated with IBD, levels of IL8 and TNFα in patients were assessed at baseline, day 15, and day 28 of the trial by ELISA. As shown in Table 4, plasma concentrations of IL8 and TNFα were significantly reduced at days 15 and 28 compared to baseline in the 40 mg/day and 160 mg/day Mongersen groups (P<0.05 at days 15 and 28 compared to baseline in the 40 mg/day and 160 mg/day Mongersen groups). No significant difference was observed in the placebo or 10 mg/day Mongersen groups. These results demonstrate that treatment of patients with IBD with a SMAD7 antisense oligonucleotide for two weeks or less resulted in significantly reduced levels of IL8 and TNFα.

TABLE 4

Cytokine Levels in Plasma Samples of Patients with Crohn's Disease Before and After Treatment with 10 mg/day, 40 mg/day and 160 mg/day Mongersen.

|  | Mongersen 10 | Mongersen 40 | Mongersen 160 |
|---|---|---|---|
| IL8 (pg/mL) | | | |
| Baseline | 28 (5.6) | 27 (7.2) | 30.6 (6.4) |
| Day 15 | 24 (9.2) | 17 (2.5)† | 17.9 (5.1)† |
| Day 28 | 23 (7.3) | 16 (3.2)† | 16.8 (5.6)† |
| TNF (pg/mL) | | | |
| Baseline | 15.4 (8) | 19.2 (7.3) | 22.4 (8.6) |
| Day 15 | 16 (5.4) | 11.4 (3.2)† | 14.2 (4.1)† |
| Day 28 | 14 (6.6) | 12.8 (2.6)† | 11.9 (3.3)† |

Data indicate mean (SD).
†P < 0.05 versus baseline.

Example 7

Treatment with an Anti-SMAD7 Therapy is Tolerated in Patients with IBD

In order to determine whether treatment with Mongersen was associated with safety issues or AEs, instances of such issues and events were tracked throughout the trial. Nine serious adverse events (SAE) were registered in 6 patients. 2 SAE were documented in 1 patient in the placebo group, 4 SAE were documented in 3 patients in the 10 mg/day Mongersen group, 2 SAE were documented in 1 patient in the 40 mg/day Mongersen group, and 1 SAE was documented in 1 patient in the 160 mg/day Mongersen group (Table 5). Two SAE were not considered by physicians to be related to treatment. Most SAE consisted of hospital admissions for complications or symptoms associated with CD. One patient in the group given 160 mg of Mongersen experienced a thermal burn of his legs while cooking. No patients died during the clinical trial.

TABLE 5

Serious adverse events registered during the study.

|  | Placebo (n = 42) | Mongersen 10 mg (n = 41) | Mongersen 40 mg (n = 40) | Mongersen 160 mg (n = 43) |
|---|---|---|---|---|
| Total pts with at least one SAE | 1 (2.4) | 3 (7.3) | 1 (2.5) | 1 (2.3) |
| Total number of SAEs | 2 | 4 | 2 | 1 |
| Abdominal pain | — | 2 (4.9) | — | — |
| Seton placement for perianal fistula | — | — | 1 (2.5) | — |
| Crohn's disease worsening | — | 1 (2.4) | — | — |
| Surgery for hemorrhoid thrombosis | — | — | 1 (2.5) | — |
| Pyrexia | 1 (2.4) | 1 (2.4) | — | — |
| Thermal burn | — | — | — | 1 (2.3) |
| Cough | 1 (2.4) | — | — | — |

Data indicate number (%) of patients (pts) with at least one serious adverse event (SAE) and total number of SAEs.
Differences between groups were not statistically significant.

28 patients in the placebo group and 20, 25, and 21 patients, respectively, in the 10 mg/day, 40 mg/day and 160 mg/day Mongersen groups experienced an AE during or after treatment (Table 6). Overall, 200 AE were documented during the clinical trial. These included 64 AE in the placebo group, 39 AE in the 10 mg/day Mongersen group, 50 in the 40 mg/day Mongersen group, and 47 in the 160 mg/day Mongersen group. The majority of AE were mild and considered not related to treatment by the investigators. No change in vital signs was noted in any patient during the study. No increase in serum complement factors was observed in patients during the trial. These results demonstrate that, overall, treatment of IBD with the anti-SMAD7 therapy is not associated with AE and is well-tolerated by patients.

TABLE 6

Adverse Events Reported by >5% of Patients in a Single Arm.

|  | Placebo (n = 42) | Mongersen 10 mg (n = 41) | Mongersen 40 mg (n = 40) | Mongersen 160 mg (n = 43) |
|---|---|---|---|---|
| Total pts with at least one AE (%) | 28 (66.7) | 20 (48.8) | 25 (62.5) | 21 (48.8) |
| Total number of AEs | 64 | 39 | 50 | 47 |
| Abdominal pain | 6 (14.28) | 4 (9.8) | 4 (10.0) | 5 (11.6) |
| Crohn's disease worsening | 14 (33.3) | 6 (14.6) | 4 (10.0) | 5 (11.6) |
| C-reactive protein increased | 4 (9.5) | 2 (4.9) | 2 (5.0) | 4 (9.3) |
| Pyrexia | 4 (9.5) | 3 (7.3) | 2 (5.0) | 2 (4.7) |
| Abdominal mass | 2 (4.8) | 1 (2.4) | 3 (7.5) | 3 (7.0) |
| Diarrhoea | 1 (2.4) | — | 2 (5.0) | 3 (7.0) |
| Arthralgia | 1 (2.4) | 2 (4.9) | 2 (5.0) | 1 (2.3) |
| Urinary tract infection | 1 (2.4) | 6 (14.6) | 2 (5.0) | 2 (4.7) |
| Asthenia | 1 (2.4) | — | 2 (5.0) | 1 (2.3) |
| Flu-like illness | 3 (7.1) | — | 1 (2.5) | 3 (6.97) |
| Headache | 3 (7.1) | — | — | 1 (2.3) |
| Transaminases increased | — | — | 2 (5.0) | — |

Data indicate number (%) of patients with at least one adverse event (AE) and total number of AEs.

Example 8

Clinical Remission Correlated with Baseline CRP Levels

Figure 8:
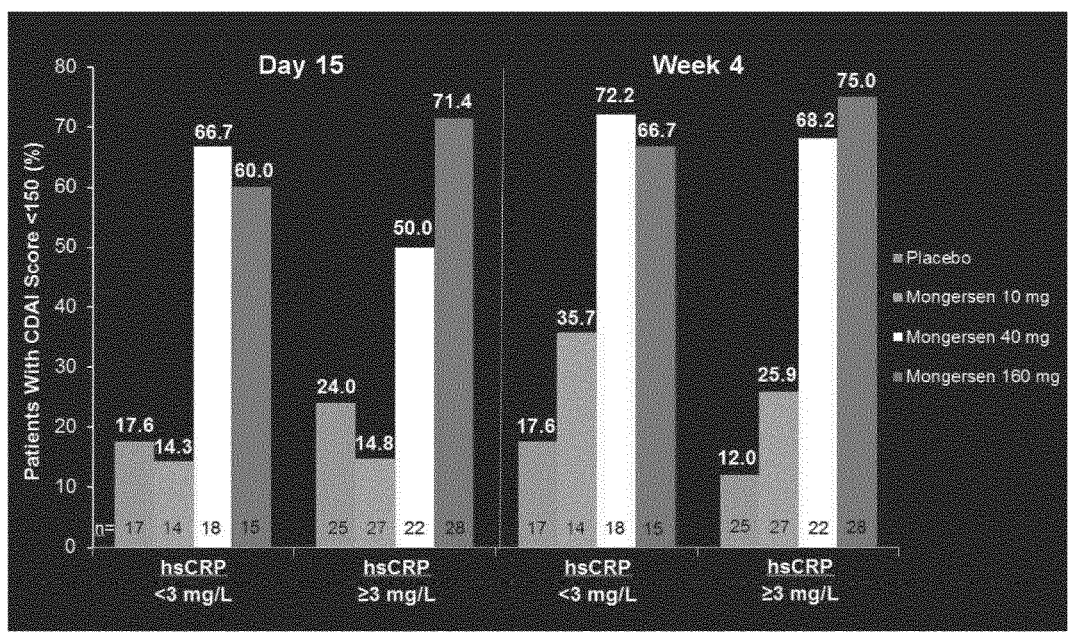
FIG. 8 is a bar graph showing percentage of patients with clinical remission for patients having CRP levels of less than 3 mg/l or having CRP levels of 3 mg/l or more at day 15 and week 4 of the trial.

The relationship between baseline CRP levels and clinical remission at day 15 and week 4 was studied, as shown in FIG. 8. Patients with CRP levels lower than 3 mg/L showed increased rates of remission after 15 days when receiving 40 mg/day or 160 mg/day Mongersen (66.7% and 60.0%, respectively), as compared to those receiving placebo or 10 mg/day Mongersen (17.6% and 14.3%, respectively). The rates of remission for patients with CRP levels of 3 mg/L or greater who received 40 mg/day or 160 mg/day Mongersen (50.0% and 71.4%, respectively) were greater than those receiving placebo or 10 mg/day Mongersen (24.0% and 14.8%, respectively).

After four weeks, patients with CRP levels lower than 3 mg/L and receiving placebo or 10, 40, or 160 mg/day Mongersen showed remission rates of 17.6%, 35.7%, 72.2%, and 66.7%, respectively. Patients with CRP levels of 3 mg/L or greater and receiving placebo or 10, 40, or 160 mg/day Mongersen showed remission rates of 12.0%, 25.9%, 68.2%, and 75.0%, respectively.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

| SEQUENCE |
|---|
| SEQ ID NO: 2 (Coding Sequence CDS (288-1568) of NM_005904.3; Homo sapiens SMAD family member 7 (SMAD7), transcript variant 1, mRNA) |
| 1    cggagagccg cgcagggcgc gggccgcgcg gggtggggca gccggagcgc aggcccccga |
| 61   tccccggcgg gcgccccgg gccccgcgc gcgccccggc ctccgggaga ctggcgcatg |
| 121  ccacggagcg cccctcgggc cgccgccgct cctgcccggg ccccctgctgc tgctgctgtc |
| 181  gcctgcgcct gctgccccaa ctcggcgccc gacttcttca tggtgtgcgg aggtcatgtt |
| 241  cgctccttag caggcaaacg acttttctcc tcgcctcctc gccccgcatg ttcaggacca |
| 301  aacgatctgc gctcgtccgg cgtctctgga ggagccgtgc gcccggcggc gaggacgagg |
| 361  aggagggcgc aggggggaggt ggaggaggag gcgagctgcg gggagaaggg gcgacggaca |
| 421  gccgagcgca tggggccggt ggcggcggcc cgggcagggc tggatgctgc ctgggcaagg |
| 481  cggtgcgagg tgccaaaggt caccaccatc cccacccgcc agccgcgggc gccggcgcgg |
| 541  ccgggggcgc cgaggcggat ctgaaggcgc tcacgcactc ggtgctcaag aaactgaagg |
| 601  agcggcagct ggagctgctg ctccaggccg tggagtcccg cggcgggacg cgcaccgcgt |
| 661  gcctcctgct gcccggccgc ctggactgca ggctgggccc gggggcgccc gccggcgcgc |
| 721  agcctgcgca gccgccctcg tcctactcgc tcccctcct gctgtgcaaa gtgttcaggt |
| 781  ggccggatct caggcattcc tcggaagtca agaggctgtg ttgctgtgaa tcttacggga |
| 841  agatcaaccc cgagctggtg tgctgcaacc cccatcacct tagccgactc tgcgaactag |
| 901  agtctccccc ccctccttac tccagatacc cgatggattt tctcaaacca actgcagact |
| 961  gtccagatgc tgtgccttcc tccgctgaaa caggggggaac gaattatctg gcccctgggg |
| 1021 ggctttcaga ttcccaactt cttctggagc ctggggatcg gtcacactgg tgcgtggtgg |
| 1081 catactggga ggagaagacg agagtgggga ggctctactg tgtccaggag ccctctctgg |
| 1141 atatcttcta tgatctacct caggggaatg gcttttgcct cggacagctc aattcggaca |
| 1201 acaagagtca gctggtgcag aaggtgcgga gcaaaatcgg ctgcggcatc cagctgacgc |
| 1261 gggaggtgga tggtgtgtgg gtgtacaacc gcagcagtta ccccatcttc atcaagtccg |
| 1321 ccacactgga caacccggac tccaggacgc tgttggtaca caaggtgttc cccggtttct |
| 1381 ccatcaaggc tttcgactac gagaaggcgt acagcctgca gcggcccaat gaccacgagt |
| 1441 ttatgcagca gccgtggacg ggctttaccg tgcagatcag ctttgtgaag ggctggggcc |
| 1501 agtgctacac ccgccagttc atcagcagct gcccgtgctg gctagaggtc atcttcaaca |
| 1561 gccggtagcc gcgtgcggag gggacagagc gtgagctgag caggccacac ttcaaactac |
| 1621 tttgctgcta atattttcct cctgagtgct tgcttttcat gcaaactctt tggtcgtttt |
| 1681 ttttttgttt gttggttggt tttcttcttc tcgtcctcgt ttgtgttctg ttttgtttcg |
| 1741 ctctttgaga aatagcttat gaaaagaatt gttgggggtt tttttggaag aaggggcagg |
| 1801 tatgatcggc aggacaccct gataggaaga ggggaagcag aaatccaagc accaccaaac |

-continued

| | SEQUENCE | | | | |
|---|---|---|---|---|---|
| 1861 | acagtgtatg | aagggggcg | gtcatcattt | cacttgtcag | gagtgtgtgt gagtgtgagt |
| 1921 | gtgcggctgt | gtgtgcacgc | gtgtgcagga | gcggcagatg | gggagacaac gtgctctttg |
| 1981 | ttttgtgtct | cttatggatg | tccccagcag | agaggtttgc | agtcccaagc ggtgtctctc |
| 2041 | ctgccccttg | gacacgctca | gtggggcaga | ggcagtacct | gggcaagctg gcggctgggg |
| 2101 | tcccagcagc | tgccaggagc | acggctctgt | ccccagcctg | gaaagcccc tgccctcct |
| 2161 | ctccctcatc | aaggacacgg | gcctgtccac | aggcttctga | gcagcgagcc tgctagtggc |
| 2221 | cgaaccagaa | ccaattattt | tcatccttgt | cttattccct | tcctgccagc cctgccatt |
| 2281 | gtagcgtctt | tcttttttgg | ccatctgctc | ctggatctcc | ctgagatggg cttcccaagg |
| 2341 | gctgccgggg | cagcccctc | acagtattgc | tcacccagtg | ccctctcccc tcagcctctc |
| 2401 | ccctgcctgc | cctggtgaca | tcaggttttt | cccggactta | gaaaaccagc tcagcactgc |
| 2461 | ctgctcccat | cctgtgtgtt | aagctctgct | attaggccag | caagcgggga tgtccctggg |
| 2521 | agggacatgc | ttagcagtcc | ccttccctcc | aagaaggatt | tggtccgtca taacccaagg |
| 2581 | taccatccta | ggctgacacc | taactcttct | ttcatttctt | ctacaactca tacactcgta |
| 2641 | tgatacttcg | acactgttct | tagctcaatg | agcatgttta | gactttaaca taagctattt |
| 2701 | ttctaactac | aaaggtttaa | atgaacaaga | gaagcattct | cattggaaat ttagcattgt |
| 2761 | agtgctttga | gagagaaagg | actcctgaaa | aaaaacctga | gatttattaa agaaaaaaat |
| 2821 | gtattttatg | ttatatataa | atatattatt | acttgtaaat | ataaagacgt tttataagca |
| 2881 | tcattattta | tgtattgtgc | aatgtgtata | aacaagaaaa | ataaagaaaa gatgcacttt |
| 2941 | gctttaatat | aaatgcaaat | aacaaatgcc | aaattaaaaa | agataaacac aagattggtg |
| 3001 | ttttttttcta | tgggtgttat | tacctagctg | aatgttttc | taaaggagtt tatgttccat |
| 3061 | taaacgattt | ttaaaatgta | cacttgaa | | |

SEQ ID NO: 8 (CRP C-reactive protein, pentraxin-related [*Homo sapiens* (human)]
| 1 | aggcaggagg | aggtagctct | aaggcaagag | atctaggact | tctagcccct gaactttcag |
|---|---|---|---|---|---|
| 61 | ccgaatacat | cttttccaaa | ggagtgaatt | caggcccttg | tatcactggc agcaggacgt |
| 121 | gaccatggag | aagctgttgt | gtttcttggt | cttgaccagc | ctctctcatg cttttggcca |
| 181 | gacaggtaag | ggccaccca | ggctatggga | gagatttgat | ctgaggtatg ggggtggggt |
| 241 | ctaagactgc | atgaacagtc | tcaaaaaaaa | aaaaaaaga | ctgtatgaac agaacagtgg |
| 301 | agcatccttc | atggtgtgtg | tgtgtgtgtg | tgtgtgtgtg | tgtgtgtgtg tggtgtgtaa |
| 361 | ctggagaagg | ggtcagtctg | tttctcaatc | ttaaattcta | tacgtaagtg aggggataga |
| 421 | tctgtgtgat | ctgagaaacc | tctcacattt | gcttgttttt | ctggctcaca gacatgtcga |
| 481 | ggaaggcttt | tgtgtttccc | aaagagtcgg | atacttccta | tgtatccctc aaagcaccgt |
| 541 | taacgaagcc | tctcaaagcc | ttcactgtgt | gcctccactt | ctacacggaa ctgtcctcga |
| 601 | cccgtgggta | cagtattttc | tcgtatgcca | ccaagagaca | agacaatgag attctcatat |
| 661 | tttggtctaa | ggatatagga | tacagttta | cagtgggtgg | gtctgaaata ttattcgagg |
| 721 | ttcctgaagt | cacagtagct | ccagtacaca | tttgtacaag | ctgggagtcc gcctcaggga |
| 781 | tcgtggagtt | ctgggtagat | gggaagccca | gggtgaggaa | gagtctgaag aagggataca |
| 841 | ctgtggggc | agaagcaagc | atcatcttgg | ggcaggagca | ggattccttc ggtgggaact |
| 901 | ttgaaggaag | ccagtccctg | gtgggagaca | ttgaaatgt | gaacatgtgg gactttgtgc |
| 961 | tgtcaccaga | tgagattaac | accatctatc | ttggcgggcc | cttcagtcct aatgtcctga |

-continued

| SEQUENCE |
|---|
| 1021 actggcgggc actgaagtat gaagtgcaag gcgaagtgtt caccaaaccc cagctgtggc |
| 1081 cctgaggccc agctgtgggt cctgaaggta cctcccggtt ttttacaccg catgggcccc |
| 1141 acgtctctgt ctctggtacc tcccgctttt ttacactgca tggttcccac gtctctgtct |
| 1201 ctgggccttt gttccnctat atgcattgca ggcctgctcc accctcctca gcgcctgaga |
| 1261 atggaggtaa agtgtctggt ctgggagctc gttaactatg ctgggaaacg gtccaaaaga |
| 1321 atcagaattt gaggtgtttt gttttcattt ttatttcaag ttggacagat cttggagata |
| 1381 atttcttacc tcacatagat gagaaaacta acacccagaa aggagaaatg atgttataaa |
| 1441 aaactcataa ggcaagagct gagaaggaag cgctgatctt ctatttaatt ccccacccat |
| 1501 gacccccaga aagcaggagg gcattgccca cattcacagg gctcttcagt ctcagaatca |
| 1561 ggacactggc caggtgtctg gtttgggtcc agagtgctca tcatcatgtc atagaactgc |
| 1621 tgggcccagg tctcctgaaa tgggaagccc agcaatacca cgcagtccct ccactttctc |
| 1681 aaagcacact ggaaaggcca ttagaattgc cccagcagag cagatctgct tttttccag |
| 1741 agcaaaatga agcactaggt ataaatatgt tgttactgcc aagaacttaa atgactggtt |
| 1801 tttgtttgct tgcagtgctt tcttaatttt atggctcttc tgggaaactc ctcccctttt |
| 1861 ccacacgaac cttgtggggc tgtgaattct ttcttcatcc ccgcattccc aatatacccca |
| 1921 ggccacaaga gtggacgtga accacagggt gtcctgtcag aggagcccat ctcccatctc |
| 1981 cccagctccc tatctggagg atagttggat agttacgtgt tcctagcagg accaactaca |
| 2041 gtcttcccaa ggattgagtt atggactttg ggagtgagac atcttcttgc tgctggattt |
| 2101 ccaagctgag aggacgtgaa cctgggacca ccagtagcca tcttgtttgc cacatggaga |
| 2161 gagactgtga ggacagaagc caaactggaa gtggaggagc caagggattg acaaacaaca |
| 2221 gagccttgac cacgtggagt ctctgaatca gccttgtctg gaaccagatc tacacctgga |
| 2281 ctgcccaggt ctataagcca ataaagcccc tgtttacttg a |
| SEQ ID NO: 9 (ISIS 329993 (ISIS-CRP$_{Rx}$ (phosphorothioate): AGCATAGTTAACGAGCTCCC |
| SEQ ID NO: 10 (ISIS 353491): GCACTCTGGACCCAAACCAG |
| SEQ ID NO: 11 (ISIS 353512): TCCCATTTCAGGAGACCTGG |
| SEQ ID NO: 12 (cDNA Human C-reactive protein gene) |
| 1 aataaataac tcacattgat ttctctggtc tgaaataatt ttgcttcccc tcttcccgaa |
| 61 gctctgacac ctgccccaac aagcaatgtt ggaaaattat ttacatagtg gcgcaaactc |
| 121 ccttactgct ttggatataa atccaggcag gaggaggtag ctctaaggca agagatctag |
| 181 gacttctagc ccctgaactt tcagccgaat acatctttc caaaggagtg aattcaggcc |
| 241 cttgtatcac tggcagcagg acgtgaccat ggagaagctg ttgtgtttct tggtcttgac |
| 301 cagcctctct catgcttttg gccagacagg taagggccac cccaggctat gggagagttt |
| 361 tgatctgagg tatggggtg gggtctaaga ctgcatgaac agtctcaaaa aaaaaaaaa |
| 421 aagactgtat gaacagaaca gtggagcatc cttcatggtg tgtgtgtgtg tgtgtgtgtg |
| 481 tgtgtgtggt gtgtaactgg agaaggggtc agtctgtttc tcaatcttaa attctatacg |
| 541 taagtgaggg gatagatctg tgtgatctga gaaacctctc acatttgctt gtttttctgg |
| 601 ctcacagaca tgtcgaggaa ggcttttgtg tttcccaaag agtcggatac ttcctatgta |
| 661 tccctcaaag caccgttaac gaagcctctc aaagccttca ctgtgtgcct ccacttctac |
| 721 acggaactgt cctcgacccg tgggtacagt attttctcgt atgccaccaa gagacaagac |

| | SEQUENCE |
|---|---|
| 781 | aatgagattc tcatattttg gtctaaggat ataggataca gttttacagt gggtgggtct |
| 841 | gaaatattat tcgaggttcc tgaagtcaca gtagctccag tacacatttg tacaagctgg |
| 901 | gagtccgcct cagggatcgt ggagttctgg gtagatggga agcccagggg gaggaagagt |
| 961 | ctgaagaagg gatacactgt gggggcagaa gcaagcatca tcttggggca ggagcaggat |
| 1021 | tccttcggtg ggaactttga aggaagccag tccctagtgg gagacattgg aaatgtgaac |
| 1081 | atgtgggact tgtgctgtc accagatgag attaacacca tctatcttgg cgggcccttc |
| 1141 | agtcctaatg tcctgaactg gcgggcactg aagtatgaag tgcaaggcga agtgttcacc |
| 1201 | aaacccagc tgtggccctg aggcccagct gtgggtcctg aaggtacctc ccggtttttt |
| 1261 | acaccgcatg ggccccacgt ctctgtctct ggtacctccc gcttttttac actgcatggt |
| 1321 | tcccacgtct ctgtctctgg gcctttgttc ccctatatgc attgaggcct gctccaccct |
| 1381 | cctcagcgcc tgagaatgga ggtaaagtgt ctggtctggg agctcgttaa ctatgctggg |
| 1441 | aaatggtcca aaagaatcag aatttgaggt gttttgtttt cattttatt tcaagttgga |
| 1501 | cagatcttgg agataatttc ttacctcaca tagatgagaa aactaacacc cagaaaggag |
| 1561 | aaatgatgtt ataaaaaact cataaggcaa gagctgagaa ggaagcgctg atcttctatt |
| 1621 | taattcccca cccatgaccc ccagaaagca ggagcattgc ccacattcac agggctcttc |
| 1681 | agtatcagaa tcaggacact ggccaggtgt ctggtttggg tccagagtgc tcatcatcat |
| 1741 | gtcatagaac tgctgggccc aggtctcctg aaatgggaag cccagcaata ccacgcagtc |
| 1801 | cctccacttt ctcaaagcac actggaaagg ccattagaat tgccccagca gagcagatct |
| 1861 | gcttttttc cagagcaaaa tgaagcacta ggtataaata tgttgttact gccaagaact |
| 1921 | taaatgactg gttttgttt gcttgcagtg ctttcttaat tttatggctc ttctgggaaa |
| 1981 | ctcctcccct tttccacacg aaccttgtgg ggctgtgaat tctttcttca tccccgcatt |
| 2041 | cccaatatac ccaggccaca agagtggacg tgaaccacag ggtgtcctgt cagaggagcc |
| 2101 | catctcccat ctccccagct ccctatctgg aggatagttg gataggtacg tgttcctagc |
| 2161 | aggaccaact acagtcttcc caaggattga gttatggact tgggagtga gacatcttct |
| 2221 | tgctgctgga tttccaagct gagaggacgt gaacctggga ccaccagtag ccatcttgtt |
| 2281 | tgccacatgg agagagactg tgaggacaga agccaaactg gaagtggagg agccaaggga |
| 2341 | ttgacaaaca acagagcctt gaccacgtgg agtctctgaa tcagccttgt ctggaaccag |
| 2401 | atctacacct ggactgccca ggtctataag ccaataaa |

SEQ ID NO: 13 (amino acid Human C-reactive protein gene)
MEKLLCFLVLTSLSHAFGQTDMSRKAFVFPKESDTSYVSLKAPLTKPLKAFTVCLHFYTELSSTRGYSIFSYATKR

QDNEILIFWSKDIGYSFTVGGSEILFEVPEVTVAPVHICTSWESASGIVEFWVDGKPRVRKSLKKGYTVGAEASII

LGQEQDSFGGNFEGSQSLVGDIGNVNMWDFVLSPDEINTIYLGGPFSPNVLNWRALKYEVQGEVFTKPQLWP

INCORPORATION BY REFERENCE

The entire contents of all patents, published patent applications, websites, and other references cited herein are hereby expressly incorporated herein in their entireties by reference.

---

What is claimed is:

1. A method for treating or managing an inflammatory bowel disease (IBD) in a patient having the IBD, wherein the method comprises:
   (a) administering to the patient an initial dose of a SMAD7 antisense-oligonucleotide;
   (b) analyzing the level of C-reactive protein (CRP) in the patient; and
   (c) if the level of CRP is above a normal level of CRP, then administering to the patient a subsequent dose that is greater than or equal to the initial dose, or, if the level of CRP is below a normal level of CRP, then administering to the patient a subsequent dose that is equal to or smaller than the initial dose,
   wherein the normal level of CRP is about 0.01 mg/L, about 0.05 mg/L, about 0.1 mg/L, about 0.2 mg/L, about 0.3 mg/L, about 0.4 mg/L, about 0.5 mg/L, between 0.5 mg/L and 3 mg/L, between 1 mg/L and 3 mg/L, between 1.5 mg/L and 3 mg/L, between 2 mg/L and 3 mg/L, between 2.5 mg/L and 3 mg/L, or about 3.0 mg/L.

2. A method for treating or managing an inflammatory bowel disease (IBD) in a patient having the IBD, wherein the method comprises:
   (a) analyzing the level of CRP in the patient; and
   (b) if the level of CRP is above a threshold level of CRP, then administering to the patient an initial dose of a SMAD7 antisense-oligonucleotide,
   wherein the threshold level of CRP is about 0.5 mg/L, about 1.0 mg/L, about 1.5 mg/L, about 2.0 mg/L, about 2.5 mg/L, about 3.0 mg/L, about 3.5 mg/L, about 4.0 mg/L, about 4.5mg/L, about 5.0 mg/L, about 7.5 mg/L, or about 10.0 mg/L.

3. The method of claim 2, wherein the threshold level of CRP is about 3.0 mg/L.

4. The method of claim 2, wherein the method further comprises:
   (c) analyzing the level of CRP in the patient after said administering step; and
   (d) if the level of CRP is above a normal level of CRP, then administering to the patient a subsequent dose that is greater than or equal to the initial dose, or, if the level of CRP is below a normal level of CRP then administering to the patient a subsequent dose that is equal to or smaller than the initial dose,
   wherein the normal level of CRP is about 0.01 mg/L, about 0.05 mg/L, about 0.1 mg/L, about 0.2 mg/L, about 0.3 mg/L, about 0.4 mg/L, about 0.5 mg/L, between 0.5 mg/L and 3 mg/L, between 1 mg/L and 3 mg/L, between 1.5 mg/L and 3 mg/L, between 2 mg/L and 3 mg/L, between 2.5 mg/L and 3 mg/L, or about 3.0 mg/L.

5. The method of claim 1, wherein the initial dose is at least 10 mg/day, at least 20 mg/day, at least 30 mg/day, at least 40 mg/day, at least 50 mg/day, at least 60 mg/day, at least 70 mg/day, at least 80 mg/day, or at least 90 mg/day.

6. The method of claim 1, wherein the initial dose is 10 mg/day, 40 mg/day, 80 mg/day, or 160 mg/day.

7. The method of claim 1, wherein, if the CRP level is above the normal level, the subsequent dose is at least about 10 mg/day, at least about 20 mg/day, at least about 30 mg/day, at least about 40 mg/day, at least about 50 mg/day, at least about 60 mg/day, at least about 70 mg/day, at least about 80 mg/day, at least about 90 mg/day, at least about 100 mg/day, at least about 110 mg/day, at least about 120 mg/day, at least about 130 mg/day, at least about 140 mg/day, at least about 150 mg/day, or at least about 160 mg/day greater than the initial dose.

8. The method of claim 1, wherein, if the CRP level is below the normal level, the subsequent dose is at least about 10 mg/day, at least about 20 mg/day, at least about 30 mg/day, at least about 40 mg/day, at least about 50 mg/day, at least about 60 mg/day, at least about 70 mg/day, or at least about 80 mg/day smaller than the initial dose.

9. The method of claim 1, wherein the initial dose is between about 10 mg/day and 100 mg/day, and the subsequent dose is between about 30 mg/day and 200 mg/day.

10. The method of claim 2, wherein the method further comprises:
(c) analyzing the level of CRP in the patient after said administering step; and
(d) if the level of CRP is lower after said administration step than the level of CRP before said administration step, then administering to the patient a subsequent dose that is the same as the initial dose or smaller than the initial dose, or, if the level of CRP is unchanged or increased after said administration step compared to the level of CRP before said administration step, then administering to the patient a subsequent dose that is the same as the initial dose or greater than the initial dose or terminating the treatment.

11. The method of claim 10, wherein if the patient is in clinical remission and the level of CRP is unchanged or increased after said administration step compared to the level of CRP before said administration step, then terminating the treatment.

12. The method of claim 10, wherein, if the level of CRP is at least 10%, at least 20%, at least 30%, at least 40%, at least 50%, or at least 70% decreased after said administration step compared to the level of CRP before said administration step, then administering to the patient a subsequent dose that is the same as the initial dose or smaller than the initial dose.

13. The method of claim 10, further comprising determining that the patient responds to the treatment if the level of CRP is lower after administering the initial dose than the level of CRP before administering the initial dose.

14. The method of claim 10, further comprising determining that the patient responds to the treatment if the patient displays a decrease in CDAI of at least 70 points from baseline, a decrease of SES-CD of at least 4 points from baseline, or a decrease of PRO-2 of at least 4 points from baseline.

15. The method of claim 10, further comprising determining that the patient is in remission if the level of CRP is lower after administering the initial dose than the level of CRP before administering the initial dose.

16. The method of claim 10, further comprising determining that the patient is in remission if the patient displays a CDAI of <150, an SES-CD score of ≤2, or a PRO-2 score of ≤8.

17. The method of claim 1, wherein the IBD is Crohn's disease (CD) or ulcerative colitis (UC).

18. The method of claim 1, wherein the SMAD7 antisense oligonucleotide is administered orally to the patient having the IBD.

19. The method of claim 1, wherein the SMAD7 antisense oligonucleotide targets region 108-128 of human SMAD7 (SEQ ID NO: 2).

20. The method of claim 1, wherein the SMAD7 antisense oligonucleotide targets nucleotides 403, 233, 294, 295, 296, 298, 299 or 533 of human SMAD7 (SEQ ID NO: 2).

21. The method of claim 1, wherein the SMAD7 antisense oligonucleotide comprises the nucleotide sequence of SEQ ID NO: 3 (5'-GTCGCCCCTTCTCCCCGCAGC-3').

22. The method of claim 1, wherein the SMAD7 antisense oligonucleotide is an antisense oligonucleotide phosphorothioate against SMAD7 comprising the following sequence: 5'-GTXGCCCCTTCTCCCXGCAG-3' (SEQ ID NO: 4), wherein X is 5-methyl-2'-deoxycytidine and wherein the internucleoside linkages are phosphorothioate linkages.

23. The method of claim 1, wherein the SMAD7 antisense oligonucleotide is an antisense oligonucleotide phosphorothioate against SMAD7 comprising the following sequence: 5'-GTXGCCCCTTCTCCCXGCAGC-3' (SEQ ID NO: 1), wherein X is 5-methyl -2'-deoxycytidine and wherein the internucleoside linkages are phosphorothioate linkages.

24. The method of claim 1, wherein the SMAD7 antisense oligonucleotide is an antisense oligonucleotide according to Chemical Abstracts Service Registry Number (CAS RN) 1443994-98-6 or of CAS RN 1443994-46-4.

25. The method of claim 1, wherein the normal level of CRP is about 3.0 mg/L.

26. The method of claim 4, wherein the normal level of CRP is about 3.0 mg/L.

* * * * *